(12) United States Patent
Deraeve et al.

(10) Patent No.: US 8,324,196 B2
(45) Date of Patent: Dec. 4, 2012

(54) POLYQUINOLINE DERIVATIVES AND THE THERAPEUTIC USE THEREOF

(75) Inventors: Céline Deraeve, Toulouse (FR);
Marguerite Pitie, Ramonville (FR);
Christophe Boldron, Toulouse (FR);
Bernard Meunier, Castanet (FR)

(73) Assignees: Palumed S.A., Castanet-Tolosan (FR);
Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 13/549,729

(22) Filed: Jul. 16, 2012

(65) Prior Publication Data
US 2012/0277265 A1 Nov. 1, 2012

Related U.S. Application Data

(62) Division of application No. 11/997,821, filed as application No. PCT/FR2006/001906 on Aug. 4, 2006, now Pat. No. 8,247,396.

(30) Foreign Application Priority Data

Aug. 4, 2005 (FR) ...................................... 05 08351

(51) Int. Cl.
*A61K 31/33* (2006.01)
(52) U.S. Cl. ....................................................... 514/183
(58) Field of Classification Search ................... 514/183
See application file for complete search history.

(56) References Cited

FOREIGN PATENT DOCUMENTS
WO 2004007461 1/2004

OTHER PUBLICATIONS

Fanning et al 'Some transition metal complexes of 8-aminoquinoline' Journal of Inorganic Nuclear Chemistry, vol. 27, p. 2217-2223, 1965.
Patani et al 'Bioisosterism: A Rational Approach to Drug Design' Chemical Reviews, vol. 96, p. 3147-3176, 1996.
Brent, R. et al., "Chemical Genetic and Genomic Approaches Reveal a Role for Copper in Specific Gene Activation", Journal of The American Chemical Society, vol. 121, 1999, XP002381594, pp. 10662 and 10663.

*Primary Examiner* — Brandon Fetterolf
*Assistant Examiner* — Christopher R Stone
(74) *Attorney, Agent, or Firm* — Young & Thompson

(57) ABSTRACT

The invention relates to a method for chelating metal ion and/or dissolving amyloid aggregates, including chelating metal ions and/or dissolving amyloid aggregates with a compound of formula (I):

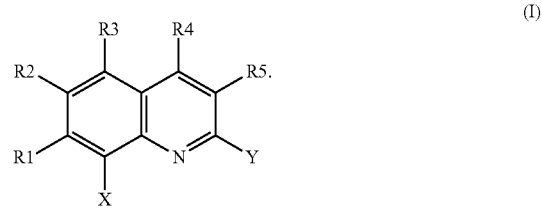

7 Claims, 9 Drawing Sheets

Figure 2:
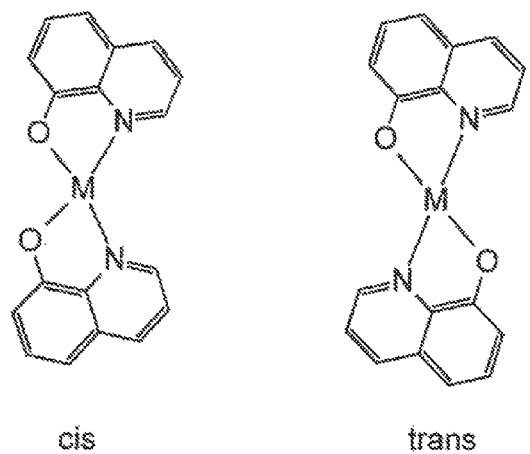

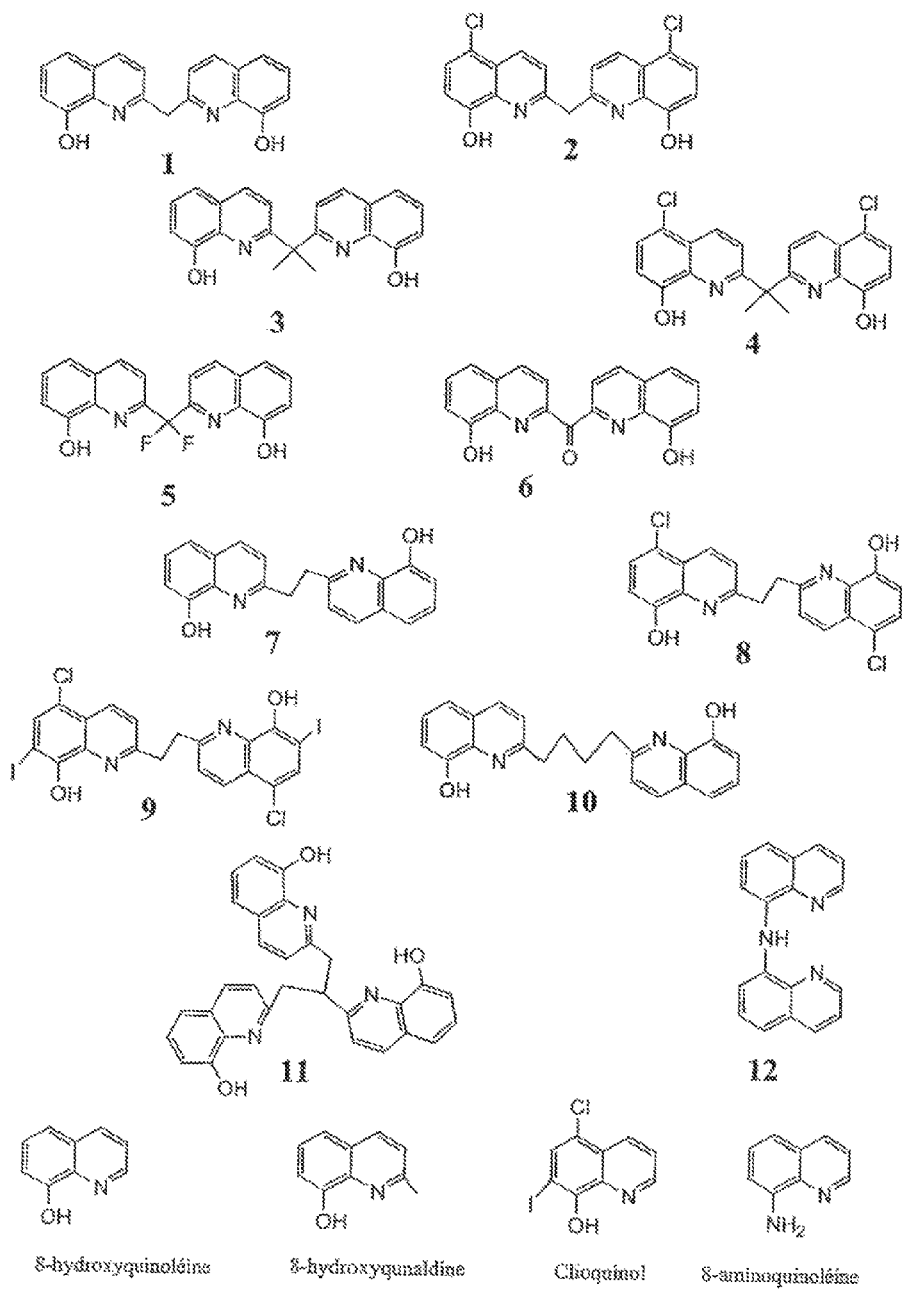
FIG.1 ( start )

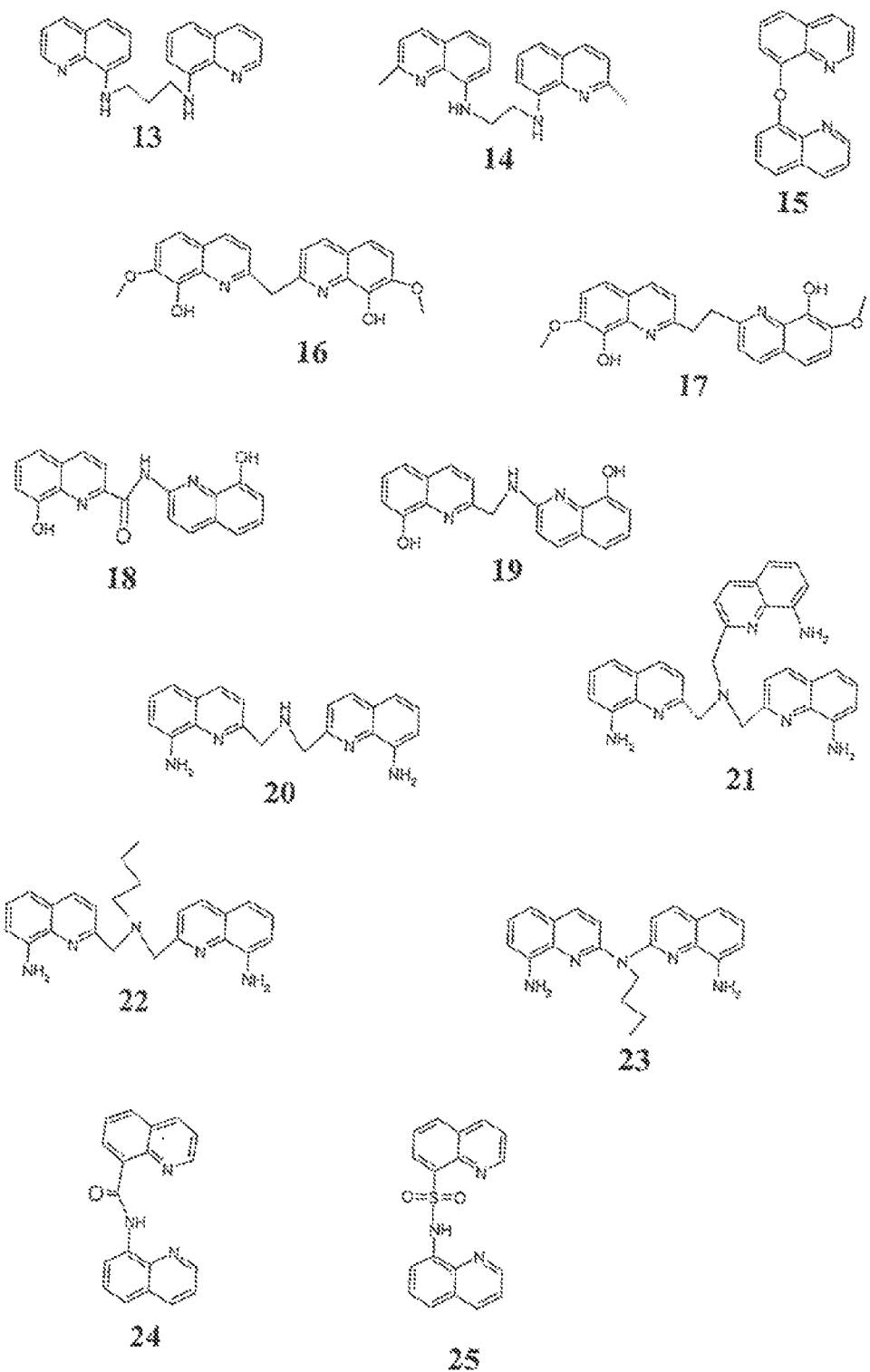
FIG.1 (end)

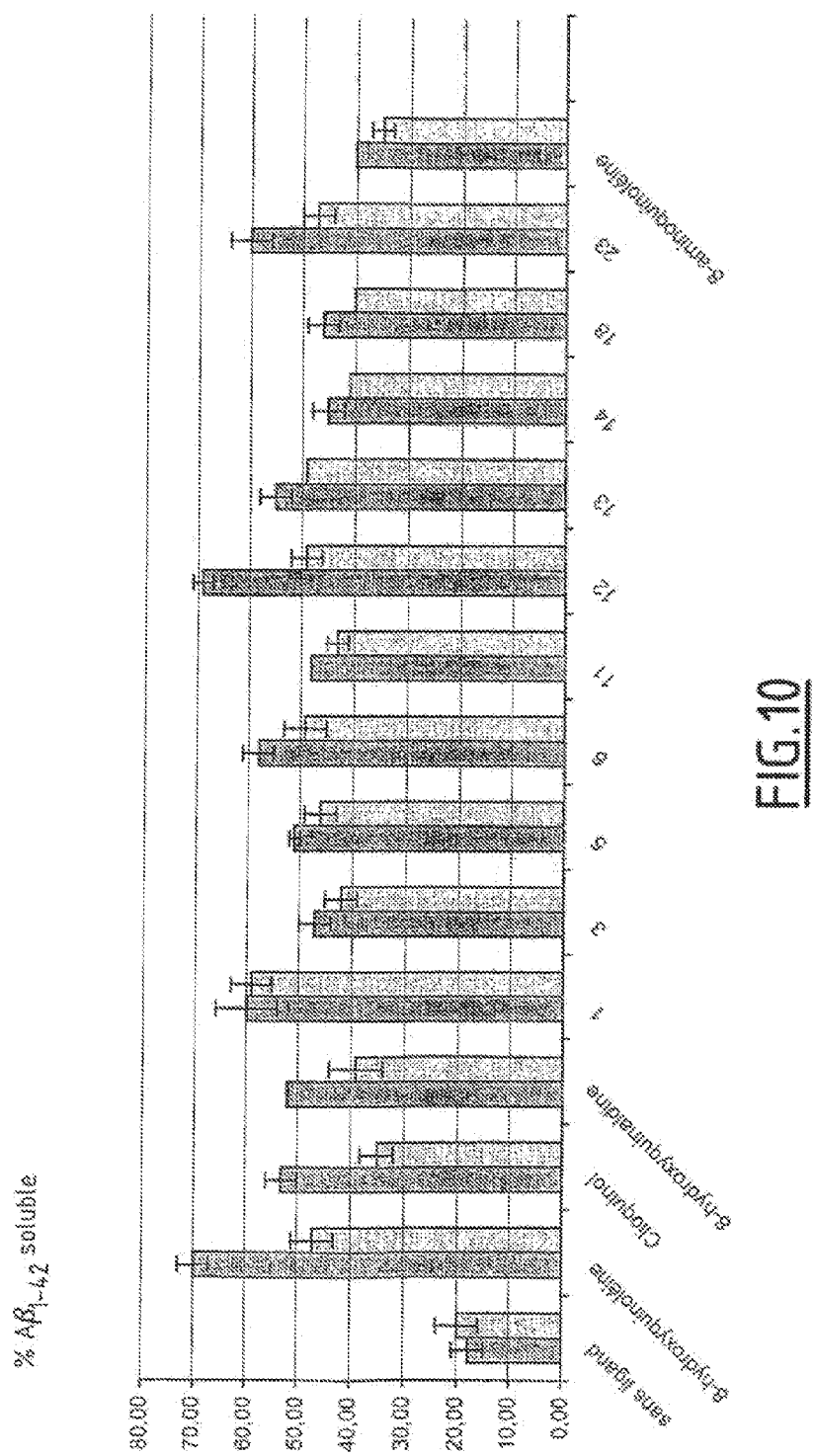

POLYQUINOLINE DERIVATIVES AND THE THERAPEUTIC USE THEREOF

CROSS REFERENCE TO RELATED APPLICATIONS

This application is a division of copending application Ser. No. 11/997,821 filed on Feb. 4, 2008; which is the 35 U.S.C. 371 national stage of International application PCT/FR2006/001906 filed on Aug. 4, 2006; which claims priority to French application 0508351 filed on Aug. 4, 2005. The entire contents of each of the above-identified applications are hereby incorporated by reference.

BACKGROUND OF THE INVENTION

The present invention relates to novel polyquinoline derivatives, to the process for the preparation thereof and to the use thereof as therapeutic agents.

More precisely, compounds according to the present invention are metal ligands and/or dissolve amyloid aggregates and are particularly effective in the treatment of neurodegenerative diseases.

DESCRIPTION OF THE RELATED ART

Various journals summarise data which demonstrates that many progressive and slow neurodegenerative diseases are associated with: (i) an oxidative stress, (ii) protein misfolding leading to aggregate, fibril, profibril or plaque formation, (iii) an accumulation of these proteins, (iv) synapse loss, (v) homeostasis of the metal ions which have been modified, (vi) axonal and dendritic transport failure, (vii) neural death. (E. Bossy-Wetzel et al., *Nature Medecine*, 2004, S2-S9; K. J. Barnham et al., *Nature Rev. Drug Discov.*, 2004, 3, 205-214; M. P. Mattson, *Nature*, 2004, 430, 631-639; P. M. Doraiswamy et al., *The Lancet Neurol.*, 2004, 3, 431-434).

Many studies have recently demonstrated the fundamental role of metal ions (copper, zinc, iron, aluminium, manganese, etc.) in the modification of protein folding and aggregation, leading to serious pathologies. This destructive role of abnormal metal ion-protein interaction has recently been emphasised in many neurodegenerative diseases, (for example: Alzheimer's disease, spongiform encephalopathies, Parkinson's disease, Huntington's disease, amyotrophic lateral sclerosis, etc.) or during the harmful development of some disabilities, as in the case of Down syndrome. A specific protein or specific proteins are associated with each disease, and it has been demonstrated that metal ion chelating agents can be activated to reduce their misfolding brought about by the metals.

In some encephalopathies, such as Creutzfeldt-Jakob's disease and its new variant, it is now acknowledged that these diseases are linked to the transformation of a prion-type protein (PrP) in its pathological and infectious form, known as "scrapie" ($PrP^{sc}$). Cupric ions are involved in this conformational modification (beta-sheet formation) of the prions, which acquire protease resistance and become insoluble in non-denaturant detergents. Recent works have shown that a ligand such as bathocuproine disulfate can restore in vitro "scrapie" protein $PrP^{sc}$ protease sensitivity and the solubility thereof (E. Quaglio et al., *J. Biol. Chem.*, 2001, 276, 11432-11438).

In the case of Parkinson's disease, the α-synuclein interacts with ferric ions. It has been suggested that these ions facilitate hydroxyl radical formation, in particular oxidising hydroxyl radical formation, and studies using MRI post mortem have shown high concentrations of ferric ions in patients' substancia nigra (a region of the brain where dopaminergic neurones are more selectively affected in this disease). Use of chelators such as Clioquinol reduces the toxicity of 1-methyl-4-phenyl-1,2,3,6-tetrapyridine, a toxin which causes Parkinson's disease, in mice (D. Kaur et al., *Neuron* 2003, 37, 899-909).

In the case of Alzheimer's disease (M. P. Mattson, *Nature*, 2004, 430, 631-639; M. Citron, *Nature Rev. Neurosci.*, 2004, 5, 677-685), the pathology is linked to aggregation, in the brain, of β-amyloid peptides, leading to amyloid plaque formation. This aggregation may be induced by Cu(II) and Zn(II) ions and, to a lesser extent, by Fe(III) ions. Accumulation within these redox-active metal ion plaques is likely to cause significant oxidative stress (via $H_2O_2$ production), itself damaging the neurones in the brain, leading to an irreversible loss of intellectual abilities (M. P. Cuajungco et al., *Ann. N.Y. Acad. Sci.*, 2000, 920, 292-304; C. S. Atwood et al., *Met. Ions Biol. Syst.*, 1999, 36, 309-364). The fact that the first tests to be carried out using a metal ion ligand such as Clioquinol led to improvements in Alzheimer's disease (R. A. Cherny et al., *Neuron*, 2001, 30, 665-676) indicates that therapeutic approaches using metal ion chelators are possible.

However, these chelators must have the following properties to be able to be used as drugs in the treatment of neurodegenerative diseases:
(a) have a low molecular weight and not be too highly charged in order to be able to cross the various barriers (firstly, intestinal, in the case of a molecule taken orally and then, in a reversible manner, the blood-brain barrier for chelating the metal ions present in excess in the pathogenic proteins),
(b) have a modifiable structure in order to adjust chelation selectivity to specific metal ions (a strong, non-specific chelation would result in a general depletion of metal ions, including those of metalloenzymes, which are essential to the functioning of the organism) or to make it possible to modulate the biodistribution thereof in the organism.

Chelators with a quinoline unit substituted in position 8 by a heteroatom (such as 8-hydroxyquinoline derivatives, for example) are candidates for chelating the excess metal ions involved in the neurodegenerative diseases. This type of ligand is expected often to form copper, zinc or iron complexes (metal ions associated with protein aggregation and even oxidative stress, with regard to copper and iron), comprising two (and even three in the case of iron) ligands around the metal ion (Sillen, L. G. et al., *Stability Constants of Metal-Ion Complexes*, The Chemical Society London Publication, 1971).

Bis-quinoline derivatives have been described, but rarely as agents for the treatment of potential diseases of the nervous system. WO 2004/007461 thus describes the property of a metal chelator. However, this document basically describes mono-quinoline compounds. Furthermore, EP 0 443 862 describes NMDA receptor agonist derivatives, and in no way suggests metal chelator activity of the described compounds. Finally, Stockwell et al. in *J. Am. Chem. Soc.* 1999, 10662-10663 describe the biological activity of the compounds 2,2'-(imino)bis(8-quinolinol) and its derivatives 2,2'-(methylimino)- and 2,2'-(n-butylimino)-bis(8-quinolinol).

SUMMARY OF THE INVENTION

It has now surprisingly been found that the 2,2'- or 8,8'-poly-quinoline compounds according to the invention have a strong metal-chelating activity and/or are able to dissolve amyloid aggregates.

The term "amyloid aggregates" denotes a polymeric structure of Aβ peptides generated by secondary, tertiary or quaternary interaction (of sheet 6, for example) or by biometallic coordination on the peptide (E. Scarpini et al., *The Lancet Neurology*, 2003, 2, 539-547; E. Gaggeli et al., *Chem. Rev.*, 2006, 106, 1995-2044; A. B. Clippingdale et al., *J. Peptide Sc.*, 2001, 7, 227-249).

These compounds are useful as drugs for the treatment and/or prevention of neurodegenerative diseases, in particular Alzheimer's disease, Parkinson's disease, spongiform encephalopathies, Huntington's disease, amyothrophic lateral sclerosis or Down syndrome.

The present inventors have thus developed chelators comprising a plurality of small substituted quinoline units (in position 2 or 8) which are sufficiently hydrophobic to be able to cross barriers. They have thus demonstrated that these structures aid interaction of molecule heterocycles on the same metal ion and that substitutions on these ligands, which have been introduced in a controlled manner, can modulate the action thereof with respect to proteins involved in neurodegenerative diseases: properties of chelation, in particular of Cu(II), Zn(II) and Fe(III) ions involved in these diseases, of hydrophobicity, of the capacity to disaggregate proteins involved in neurodegenerative diseases whether or not in the presence of metal ion, or of decreasing the oxidative stress that they can induce.

BRIEF DESCRIPTION OF THE INVENTION

The present invention relates to the use of compounds of formula (I)

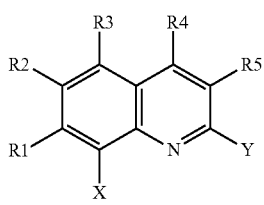

(I)

for the preparation of pharmaceutical compositions for chelating metal ions and/or dissolving amyloid aggregates wherein in formula (I)
either
X represents an —OR, —NRR', —S(O)$_p$R, —OCOR or —OCOOR group, and
Y represents a group of formula:

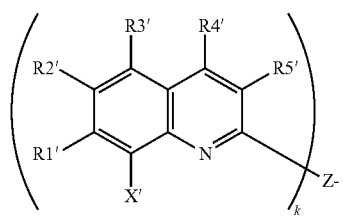

(IY)

in which X' represents an —OR, —NRR', —S(O)$_p$R, —OCOR or —OCOOR group and
Z represents a group of formula -(A)$_m$-(Alk)$_n$-(A')$_{m'}$-(Alk')$_{n'}$-(A")$_{m''}$-(Alk")$_{n'''}$, where m, n, m', n', m" and n" are the same or different and independently represent 0 or 1, it being understood that at least one of m, n, m', n' m" and n" is equal to 1,
A, A' and A" are the same or different and independently represent a group selected from —NR—, —S(O)$_p$—, —O— and —C(=O)—, or a 4-11 membered ring selected from cycloalkyls, heterocycles, aryls and heteroaryls, said ring being optionally substituted by one or more substituents selected from alkyl, OR, NRR', CF$_3$, Hal, CN, S(O)$_p$R, COOR, OCOOR, CONRR' and NRCOOR';
Alk, Alk' and Alk" are the same or different and independently represent an -alkyl-group optionally substituted by one or more substituents selected from OR, NRR', CF$_3$, Hal, CN, S(O)$_p$R, COOR, OCOOR, CONRR' and NRCOOR';
Or
X represents a group of formula:

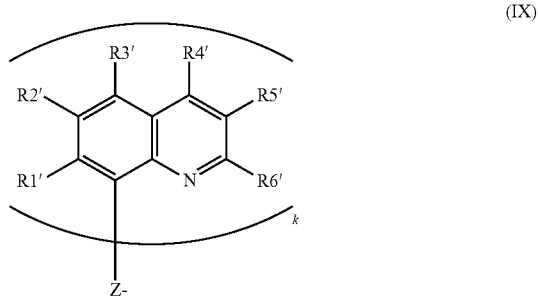

(IX)

in which Z represents a group of formula -(A)$_m$-(Alk)$_n$-(A')$_{m'}$-(Alk')$_{n'}$-(A")$_{m''}$-(Alk")$_{n'''}$, where m, n, m', n', m" and n" are the same or different and independently represent 0 or 1, it being understood that at least one of m, n, m', n' m" and n" is equal to 1,
A, A' and A" are the same or different and independently represent a group selected from —NR—, —S(O)$_p$—, —O— and —C(=O)—, or a 4-11 membered ring selected from cycloalkyls, heterocycles, aryls and heteroaryls, said ring being optionally substituted by one or more substituents selected from alkyl, OR, NRR', CF$_3$, Hal, CN, S(O)$_p$R, COOR, OCOOR, CONRR' and NRCOOR';
Alk, Alk' and Alk" are the same or different and independently represent an -alkyl-group, optionally substituted by one or more substituents selected from OR, NRR', CF$_3$, Hal, CN, S(O)$_p$R, COOR, OCOOR, CONRR' and NRCOOR';
Y represents a group selected from H, OR, NRR', Hal, —CN, —CF$_3$ and alkyl optionally substituted by one or more substituents selected from OR, NRR', CF$_3$, Hal, CN, S(O)$_p$R, COOR, OCOOR, CONRR' and NRCOOR';
and
R and R' are the same or different and independently represent a hydrogen atom or a cycloalkyl or alkyl group optionally substituted by one or more groups selected from OR, NRR', Hal, —CN, —CF$_3$, S(O)$_p$R, COOR, OCOOR, CONRR' and NRCOOR'; heteroaryl;
R1, R2, R3, R4, R5, R1', R2', R3, R4', R5' and R6' are the same or different and independently represent a group or atom selected from H, OR, NRR', Hal, —CN, —CF$_3$, S(O)$_p$R, COOR, OCOOR, CONRR', NRCOOR' and alkyl optionally substituted by one or more groups selected from OR, NRR', Hal, —CN, —CF$_3$, S(O)$_p$R, COOR, OCOOR, CONRR' and NRCOOR';
k represents 1 or 2;
p represents 0, 1 or 2;

as well as the pharmaceutically acceptable stereoisomers or mixtures, tautomeric forms, hydrates, solvates, salts, free forms and esters thereof,
with the exception of compounds for which:
X represents an —OH group, and
Y represents a group of formula:

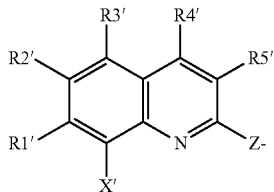

in which X' represents an —OH group, and
Z represents a group selected from —NH—, —NBu-, —NMe-, and
R1, R2, R3, R4, R5, R1', R2', R3', R4', R5' and R6' are equal to H.

More preferably, compounds for the present use are selected from:
dimethyl-bis[8-(acetyloxy)-2-quinoline]propanedioate
2,2'-methanediyl-bis(8-hydroxyquinoline)
2,2'-methanediyl-bis(5-chloro-8-hydroxyquinoline)
2,2'-(2,2-propanediyl)-bis(8-hydroxyquinoline)
2,2'-(2,2-propanediyl)-bis(5-chloro-8-hydroxyquinoline)
2,2'-(difluoromethanediyl)-bis(8-hydroxyquinoline)
bis(8-hydroxy-2-quinolinyl)methanone
2,2'-(1,2-ethanediyl)-bis[8-(methyloxy)quinoline]
2,2'-(1,2-ethanediyl)-bis(8-hydroxyquinoline)
2,2'-(1,2-ethanediyl)-bis(5-chloro-8-hydroxyquinoline)
2,2'-(1,2-ethanediyl)-bis(5-chloro-7-iodo-8-hydroxyquinoline)
2,2'-(1,4-butanediyl)-bis[8-(methyloxy)quinoline]
2,2'-(1,4-butanediyl)-bis(8-hydroxyquinoline)
2,2',2''-(1,2,3-propanetriol)-tris[8-(methyloxy)quinoline]
2,2',2''-(1,2,3-propanetriol)-tris(8-hydroxyquinoline)
bis(8-quinolinyl)amine
N,N'-di-8-quinolinyl-1,3-propanediamine
8,8'-oxydiquinoline
N,N'-bis(2-methyl-8-quinolinyl)-1,2-ethanediamine
dimethyl bis{7-(methyloxy)8-[phenylmethyl)oxy]-2-quinolinyl}propanedioate
2,2'-(methanediyl)-bis(7-methyloxy-8-hydroxy-2-quinolinium)dichloride
2,2'-(1,2-ethanediyl)-bis[7-(methyloxy)-8-quinolinol]
8-hydroxy-N-(8-hydroxy-2-quinolinyl)-2-quinoline carboxamide
2-{[8-hydroxy-2-quinolinyl)amino]methyl}-8-quinolinol
2,2'-(iminodimethanediyl)di(N-boc-8-quinoline amine)
2,2'-(Iminodimethanediyl)di(8-quinoline amine)
2,2',2''-(nitrilotrimethanediyl)tri(N-boc-8-quinoline amine)
2,2',2''-(nitrilotrimethanediyl)tri(8-quinoline amine)
2,2'-[(butylimino)dimethanediyl]di(N-boc-8-quinoline amine)
2,2'-[(butylimino)dimethanediyl]di(8-quinoline amine)
N-butyl-2,2'-imino-bis(8-quinoline amine)
N-8-quinolinyl-8-quinoline carboxamide
N-8-quinolinyl-8-quinoline sulfonamide
as well as the pharmaceutically acceptable stereoisomers or mixtures, tautomeric forms, hydrates, solvates, salts, free forms and esters thereof.

According to another subject-matter, the present invention also relates to use of compounds of formula (I)

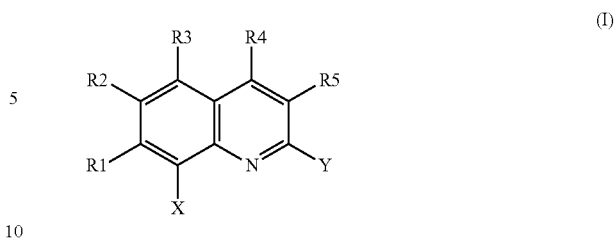

for the preparation of pharmaceutical compositions for preventing and/or treating diseases affecting the central nervous system, such as neurodegenerative diseases
wherein in formula (I):
either
X represents an —OR, —NRR', —S(O)$_p$R, —OCOR or —OCOOR group and
Y represents a group of formula:

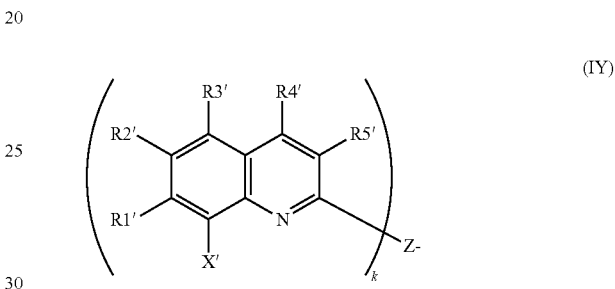

in which X' represents an —OR, —NRR', —S(O)$_p$R, —OCOR or —OCOOR group and
Z represents a group of formula -(A)$_m$-(Alk)$_n$-(A')$_{m'}$-(Alk')$_{n'}$-(A'')$_{m''}$-(Alk'')$_{n''}$, where m, n, m', n', m'' and n'' are the same or different and independently represent 0 or 1, it being understood that at least one of m, n, m', n' m'' and n'' is equal to 1, A, A' and A'' are the same or different and independently represent a group selected from —NR—, —S(O)$_p$—, —O— and —C(═O)—, or a 4-11 membered ring selected from cycloalkyls, heterocycles, aryls and heteroaryls, said ring being optionally substituted by one or more substituents selected from alkyl, OR, NRR', CF$_3$, Hal, CN, S(O)$_p$R, COOR, OCOOR, CONRR' and NRCOOR';
Alk, Alk' and Alk'' are the same or different and independently represent an -alkyl-group, optionally substituted by one or more substituents selected from OR, NRR', CF$_3$, Hal, CN, S(O)$_p$R, COOR, OCOOR, CONRR' and NRCOOR';
or
X represents a group of formula:

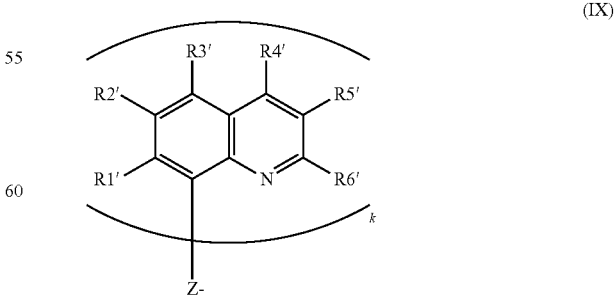

in which Z represents a group of formula -(A)$_m$-(Alk)$_n$-(A')$_{m'}$-(Alk')$_{n'}$-(A'')$_{m''}$-(Alk'')$_{n''}$ where m, n, m', n', m'' and n'' are the same or different and independently represent 0 or 1, it being understood that at least one of m, n, m', n' m'' and n''' is equal to 1, A, A' and A'' are the same or different and independently represent a group selected from —NR—, —S(O)p-, —O— and —C(=O)—, or a 4-11 membered ring selected from cycloalkyls, heterocycles, aryls and heteroaryls, said ring being optionally substituted by one or more substituents selected from alkyl, OR, NRR', CF$_3$, Hal, CN, S(O)$_p$R, COOR, OCOOR, CONRR' and NRCOOR';

Alk, Alk' and Alk'' are the same or different and independently represent an -alkyl-group, optionally substituted by one or more substituents selected from OR, NRR', CF$_3$, Hal, CN, S(O)$_p$R, COOR, OCOOR, CONRR' and NRCOOR';

Y represents a group selected from H, OR, NRR', Hal, —CN, —CF$_3$ and alkyl optionally substituted by one or more substituents selected from OR, NRR', CF$_3$, Hal, CN, S(O)$_p$R, COOR, OCOOR, CONRR' and NRCOOR';
and R and R' are the same or different and independently represent a hydrogen atom or a cycloalkyl or alkyl group, optionally substituted by one or more groups selected from OR, NRR', Hal, —CN, —CF$_3$, S(O)$_p$R, COOR, OCOOR, CONRR' and NRCOOR'; heteroaryl;

R1, R2, R3, R4, R5, R1', R2', R3', R4', R5' and R6' are the same or different and independently represent a group or atom selected from H, OR, NRR', Hal, —CN, —CF$_3$, S(O)$_p$R, COOR, OCOOR, CONRR', NRCOOR', and alkyl optionally substituted by one or more substituents selected from OR, NRR', CF$_3$, Hal, CN, S(O)$_p$R, COOR, OCOOR, CONRR' and NRCOOR';

k represents 1 or 2;

p represents 0, 1 or 2;

as well as the pharmaceutically acceptable stereoisomers or mixtures, tautomeric forms, hydrates, solvates, salts, free forms and esters thereof, with the exception of compounds for which:
X represents an —OH group, and
Y represents a group of formula:

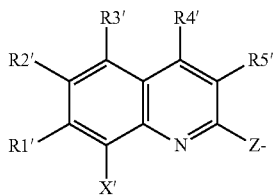

in which X' represents an —OH group,
Z represents a group selected from —NBu-, —NMe-, and
R1, R2, R3, R4, R5, R1', R2', R3', R4', R5' and R6' are equal to H
and compounds for which
X represents a group of formula:

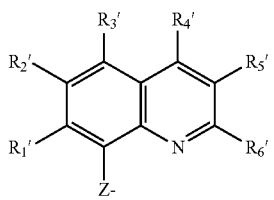

in which Z represents a group of formula —(NH)—(CH$_2$)$_2$—(NH)—(CH$_2$)$_2$—(NH)—,
Y represents H
R1, R2, R3, R4, R5, R1', R2', R3', R4', R5' and R6' represent H.

More preferably, compounds for the present use according to the invention are selected from:
dimethyl-bis[8-(acetyloxy)-2-quinoline]propanedioate
2,2'-methanediyl-bis(8-hydroxyquinoline)
2,2'-methanediyl-bis(5-chloro-8-hydroxyquinoline)
2,2'-(2,2-propanediyl)-bis(8-hydroxyquinoline)
2,2'-(2,2-propanediyl)-bis(5-chloro-8-hydroxyquinoline)
2,2'-(difluoromethanediyl)-bis(8-hydroxyquinoline)
bis(8-hydroxy-2-quinolinyl)methanone
2,2'-(1,2-ethanediyl)-bis[8-(methyloxy)quinoline]
2,2'-(1,2-ethanediyl)-bis(8-hydroxyquinoline)
2,2'-(1,2-ethanediyl)-bis(5-chloro-8-hydroxyquinoline)
2,2'-(1,2-ethanediyl)-bis(5-chloro-7-iodo-8-hydroxyquinoline)
2,2'-(1,4-butanediyl)-bis[8-(methyloxy)quinoline]
2,2'-(1,4-butanediyl)-bis(8-hydroxyquinoline)
2,2',2''-(1,2,3-propanetriol)-tris[8-(methyloxy)quinoline]
2,2',2''-(1,2,3-propanetriol)-tris(8-hydroxyquinoline)
bis(8-quinolinyl)amine
N,N'-di-8-quinolinyl-1,3-propanediamine
8,8'-oxydiquinoline
N,N'-bis(2-methyl-8-quinolinyl)-1,2-ethanediamine
dimethyl bis{7-(methyloxy)8-[phenylmethyl)oxy]-2-quinolinyl}propanedioate
2,2'-(methanediyl)-bis(7-methyloxy-8-hydroxy-2-quinolinium)dichloride
2,2'-(1,2-ethanediyl)-bis[7-(methyloxy)-8-quinolinol]
8-hydroxy-N-(8-hydroxy-2-quinolinyl)-2-quinoline carboxamide
2-{[8-hydroxy-2-quinolinyl)amino]methyl}-8-quinolinol
2,2'-(iminodimethanediyl)di(N-boc-8-quinoline amine)
2,2'-(iminodimethanediyl)di(8-quinoline amine)
2,2',2''-(nitrilotrimethanediyl)tri(N-boc-8-quinoline amine)
2,2',2''-(nitrilotrimethanediyl)tri(8-quinoline amine)
2,2'-[(butylimino)dimethanediyl]di(N-boc-8-quinoline amine)
2,2'-[(butylimino)dimethanediyl]di(8-quinoline amine)
N-butyl-2,2'-imino-bis(8-quinoline amine)
N-8-quinolinyl-8-quinoline carboxamide
N-8-quinolinyl-8-quinoline sulfonamide
as well as the pharmaceutically acceptable stereoisomers or mixtures, tautomeric forms, hydrates, solvates, salts, free forms and esters thereof.

In particular, the invention relates to a use, wherein the compound is selected from bis(8-quinolinyl)amine and 2,2'-(2,2-propanediyl)-bis-(8-hydroxyquinoline), these compounds having no mutagenic or bactericidal effect, in particular according to the adapted Ames test of D. M. Maron and B. N. Ames, *Mutat. Res.* 1983, 113, 173-215; D. E. Levin et al., *Mutat. Res.* 1982, 94, 315-330; D. E. Levin et al. *Proc. Natl. USA* 1982, 79, 7445-7449, in particular on TA98 and/or TA100 *Salmonella* strains in the absence or presence of enzymatic homogenate (S9) of rat liver microsomes.

According to another subject-matter, the present application relates to pharmaceutical compositions comprising a compound of formula (I)

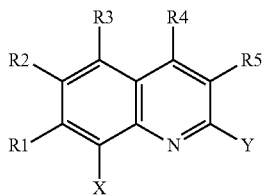

(I)

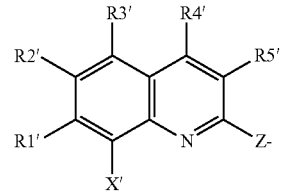

wherein in formula (I)

X represents an —OR, —NRR', —S(O)$_p$R or —OCOOR group and

Y represents a group of formula:

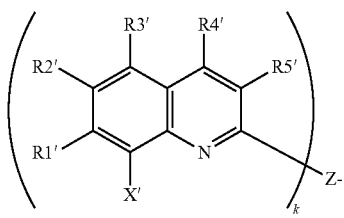

(IY)

in which X' represents an —OR, —NRR', S(O)$_p$R, —OCOOR group and

Z represents a group of formula -(A)$_m$-(Alk)$_n$-(A')$_{m'}$-(Alk')$_{n'}$-(A'')$_{m''}$-(Alk'')$_{n''}$, where m, n, m', n', m'' and n'' are the same or different and independently represent 0 or 1, it being understood that at least one of m, n, m', n' m'' and n'' is equal to 1, A, A' and A'' are the same or different and independently represent a group selected from —NR—, —S(O)$_p$—, —O— and —C(=O)—, or a 4-11 membered ring selected from cycloalkyls, heterocycles, aryls and heteroaryls, said ring being optionally substituted by one or more substituents selected from alkyl, OR, NRR', CF$_3$, Hal, CN, S(O)$_p$R, COOR, OCOOR, CONRR' and NRCOOR';

Alk, Alk' and Alk'' are the same or different and independently represent an -alkyl-group, optionally substituted by one or more substituents selected from OR, NRR', CF$_3$, Hal, CN, S(O)$_p$R, COOR, OCOOR, CONRR' and NRCOOR'; and R and R' are the same or different and independently represent a hydrogen atom or a cycloalkyl or alkyl group, optionally substituted by one or more groups selected from OR, NRR', Hal, —CN, —CF$_3$, S(O)$_p$R, COOR, OCOOR, CONRR' and NRCOOR'; heteroaryl;

R1, R2, R3, R4, R5, R1', R2', R3', R4', R5' and R6' are the same or different and independently represent a group or atom selected from H, OR, NRR', Hal, —CN, —CF$_3$ and alkyl optionally substituted by one or more substituents selected from OR, NRR', CF$_3$, Hal, CN, S(O)$_p$R, COOR, OCOOR, CONRR' and NRCOOR';

k represents 1 or 2;

p represents 0, 1 or 2;

as well as the pharmaceutically acceptable stereoisomers or mixtures, tautomeric forms, hydrates, solvates, salts, free forms and esters thereof, with the exception of compounds for which:

X represents an —OH group, and

Y represents a group of formula:

in which X' represents an —OH group, and

Z represents a group selected from —NH—, —NBu-, —NMe-,

R1, R2, R3, R4, R5, R1', R2', R3', R4', R5' and R6' are equal to H.

More preferably, compounds for pharmaceutical compositions according to the invention are selected from:

dimethyl-bis[8-(acetyloxy)-2-quinoline]propanedioate
2,2'-methanediyl-bis(8-hydroxyquinoline)
2,2'-methanediyl-bis(5-chloro-8-hydroxyquinoline)
2,2'-(2,2-propanediyl)-bis(8-hydroxyquinoline)
2,2'-(2,2-propanediyl)-bis(5-chloro-8-hydroxyquinoline)
2,2'-(difluoromethanediyl)-bis(8-hydroxyquinoline)
bis(8-hydroxy-2-quinolinyl)methanone
2,2'-(1,2-ethanediyl)-bis[8-(methyloxy)quinoline]
2,2'-(1,2-ethanediyl)-bis(8-hydroxyquinoline)
2,2'-(1,2-ethanediyl)-bis(5-chloro-8-hydroxyquinoline)
2,2'-(1,2-ethanediyl)-bis(5-chloro-7-iodo-8-hydroxyquinoline)
2,2'-(1,4-butanediyl)-bis[8-(methyloxy)quinoline]
2,2'-(1,4-butanediyl)-bis(8-hydroxyquinoline)
2,2',2''-(1,2,3-propanetriol)-tris[8-(methyloxy)quinoline]
2,2',2''-(1,2,3-propanetriol)-tris(8-hydroxyquinoline)
dimethyl bis{7-(methyloxy)8-[phenylmethyl)oxy]-2-quinolinyl}propanedioate
2,2'-(methanediyl)-bis(7-methyloxy-8-hydroxyquinolinium)dichloride
2,2'-(1,2-ethanediyl)-bis[7-(methyloxy)-8-quinolinol]
8-hydroxy-N-(8-hydroxy-2-quinolinyl)-2-quinoline carboxamide
2-{[8-hydroxy-2-quinolinyl)amino]methyl}-8-quinolinol
2,2'-(iminodimethanediyl)di(N-boc-8-quinoline amine)
2,2'-(iminodimethanediyl)di(8-quinoline amine)
2,2',2''-(nitrilotrimethanediyl)tri(N-boc-8-quinoline amine)
2,2',2''-(nitrilotrimethanediyl)tri(8-quinoline amine)
2,2'-[(butylimino)dimethanediyl]di(N-boc-8-quinoline amine)
2,2'-[(butylimino)dimethanediyl]di(8-quinoline amine)
N-butyl-2,2'-imino-bis(8-quinoline amine)

as well as the pharmaceutically acceptable stereoisomers or mixtures, tautomeric forms, hydrates, solvates, salts, free forms and esters thereof.

According to another subject-matter, the present invention relates to the compounds of formula (I):

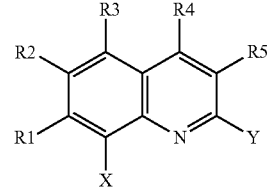

(I)

wherein in formula (I)
X represents an —OR, —NRR', —S(O)$_p$R, —OCOOR or —NO$_2$ group and
Y represents a group of formula:

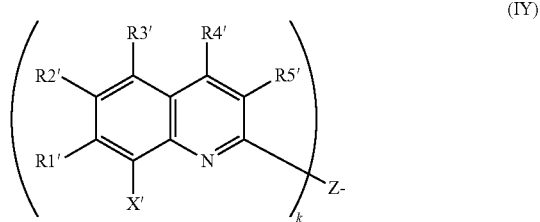

in which X' represents an —OR, —NRR', —S(O)$_p$R, —OCOOR or —NO$_2$ group and
Z represents a group of formula -(A)$_m$-(Alk)$_n$-(A')$_{m'}$-(Alk')$_{n'}$-(A")$_{m''}$-(Alk")$_{n''}$, where m, n, m', n', m" and n" are the same or different and independently represent 0 or 1, it being understood that at least one of m, n, m', n' m" and n" is equal to 1,
A, A' and A" are the same or different and independently represent a group selected from —NR—, —S(O)$_p$—, —O— and —C(=O)—, or a 4-11 membered ring selected from cycloalkyls, heterocycles, aryls and heteroaryls, said ring being optionally substituted by one or more substituents selected from alkyl, OR, NRR', CF$_3$, Hal, CN, S(O)$_p$R, COOR, OCOOR, CONRR' and NRCOOR';
Alk, Alk' and Alk" are the same or different and independently represent an -alkyl-group optionally substituted by one or more substituents selected from OR, NRR', CF$_3$, Hal, CN, S(O)$_p$R, COOR, OCOOR, CONRR' and NRCOOR'; and
R and R' are the same or different and independently represent a hydrogen atom or a cycloalkyl or alkyl group, optionally substituted by one or more groups selected from OR, NRR', Hal, —CN, —CF$_3$, S(O)$_p$R, COOR, OCOOR, CONRR' and NRCOOR'; heteroaryl;
R1, R2, R3, R4, R5, R1', R2', R3, R4', R5' and R6' are the same or different and independently represent a group or atom selected from H, OR, NRR', Hal, —CN, —CF$_3$ and alkyl optionally substituted by one or more substituents selected from OR, NRR', CF$_3$, Hal, CN, S(O)$_p$R, COOR, OCOOR, CONRR' and NRCOOR';
k represents 1 or 2;
p represents 0, 1 or 2;
as well as the pharmaceutically acceptable stereoisomers or mixtures, tautomeric forms, hydrates, solvates, salts, free forms and esters thereof,
with the exception of compounds for which:
X represents an —OH group, and
Y represents a group of formula:

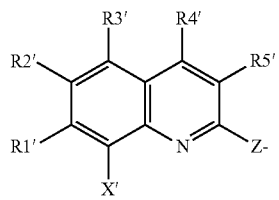

in which X' represents an —OH group, and
Z represents a group selected from —CH$_2$—, —CH$_2$—CH$_2$—, —(CH$_2$)$_6$—, —CH=CH—, —C(Me)$_2$-, -thienyl-, —CH$_2$—S—CH$_2$—, —NH—, —NBu-, —NMe-,
R1, R2, R3, R4, R5, R1', R2', R3', R4', R5' and R6' are equal to H.

More preferably, compounds according to the present invention are selected from:
2,2'-methanediyl-bis(5-chloro-8-hydroxyquinoline)
2,2'-(2,2-propanediyl)-bis(5-chloro-8-hydroxyquinoline)
2,2'-(difluoromethanediyl)-bis(8-hydroxyquinoline)
bis(8-hydroxy-2-quinolinyl)methanone
2,2'-(1,2-ethanediyl)-bis(5-chloro-8-hydroxyquinoline)
2,2'-(1,2-ethanediyl)-bis(5-chloro-7-iodo-8-hydroxyquinoline)
2,2'-(1,4-butanediyl)-bis[8-(methyloxy)quinoline]
2,2'-(1,4-butanediyl)-bis(8-hydroxyquinoline)
2,2',2"-(1,2,3-propanetriol)-tris[8-(methyloxy)quinoline]
2,2',2"-(1,2,3-propanetriol)-tris(8-hydroxyquinoline)
dimethyl bis{7-(methyloxy)8-[phenylmethyl)oxy]-2-quinolinyl}propanedioate
2,2'-(methanediyl)-bis(7-methyloxy-8-hydroxy-2-quinolinium)dichloride
2,2'-(1,2-ethanediyl)-bis[7-(methyloxy)-8-quinolinol]
8-hydroxy-N-(8-hydroxy-2-quinolinyl)-2-quinoline carboxamide
2-{[8-hydroxy-2-quinolinyl)amino]methyl}-8-quinolinol
2,2'-(iminodimethanediyl)di(N-boc-8-quinoline amine)
2,2'-(iminodimethanediyl)di(8-quinoline amine)
2,2',2"-(nitrilotrimethanediyl)tri(N-boc-8-quinoline amine)
2,2',2"-(nitrilotrimethanediyl)tri(8-quinoline amine)
2,2'-[(butylimino)dimethanediyl]di(N-boc-8-quinoline amine)
2,2'-[(butylimino)dimethanediyl]di(8-quinoline amine)
N-butyl-2,2'-imino-bis(8-quinoline amine)
N-butyl-2,2'-imino-bis(8-quinoline amine)
as well as the pharmaceutically acceptable stereoisomers or mixtures, tautomeric forms, hydrates, solvates, salts, free forms and esters thereof.

Preferably, X represents OR and Y represents a group of formula (IY), in which X' represents OR and Z represents A, where A represents —C(O)— or Z represents Alk, where Alk represents a linear or branched alkyl group optionally substituted by one or more halogen atoms; or
X represents OR and Y represents a group of formula (IY), in which X' represents OR and Z represents A-A', where A represents —C(O)— and A' represents NR'; or
X represents OR and Y represents a group of formula (IY), in which X' represents OR and Z represents A-Alk, where A represents NR' and Alk represents a linear or branched alkyl group optionally substituted by one or more halogen atoms; or
X represents NRR' and Y represents a group of formula (IY), in which X' represents NRR' and Z represents Alk-NR"-Alk, where Alk represents a linear or branched alkyl group optionally substituted by one or more halogen atoms; or
X represents NRR' and Y represents a group of formula (IY), in which X' represents NRR' and Z represents NR"; or
X represents a group of formula (IX), in which Z represents —NR—, —NR-Alk-NR—, —O—, —NR—C(O)— or —NR—S(O)$_2$— and Y represents H;
k=1 or 2
R=H or COOR' or alkyl, optionally substituted, R'=H or alkyl, optionally substituted, R"=H, alkyl or heteroaryl, optionally substituted, and
R1, R2, R3, R4, R5, R1', R2', R3, R4', R5' and R6' are the same or different and independently represents a group or atom selected from H, OR, NRR', Hal, —CN, —CF$_3$, and alkyl optionally substituted by one or more substituents selected from OR, NRR', CF$_3$, Hal, CN, S(O)$_p$R, COOR, OCOOR, CONRR' and NRCOOR' as well as the pharmaceutically acceptable stereoisomers or mixtures, tautomeric forms, hydrates, solvates, salts, free forms and esters thereof.

Hereinbefore and hereinafter, it is understood in the definition of m, m', m'', n, n' and n'' that if m=m'=1 or m'=m''=1 or m=m'=m''=1 or m=m''=1 and m'=0, then n=1 or n'=1 or n=n'=1 or at least n or n'=1 respectively.

According to the present invention, the alkyl radicals are straight chain or branched saturated hydrocarbon radicals, containing from 1 to 20 carbon atoms, preferably from 1 to 5 carbon atoms.

The methyl, ethyl, propyl, butyl, pentyl, hexyl, octyl, nonyl, decyl, dodecyl, hexadecyl and octadecyl radicals can be mentioned in particular as linear radicals.

The isopropyl, tert-butyl, 2-ethylhexyl, 2-methylbutyl, 2-methylpentyl, 1-methylpentyl and 3-methylheptyl radicals can be mentioned in particular as branched radicals or radicals substituted by one or more alkyl radicals.

Alkoxy radicals according to the present invention are radicals of formula —O-alkyl, the alkyl being as defined hereinbefore.

Fluorine, chlorine, bromine and iodine atoms are mentioned in particular as halogen atoms The alkenyl radicals are straight chain or linear hydrocarbon radicals, and comprise one or more ethylenically unsaturated bonds. Suitable alkenyl radicals include, in particular the allyl or vinyl radicals.

The alkynyl radicals are straight chain or linear hydrocarbon radicals, and comprise one or more acetylenically unsaturated bonds. Suitable alkynyl radicals, include, in particular, acetylene.

The cycloalkyl radical is a non-aromatic, saturated or partially unsaturated monocyclic, bicyclic or tricyclic hydrocarbon radical containing from 3 to 11 carbon atoms, such as, in particular, cyclopropyl, cyclopentyl, cyclohexyl or adamantyl, as well as the corresponding rings containing one or more unsaturated bonds.

The term "aryl" denotes a monocyclic or bicyclic hydrocarbon aromatic system containing from 4 to 11 carbon atoms.

Suitable aryl radicals include in particular the phenyl or naphthyl radical, more particularly substituted by at least one halogen atom.

Suitable alkylaryl radicals include in particular the benzyl or phenethyl radical.

Heteroaryl radicals denote aromatic systems comprising one or more heteroatoms selected from nitrogen, oxygen or sulphur, mono- or bicyclic, which contain from 4 to 11 carbon atoms. Suitable heteroaryl radicals include pyrazinyl, thienyl, oxazolyl, furazanyl, pyrrolyl, 1,2,4-thiadiazolyl, naphthyridinyl, pyridazinyl, quinoxalinyl, phthalazinyl, imidazo[1,2-a]pyridine, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzoazaindole, 1,2,4-triazinyl, benzothiazolyl, furanyl, imidazolyl, indolyl, triazolyl, tetrazolyl, indolizinyl, isoxazolyl, isoquinolinyl, isothiazolyl, oxadiazolyl, pyrazinyl, pyridazinyl, pyrazolyl, pyridyl, pyrimidinyl, purinyl, quinazolinyl, quinolinyl, isoquinolinyl, 1,3,4-thiadiazolyl, thiazolyl, triazinyl, isothiazolonyl, or carbazolyl, as well as the corresponding groups resulting from fusion thereof or fusion with the phenyl ring.

The term "pharmaceutically acceptable salts" refers to the relatively non-toxic, inorganic and organic acid addition salts and base addition salts of compounds of the present invention. These salts can be prepared in situ during final isolation and purification of the compounds. In particular, acid addition salts can be prepared by separately reacting the purified compound in its refined form with an organic or inorganic acid and isolating the resultant salt. Examples of acid addition salts include hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptanate, lacto-bionate, sulfamates, malonates, salicylates, propionates, methylenebis-beta-hydroxynaphthoates, gentisic acid, isethionates, di-p-toluoyl-tartrates, methanesulfonates, ethanesulfonates, benzenesulfonates, p-toluenesulfonates, cyclohexyl sulfamates and quinateslaurylsulfonate salts, and the like. (For example, see S. M. Berge et al. *Pharmaceutical Salts, J. Pharm. Sci,* 66: p. 1-19 (1977), which is included herein by reference.) Acid addition salts can also be prepared by separately reacting the purified compound in its acid form with an organic or inorganic base and isolating the resultant salt. Acid addition salts include amine and metal salts. Suitable metal salts include sodium, potassium, calcium, barium, zinc, magnesium and aluminium salts. Sodium and potassium salts are preferred. Suitable inorganic addition base salts are prepared from metal bases which include sodium hydride, sodium hydroxide, potassium hydroxide, calcium hydroxide, aluminium hydroxide, lithium hydroxide, magnesium hydroxide, zinc hydroxide. Suitable base amine addition salts are prepared from amines which are sufficiently alkaline to form a stable salt, and preferably include amines which are often used in medicinal chemistry because of their low toxicity and suitability for medical use: ammonia, ethylenediamine, N-methyl-glucamine, lysine, arginine, ornithine, choline, N,N'-dibenzylethylenediamine, chloroprocaine, diethanolamine, procaine, N-benzyl-phenethylamine, diethylamine, piperazine, tris(hydroxymethyl)-aminomethane, tetramethylammonium hydroxide, triethylamine, dibenzylamine, ephenamine, dehydroabiethylamine, N-ethylpiperidine, benzylamine, tetramethylammonium, tetraethylammonium, methylamine, dimethylamine, trimethylamine, ethylamine, basic amine acids, for example lysine and arginine, and dicyclohexylamine and the like.

The invention also relates to pharmaceutically suitable stereoisomers or mixtures thereof, tautomeric forms, hydrates, solvates, salts and esters of compounds of formula (I).

Compounds of the invention of formula (I), as defined hereinbefore, having a sufficiently acidic group or a sufficiently basic group, or both, can include the corresponding pharmaceutically acceptable organic or inorganic acid, or organic or inorganic base salts.

According to a further subject, the present invention also relates to the process for preparing compounds of formula (I).

In the following embodiments and examples, group R6 represents group Y.

According to a first aspect, the compounds of formula (I) are prepared by coupling compounds of formulae (II) and (II'):

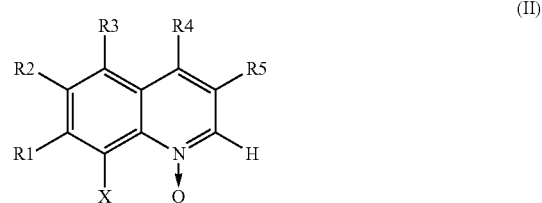

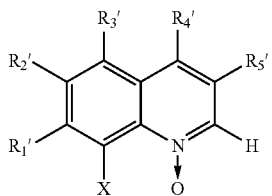
(II')

followed by hydrolysis, and optionally followed by derivatisation or derivatisations of the product of formula (I) obtained in order to acquire the desired product of formula (I).

This reaction is generally carried out using dimethyl-malonate, in the presence of acetic anhydride. This process is illustrated by diagram 1.

The hydrolysis reaction is carried out generally using an acid, such as, for example, hydrochloric acid, or any other suitable acid.

According to a second aspect, the compounds of formula (I) are prepared by coupling compounds of formulae (III) and (III'):

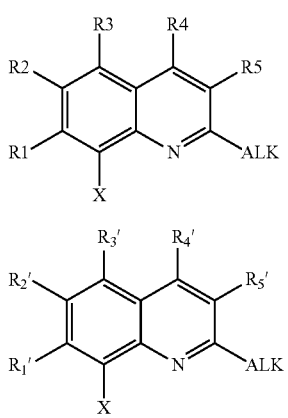
(III)
(III')

optionally followed by derivatisation or derivatisations of the product of formula (I) obtained in order to acquire the desired product of formula (I).

Generally, this reaction is carried out using a base such as lithium diisopropylamine (LDA), followed by the addition of a compound of formula Hal-Z'-Hal, in which Z' is selected so as to obtain the corresponding group Z in general formula (I).

This process is illustrated in diagram 2.

Preferably, when K=2, it is preferable to start with (III) and (III'), by means of a base such as lithium diisopropylamine (LDA), followed by the addition of CuCl₂ and treatment with EDTA. This process is illustrated in diagram 5.

According to a third aspect, the compounds of formula (I) are prepared by coupling compounds of formulae (IV) and (IV'):

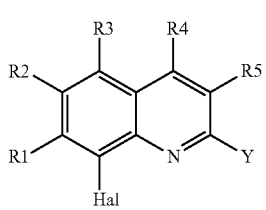
(IV)

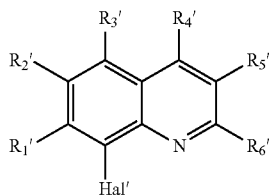
(IV')

in which Hal and Hal' represent halogen atoms in the presence of a group of formula HZH, optionally followed by derivatisation or derivatisations of the product of formula (I) obtained in order to acquire the desired product of formula (I).

Generally, this reaction is carried out in the presence of a catalyst such as tris(dibenzylideneacetone)dipalladium(0) and rac-2,2'-bis(diphenylphosphino)-1,1'-binaphthyl.

This process is illustrated in diagram 6.

According to a fourth aspect, the compounds of formula (I) are prepared by coupling compounds of formulae (V) and (V'):

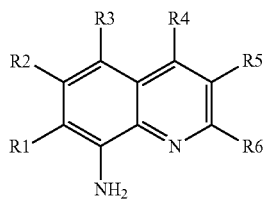
(V)

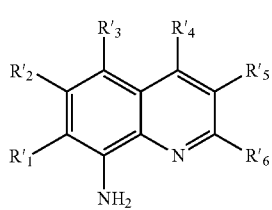
(V')

in the presence of a group of formula Hal-Z-Hal, in which Hal represents halogen atoms, optionally followed by derivatisation or derivatisations of the product of formula (I) obtained in order to acquire the desired product of formula (I).

Generally, this reaction is carried out using a base such as lithium diisopropylamine (LDA), followed by the addition of a compound of formula Hal-Z-Hal, in which Z is selected so as to obtain the corresponding group Z in general formula (I).

This process is illustrated in diagram 7.

According to a fifth aspect, the compounds of formula (I) are prepared by coupling compounds of formulae (VI) and (VI'):

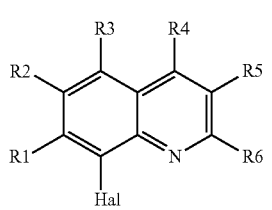
(VI)

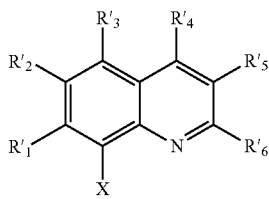

(VI')

in which Hal is a halogen atom in the presence of $CuCl_2$ and a base such as $Cs_2CO_3$, optionally followed by derivatisation or derivatisations of the product of formula (I) obtained in order to acquire the desired product of formula (I).

This process is illustrated in diagram 8.

According to a sixth aspect, the compounds of formula (I) are prepared by coupling compounds of formulae (VII) and (VII'):

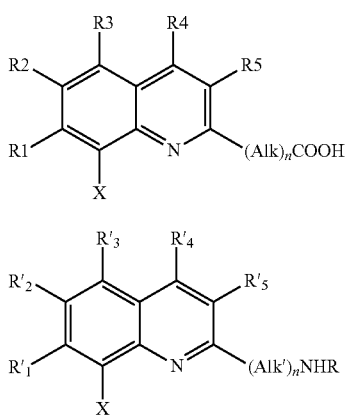

(VII)

(VII')

is optionally followed by derivatisation or derivatisations of the product of formula (I) obtained in order to acquire the desired product of formula (I).

Generally, this reaction is carried out in the presence of carboxylic acid energisers such as (benzotriazol-1-yloxy)tris(dimethylamino)phosphonium hexafluorophosphate combined with hydroxybenzotriazole in the presence of a base such as triethylamine.

This process is illustrated in diagram 11.

According to a seventh aspect, the compounds of formula (I) are prepared by coupling compounds of formulae (VIII) and (VIII'):

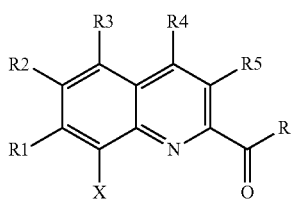

(VIII)

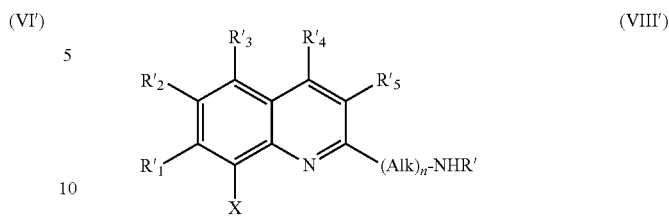

(VIII')

optionally followed by derivatisation or derivatisations of the product of formula (I) obtained in order to acquire the desired product of formula (I).

Generally, this reaction is carried out in the presence of an imine reducing agent such as $NaBHR_3$.

This process is illustrated in diagram 12.

According to an eighth aspect, the compounds of formula (I) are prepared by coupling compounds of formulae (VIII) and (VIII'):

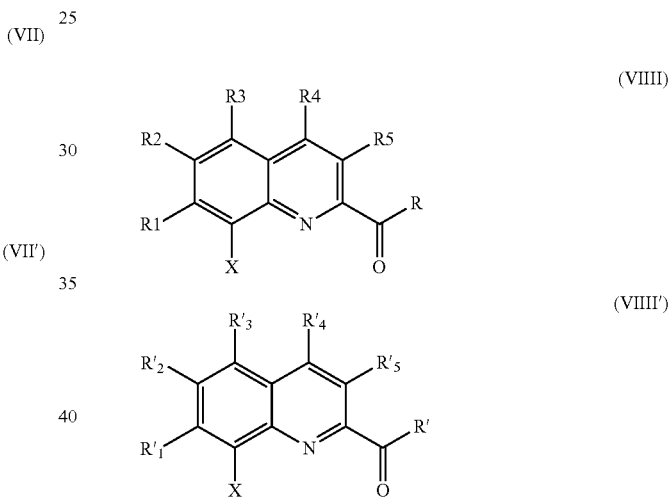

(VIIII)

(VIIII')

in the presence of a group of formula $R"NH_2$ optionally followed by derivatisation or derivatisations of the product of formula (I) obtained in order to acquire the desired product of formula (I).

Generally, this reaction is carried out in the presence of an imine reducing agent such as $NaBHR_3$.

This process is illustrated in diagram 13.

According to a ninth aspect, the compounds of formula (I) are prepared by coupling the compound of formula (VV) and two compounds of formula (VV'):

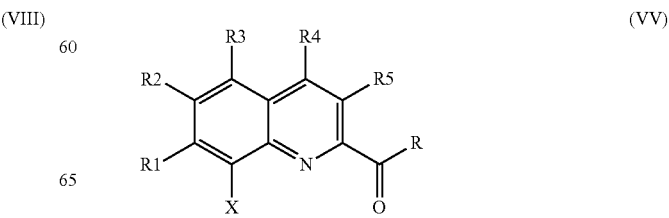

(VV)

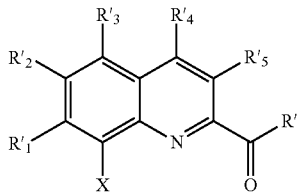
(VV')

in the presence of NH₃ optionally followed by derivatisation or derivatisations of the product of formula (I) obtained in order to acquire the desired product of formula (I).

Generally, this reaction is carried out in by means of an imine reducing agent such as NaBHR₃.

This process is illustrated in diagram 14.

According to a tenth aspect, the compounds of formula (I) are prepared by coupling compounds of formulae (VVI) and (VVI'):

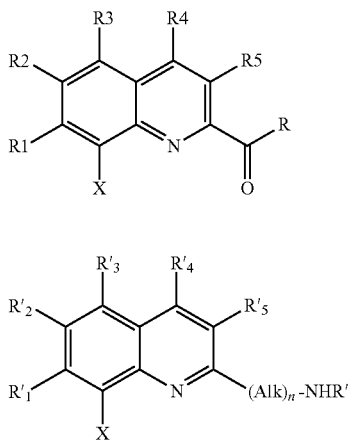

optionally followed by derivatisation or derivatisations of the product of formula (I) obtained in order to acquire the desired product of formula (I).

Generally, this reaction is carried out in the presence of an imine reducing agent such as NaBHR₃.

This process is illustrated in diagram 15.

According to an eleventh aspect, the compounds of formula (I) are prepared by coupling compounds of formulae (VVII) and (VVII'):

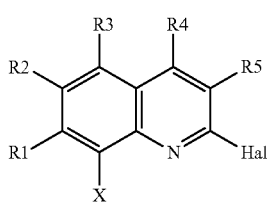

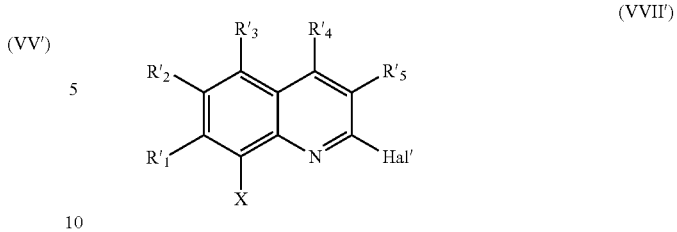

in which Hal and Hal' are halogen atoms in the presence of a group of formula RNH₂, optionally followed by derivatisation or derivatisations of the product of formula (I) obtained in order to acquire the desired product of formula (I).

Generally, this reaction is carried out by reacting (VVII) with RNH₂ then coupling it with (VVII') in the presence of a catalyst such as tris(dibenzylideneacetone)dipalladium(0) and rac-2,2'-bis(diphenylphosphino)-1,1'-binaphthyl.

This process is illustrated in diagram 16.

According to a twelfth aspect, the compounds of formula (I) are prepared by coupling compounds of formulae (VVIII) and (VVIII'):

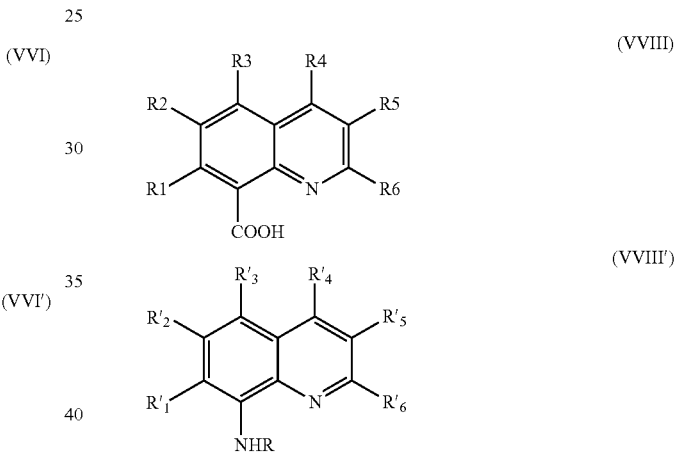

optionally followed by derivatisation or derivatisations of the product of formula (I) obtained in order to acquire the desired product of formula (I).

Generally, this reaction is carried out in the presence of carboxylic acid energisers such as (benzotriazol-1-yloxy)tris(dimethylamino)phosphonium hexafluorophosphate combined with hydroxybenzotriazole in the presence of a base such as triethylamine.

This process is illustrated in diagram 17.

The term "derivatisation" denotes any reaction which makes it possible to modify or introduce groups on the starting molecules. This may involve halogenation, alkylation, alkoxylation, addition, substitution, protection, deprotection, reduction, etc. These reactions are generally known per se. In the process according to the invention, these reactions can be carried out by applying or adapting these methods.

Representative examples of these derivatisation reactions are illustrated in diagrams 1, 3, 4, 9, 10, 13, 14, 15 and 16.

Thus, the compounds of general formula (I) can be prepared by applying or adapting any method known per se by and/or in the scope of a person skilled in the art, particularly those described by Larock in *Comprehensive Organic Transformations*, VCH Pub., 1989, or by applying or adapting the processes described in the following examples.

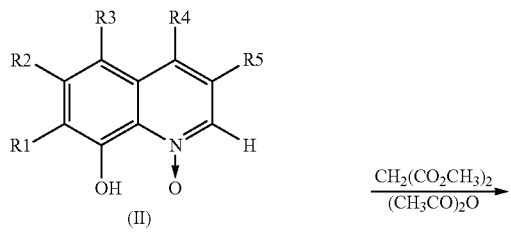
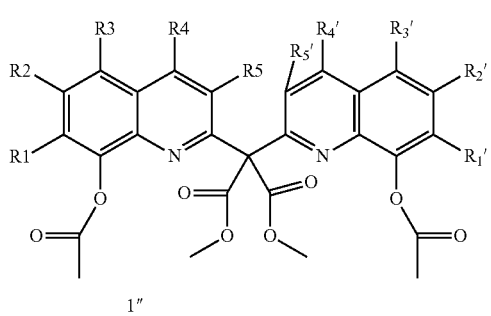
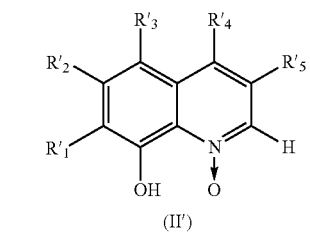
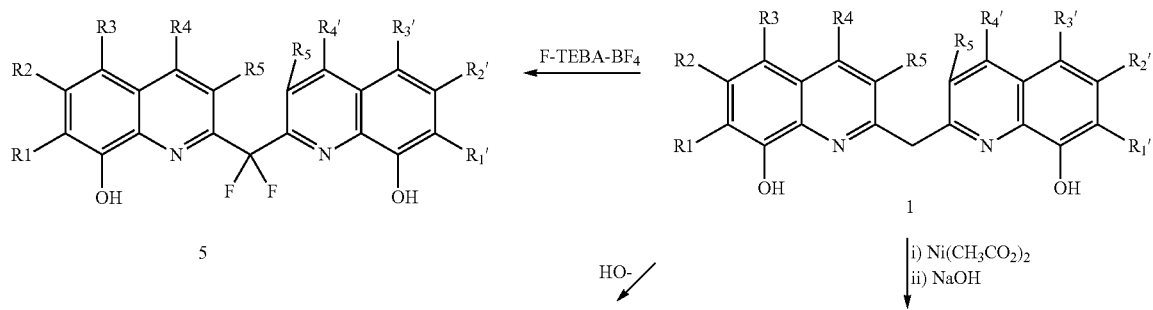
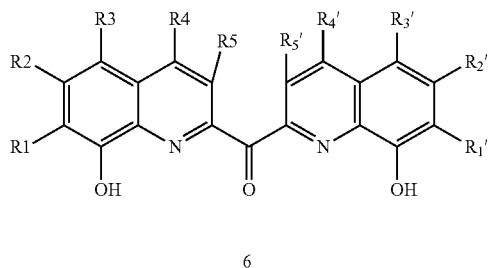
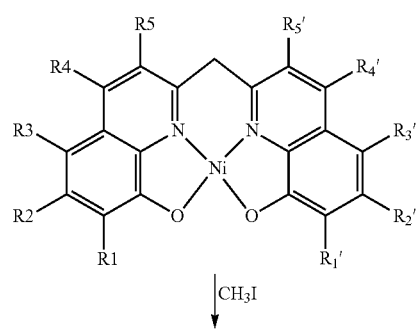
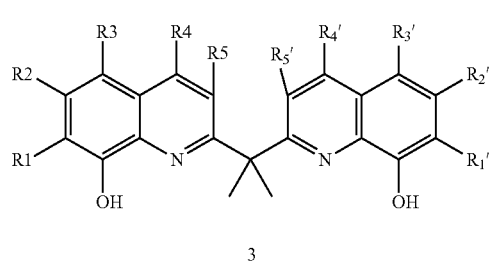
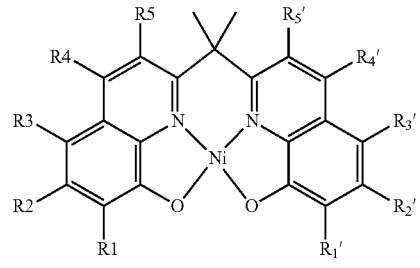

Diagram 1

Synthesis of 1, 1″ and the Derivatives Thereof: 3, 5, 6, and Analogues

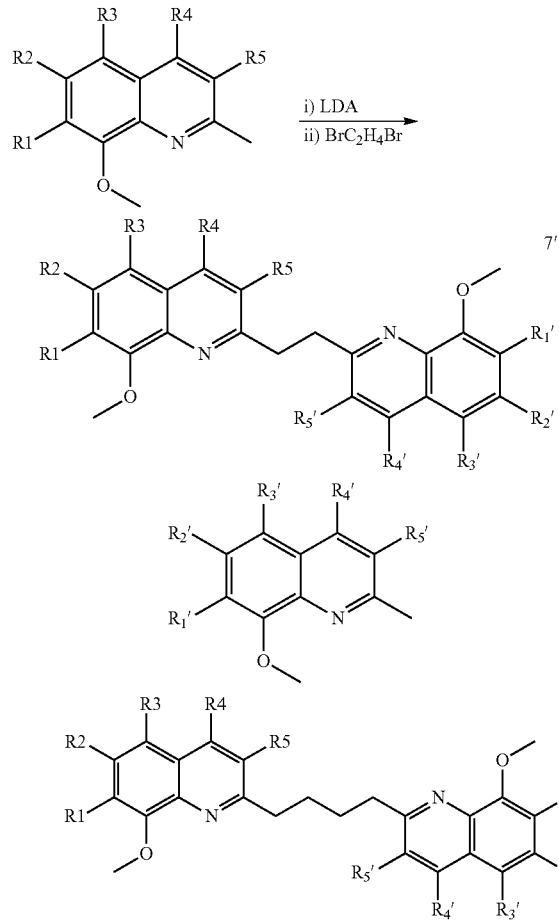

Diagram 2

Synthesis of 2,2′-(1,2-ethanediyl)-bis[8-(methyloxy)quinoline] and 2,2′(1,4-butanediyl)-bis[8-(methyloxy)quinoline] (7′), (10′) and Analogues Thereof

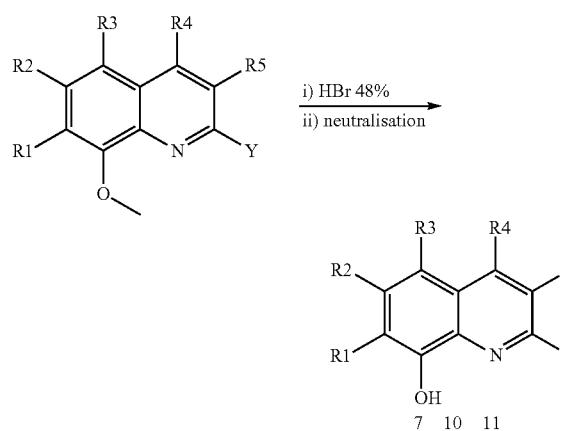

7  10  11

Diagram 3

Hydrolysis of Methyloxy Protecting Groups for Synthesising 7, 10, 11 and the Analogues Thereof

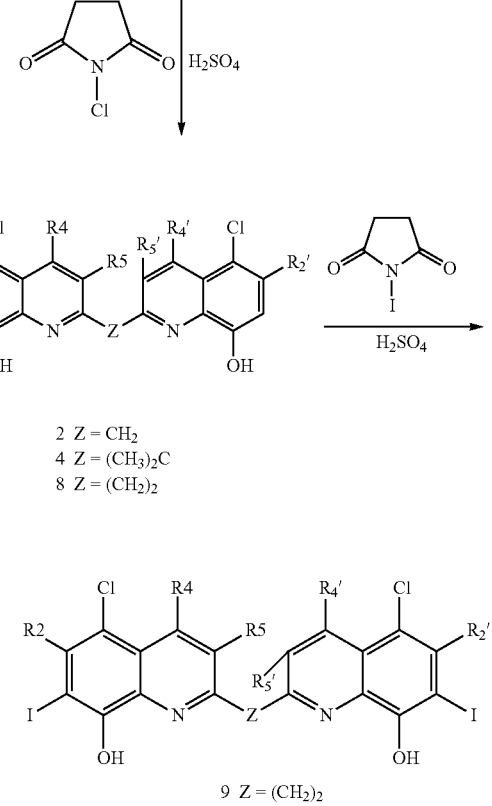

2  Z = $CH_2$
4  Z = $(CH_3)_2C$
8  Z = $(CH_2)_2$

9  Z = $(CH_2)_2$

Diagram 4

Halogenation Reaction for Preparing 2, 4, 8, 9 and the Analogues Thereof

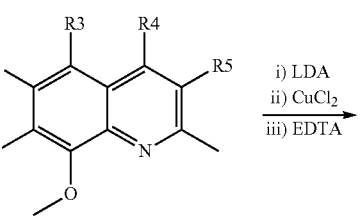

Diagram 5
Synthesis of 2,2′,2″-(1,2,3-propanetriol)-tris[8-(methyloxy)quinoline] (11′) and the Analogues Thereof
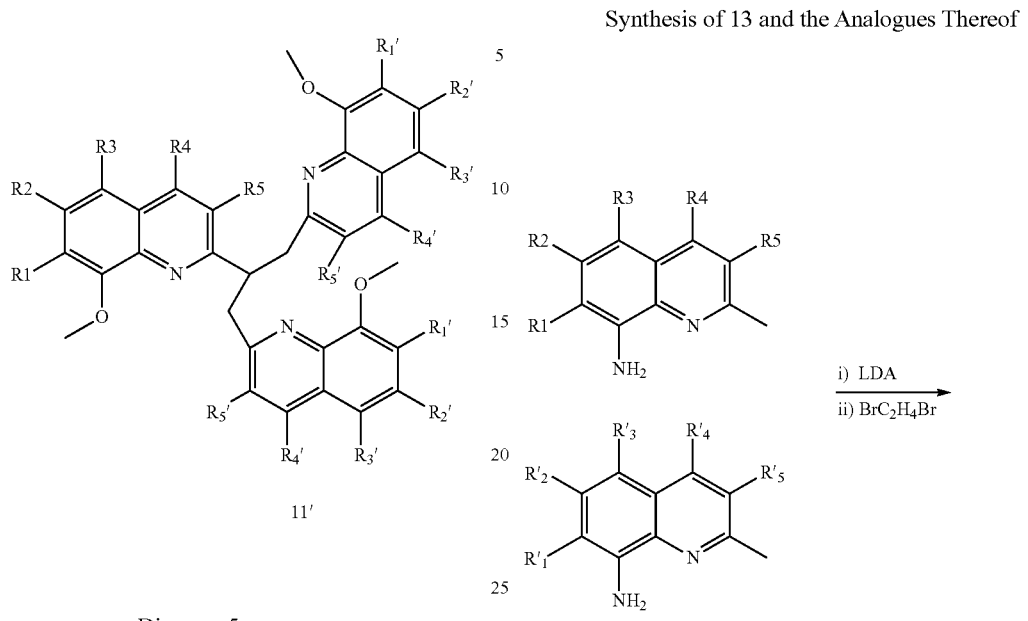
Diagram 6
Synthesis of 13 and the Analogues Thereof
Diagram 7
Synthesis of 14 and the Analogues Thereof
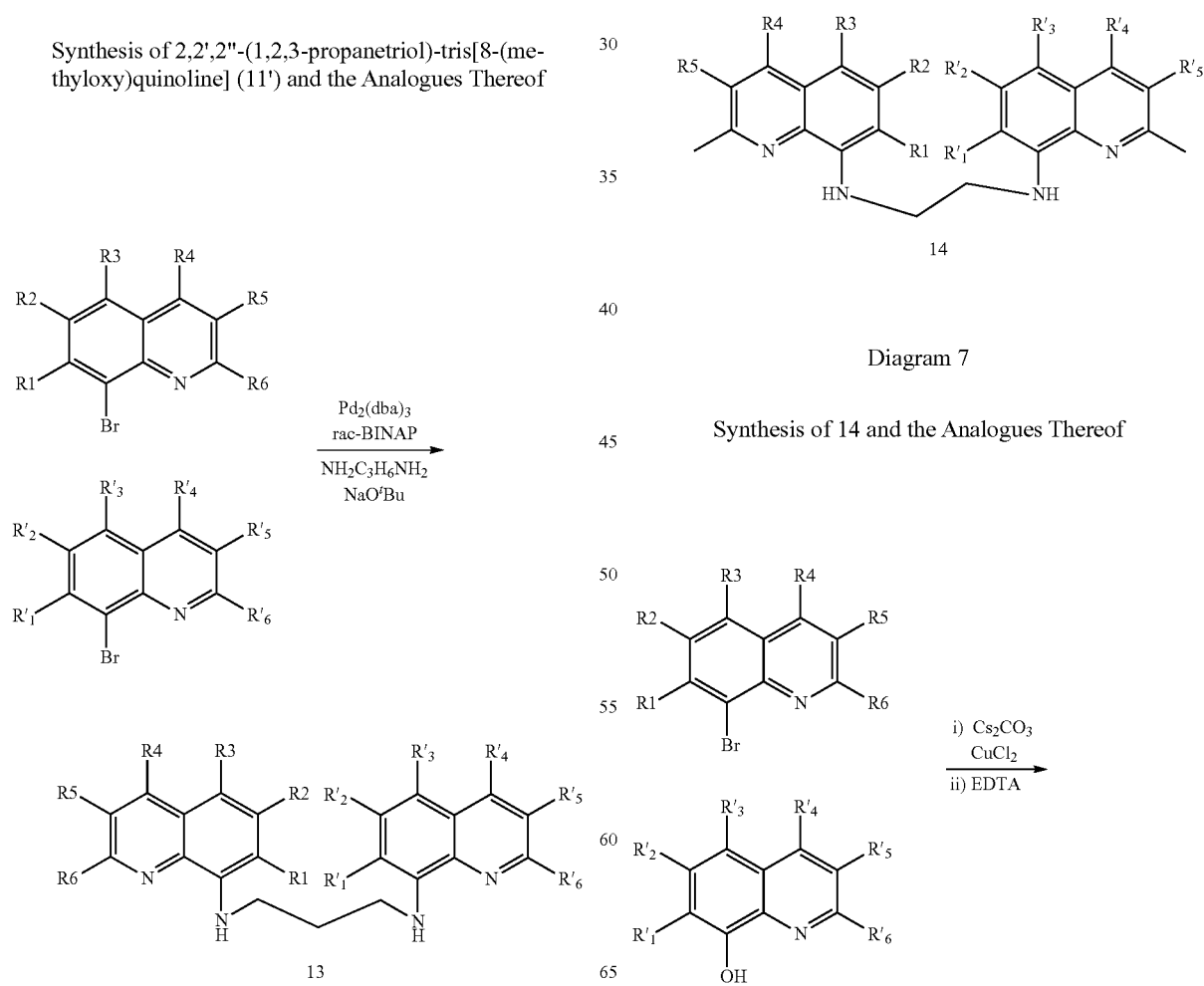

27
-continued
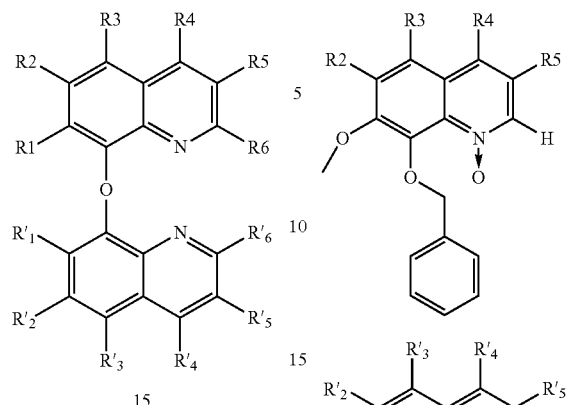
Diagram 8
Synthesis of 15 and the Analogues Thereof
28
-continued
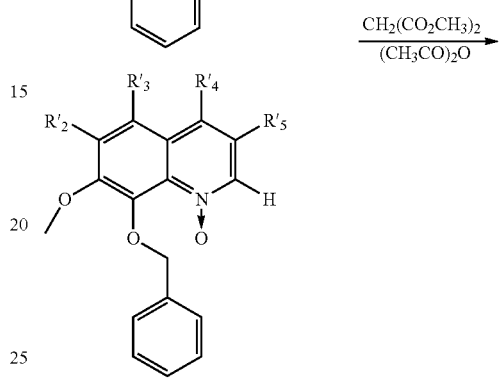
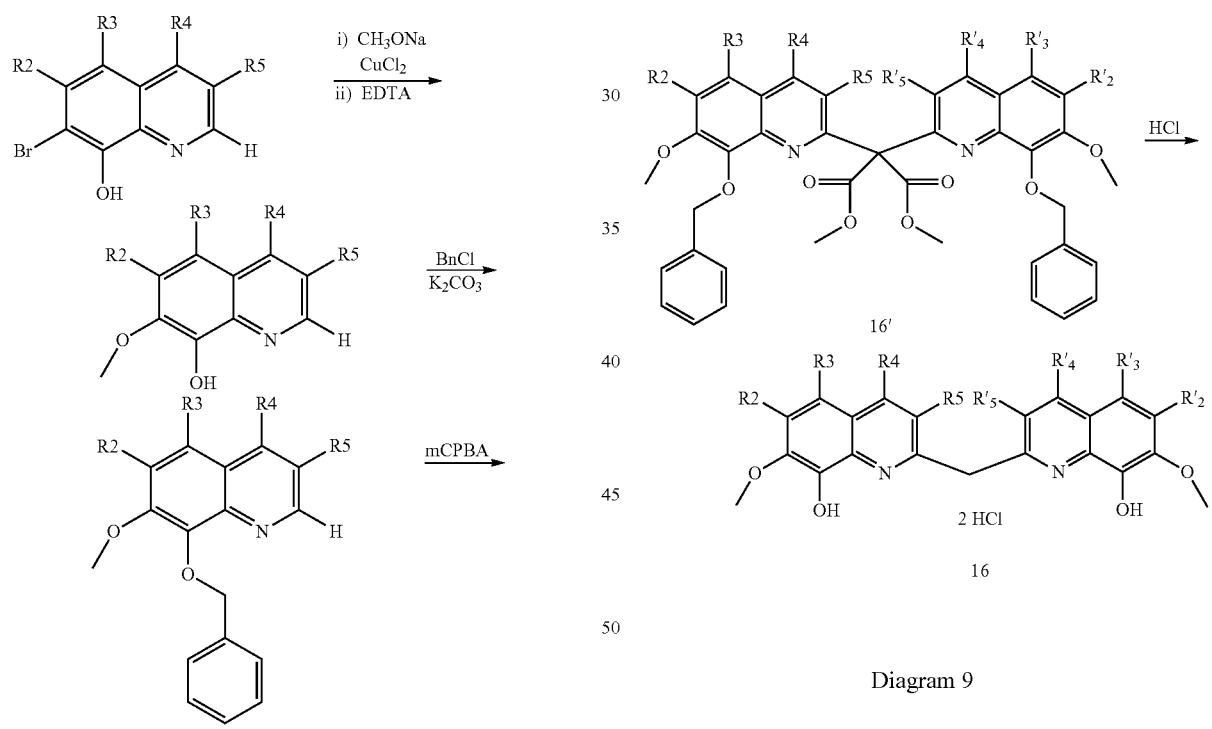
Diagram 9
Synthesis of 16', 16 and the Analogues Thereof
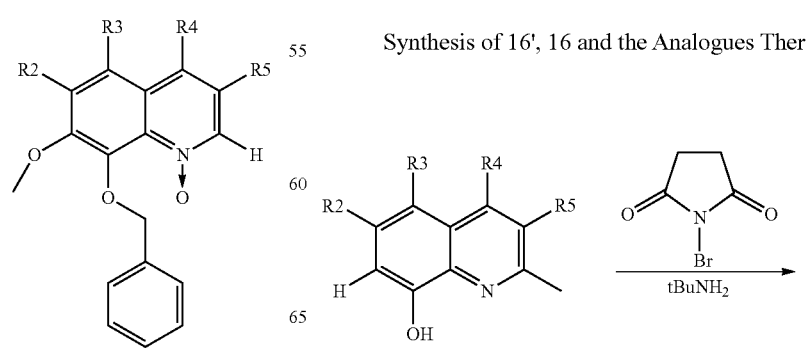

Diagram 11
Synthesis of 18 and the Analogues Thereof
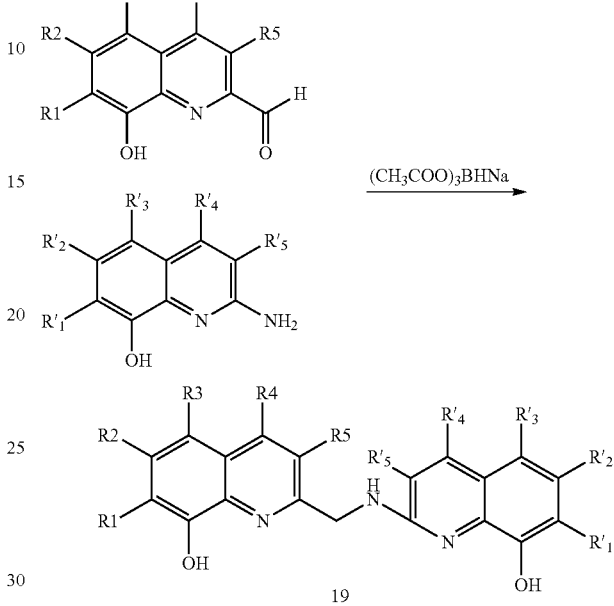
Diagram 12
Synthesis of 19 and the Analogues Thereof
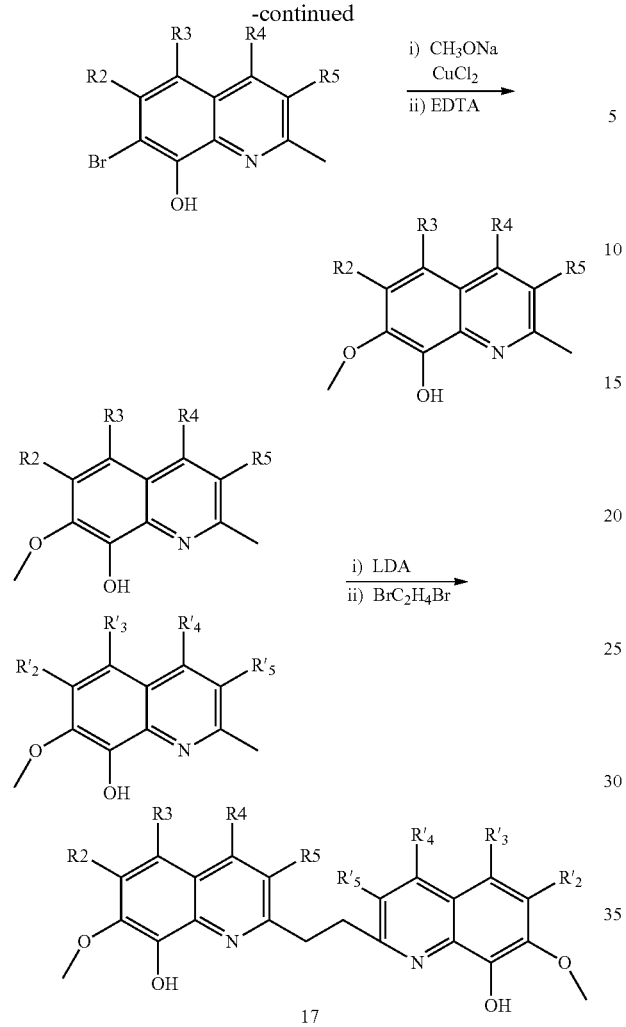
Diagram 10
Synthesis of 17 and the Analogues Thereof
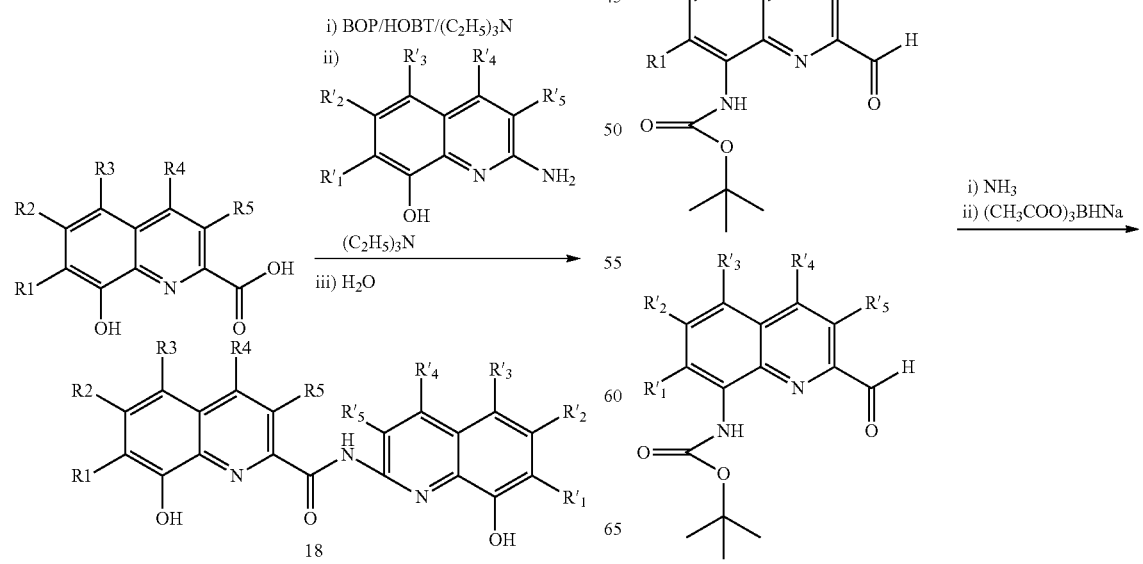

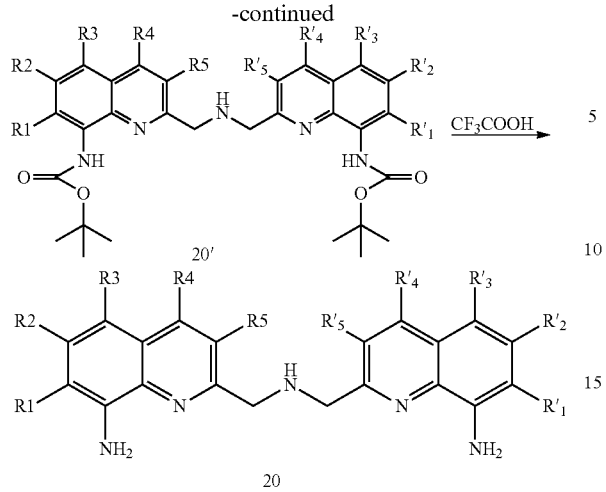
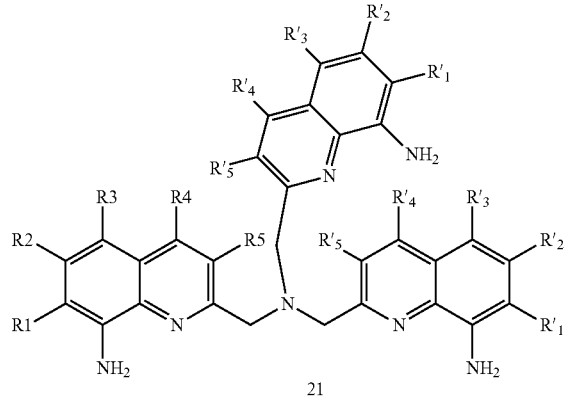
Diagram 13
Synthesis of 20', 20 and the Analogues Thereof
Diagram 14
Synthesis of 21', 21 and the Analogues Thereof
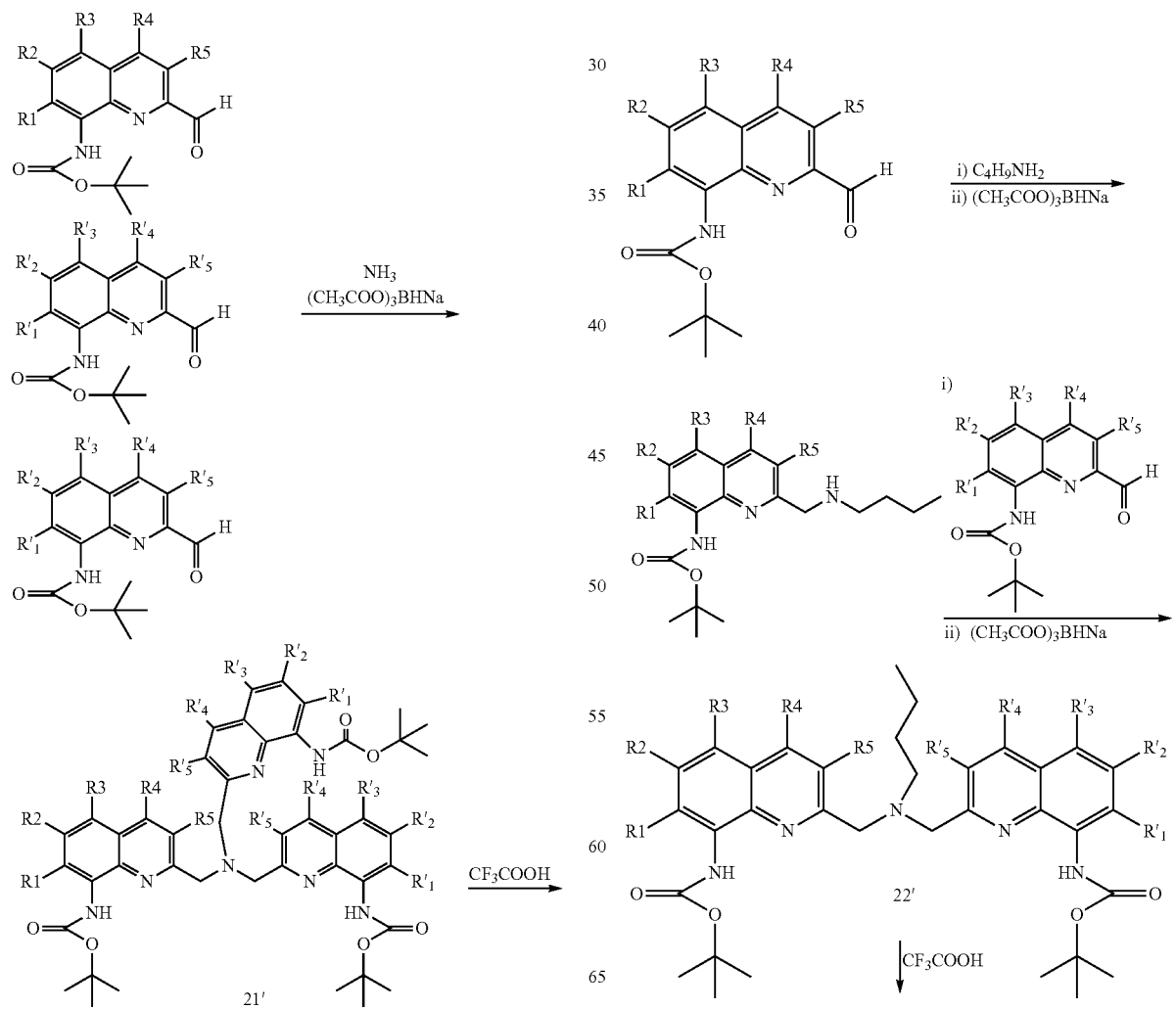

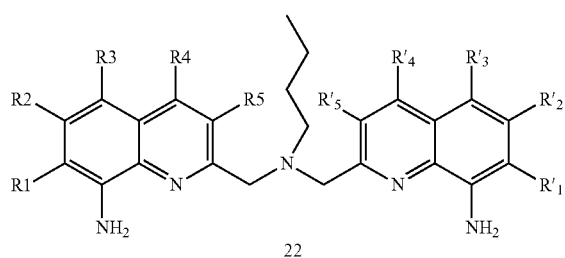
22
Diagram 15
Synthesis of 22', 22 and the Analogues Thereof
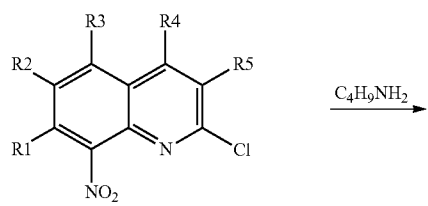
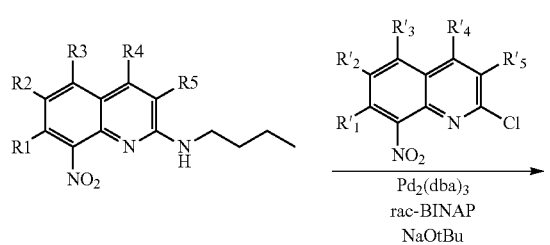
23'
↓
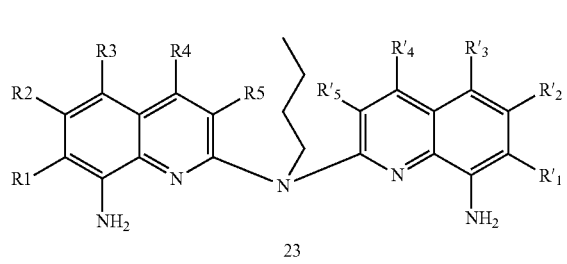
23
Diagram 16
Synthesis of 23', 23 and the Analogues Thereof
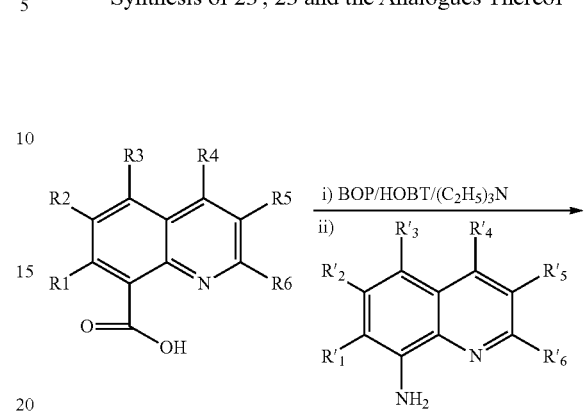
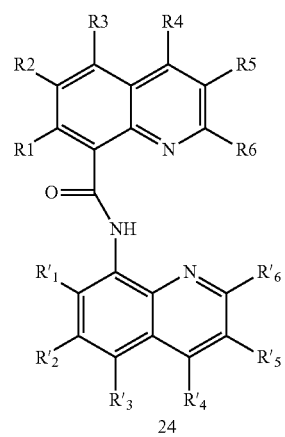
24
Diagram 17
Synthesis of 24 and the Analogues Thereof
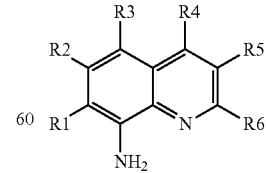
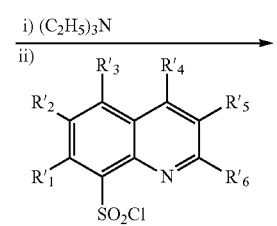

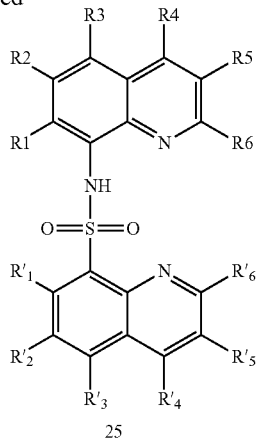

Diagram 18

Synthesis of 25 and the Analogues Thereof

Reaction intermediates are commercially available or can be prepared by a person skilled in the art by applying or adapting methods known per se.

The process according to the invention can also include the subsequent stage of isolation of the products of formula (I) obtained.

In the reactions described herein, it may be necessary to protect the reactive functional groups, for example the hydroxy, amino, imino, thio and carboxy groups if they are desired in the final product, so as to avoid undesirable participation thereof in the reactions. Traditional protecting groups can be used in accordance with the standard practice. For examples, see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

The compound thus prepared can be recovered from the reaction mixture by traditional means. For example, compounds can be recovered by distilling the solvent from the reaction mixture or, if necessary, after distilling the solvent from the solution, by pouring the remainder into water, then extracting with a water-immiscible organic solvent, and distilling the solvent from the extract. Furthermore, the product may, if so desired, still be purified using various techniques, such as recrystallisation, reprecipitation or the various chromatography techniques, in particular column chromatography or preparative thin-layer chromatography.

It will be appreciated that the compounds which are useful according to the present invention may have asymmetric centres. These asymmetric centres can be independently in an R or S configuration. It will appear to a person skilled in the art that some compounds which are useful according to the present invention may also have a geometric isomerism. It must be understood that the present invention includes individual geometric isomers and stereoisomers and mixtures of thereof, including racemic mixtures, of compounds from the aforementioned formula (I). Isomers of this type may be separated from their mixtures by applying or adapting known processes, for example chromatography techniques or recrystallisation techniques, or they are prepared separately from suitable isomers of the intermediates thereof.

For the purposes of this text, it is understood that tautomeric forms are included in the citation of a given group, for example thio/mercapto or oxo/hydroxy.

The acid addition salts are formed with the compounds that are useful according to the invention in which a basic group, such as an amino, alkylamino or dialkylamino group, or even pyridine or phenol, is present. The pharmaceutically acceptable, i.e. non-toxic, acid addition salts are preferred. The selected salts are optimally chosen so as to be compatible with the usual pharmaceutical vehicles and suitable for oral or parenteral administration. The acid addition salts of the compounds that are useful according to the present invention can be prepared by reacting the free base with the appropriate acid, by applying or adapting known processes. For example, the acid addition salts of the compounds that are useful according to the present invention can be prepared either by dissolving the free base in water or in an alcoholised aqueous solution or suitable solvents containing the appropriate acid, and isolating the salt by evaporating the solution, or by reacting the free base and the acid in an organic solvent, in which case the salt separates out directly or can be obtained by concentrating the solution. Suitable acids for use in the preparation of these salts include hydrochloric acid, hydrobromic acid, phosphoric acid, sulfuric acid, various organic carboxylic and sulfonic acids, such as acetic acid, citric acid, propanoic acid, succinic acid, benzoic acid, tartaric acid, fumaric acid, mandelic acid, ascorbic acid, malic acid, methanesulfonic acid, toluenesulfonic acid, fatty acids, adipate, alginate, ascorbate, aspartate, benzenesulfonate, benzoate, cyclopentanepropionate, digluconate, dodecyl sulfate, bisulfate, butyrate, lactate, laurate, lauryl sulfate, malate, hydriodide, 2-hydroxyethanesulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonoate, hexanoate, camphorate, camphorsulfonate and the like.

The acid addition salts of the compounds that are useful according to the present invention can be regenerated from the salts by applying or adapting known processes. For example, the parent compounds that are useful according to the invention can be regenerated from their acid addition salts by treatment with an alkali, for example aqueous sodium bicarbonate solution or aqueous ammonia solution.

The compounds that are useful according to the present invention can be regenerated from the base addition salts thereof by applying or adapting known processes. For example, the parent compounds which are useful according to the invention can be regenerated from their base addition salts by treatment with an acid, for example a hydrochloric acid.

The base addition salts can be formed if the compound that is useful according to the invention contains a carboxyl group, or else pyridine or phenol, or a sufficiently acidic bioisostere. The bases which can be used to prepare the base addition salts preferably include those that produce, if they are combined with a free acid, pharmaceutically acceptable salts, i.e. salts, the cations of which are not toxic to the patient in the pharmaceutical doses of the salts, in such a way that the beneficial inhibitory effects intrinsic in the free base are not negated by the side effects attributable to the cations. The pharmaceutically acceptable salts, including those derived from alkaline-earth metal salts, within the scope of the present invention, include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methylglucamine, lysine, arginine, ornithine, choline, N,N' dibenzylethylenediamine, chloroprocaine, diethanolamine, procaine, N-benzylphenethylamine, diethylamine, piperazine, tris(hydroxymethyl)aminomethane, tetramethylammonium hydroxide and the like.

Compounds which are useful according to the present invention can be easily prepared, or formed during the process of the invention, in the form of solvates (for example hydrates). Hydrates of the compounds that are useful according to the present invention can be easily prepared by recrystallisation of an aqueous/organic solvent mixture, using organic solvents such as dioxane, tetrahydrofuran or methanol.

The basic products or the reagents used are commercially available and/or can be prepared by applying or adapting known processes, for example processes as described in the Reference Examples or obvious chemical equivalents thereof.

According to the present invention, compounds of formula (I) have biological activity in metal chelation and/or amyloid aggregate dissolution.

The present invention also relates to pharmaceutical compositions comprising a compound according to the invention having a pharmaceutically acceptable vehicle or excipient.

Preferably, said composition contains an effective amount of the compound according to the invention.

According to another subject, the present invention also relates to the use of compounds of formula (I) for preparing pharmaceutical compositions intended to chelate metal ions, more preferably those of zinc, copper, iron, aluminium or manganese, more preferably zinc ions at oxidation stage II, copper ions at oxidation stage I, II, and iron ions at oxidation stage II, III, IV or V.

The invention also relates to the use of compounds of general formula (I) for the preparation of pharmaceutical compositions intended to dissolve amyloid aggregates.

According to another subject, the invention also relates to the use of compounds of general formula (I) for the preparation of pharmaceutical compositions intended to prevent and/or treat neurodegenerative diseases. More particularly, the neurodegenerative diseases are selected from Alzheimer's disease, Parkinson's disease, Huntington's disease, amyotrophic lateral sclerosis or Down syndrome, and spongiform encephalopathies, such as Creutzfeldt-Jakob's disease.

According to another subject, the present invention also relates to methods for the aforementioned therapeutic treatment comprising the administration of a compound according to the invention to a patient who requires it.

Preferably, said composition is administered to a patient who requires it.

Pharmaceutical compositions according to the invention may be presented in forms intended for parenteral, oral, rectal, intravenous, permucosal or percutaneous administration.

Therefore, they will be presented in the form of solutes or injectable suspensions or multi-dose vials, in the form of plain or coated tablets, dragees, capsules, gel capsules, pills, wafer capsules, powders, suppositories or rectal capsules, solutions or suspensions, for percutaneous use in a polar solvent or for permucosal use.

The excipients suitable for such administrations are cellulose or microcrystalline cellulose derivatives, alkaline-earth metal carbonates, magnesium phosphate, starches, modified starches and lactose for solid forms.

For rectal use, cocoa butter or polyethylene glycol stearates are the preferred excipients.

For parenteral use, water, aqueous solutes, physiological serum and isotonic solutes are the vehicles most appropriately used.

The dosage can vary within wide ranges (0.5 mg to 1000 mg) as a function of the therapeutic indication and the method of administration, and also of the age and weight of the patient.

LEGENDS OF THE FIGURES

FIG. 1: Quinoline derivatives tested on Aβ.

FIG. 2: cis and trans configurations for complexing metal ions using 8-hydroxyquinoline derivatives.

Figure 3:
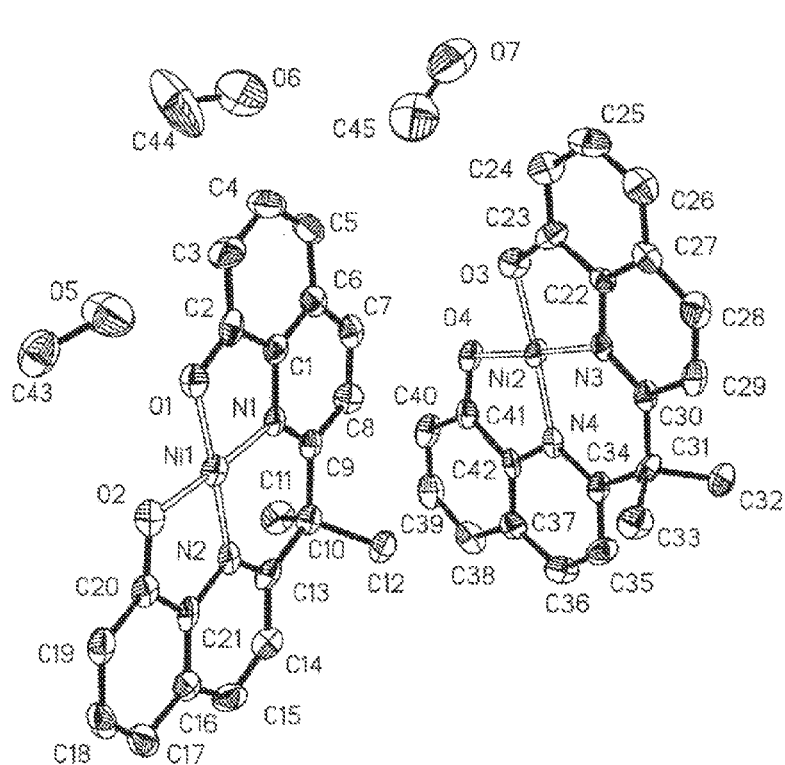

FIG. 3: Crystalline structure of [2,2'-(2,2-propanediyl)-bis[8-quinolinolato]nickel(II); the hydrogen atoms have been omitted. Note that the complex has a cis configuration (FIG. 2) and that the two quinoline entities of the ligand chelate the same metal atom.

Figure 4:
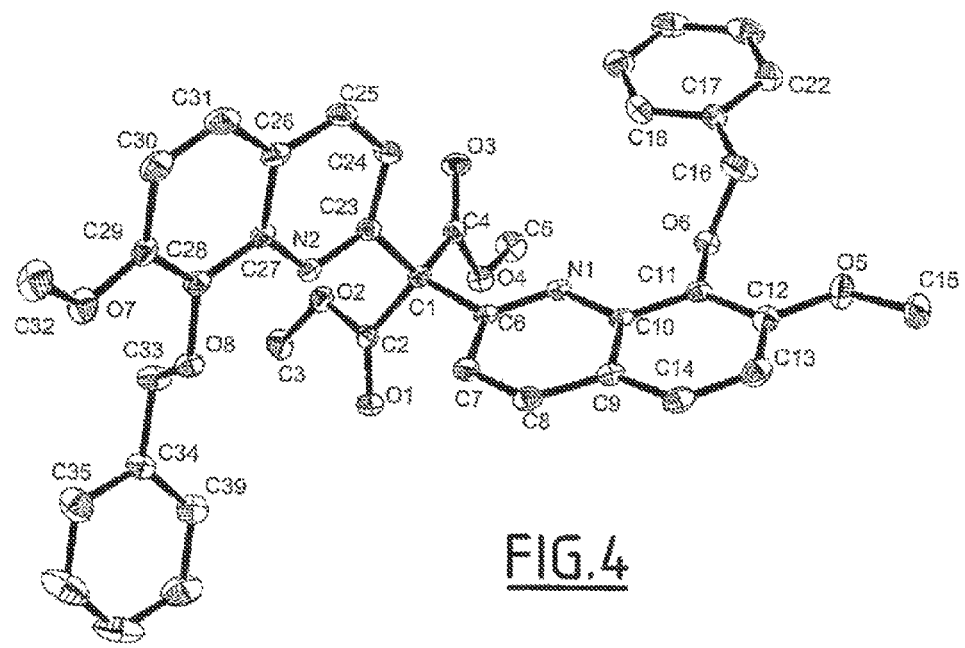

FIG. 4: Crystalline structure of bis{7-(methyloxy)8-[phenylmethyl)oxy]-2-quinolinyl}propanedioate, the hydrogen atoms having been omitted.

Figure 5:
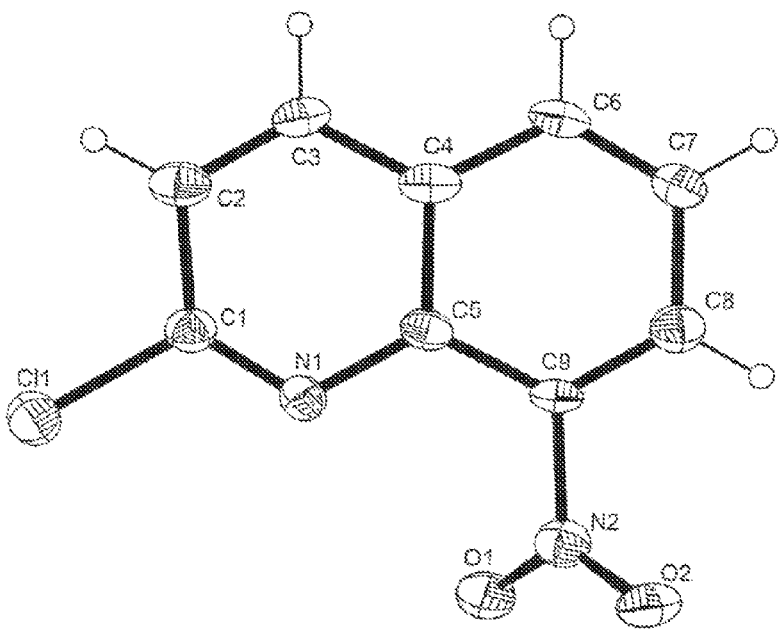

FIG. 5: Crystalline structure of 2-chloro-8-nitroquinoline.

Figure 6:
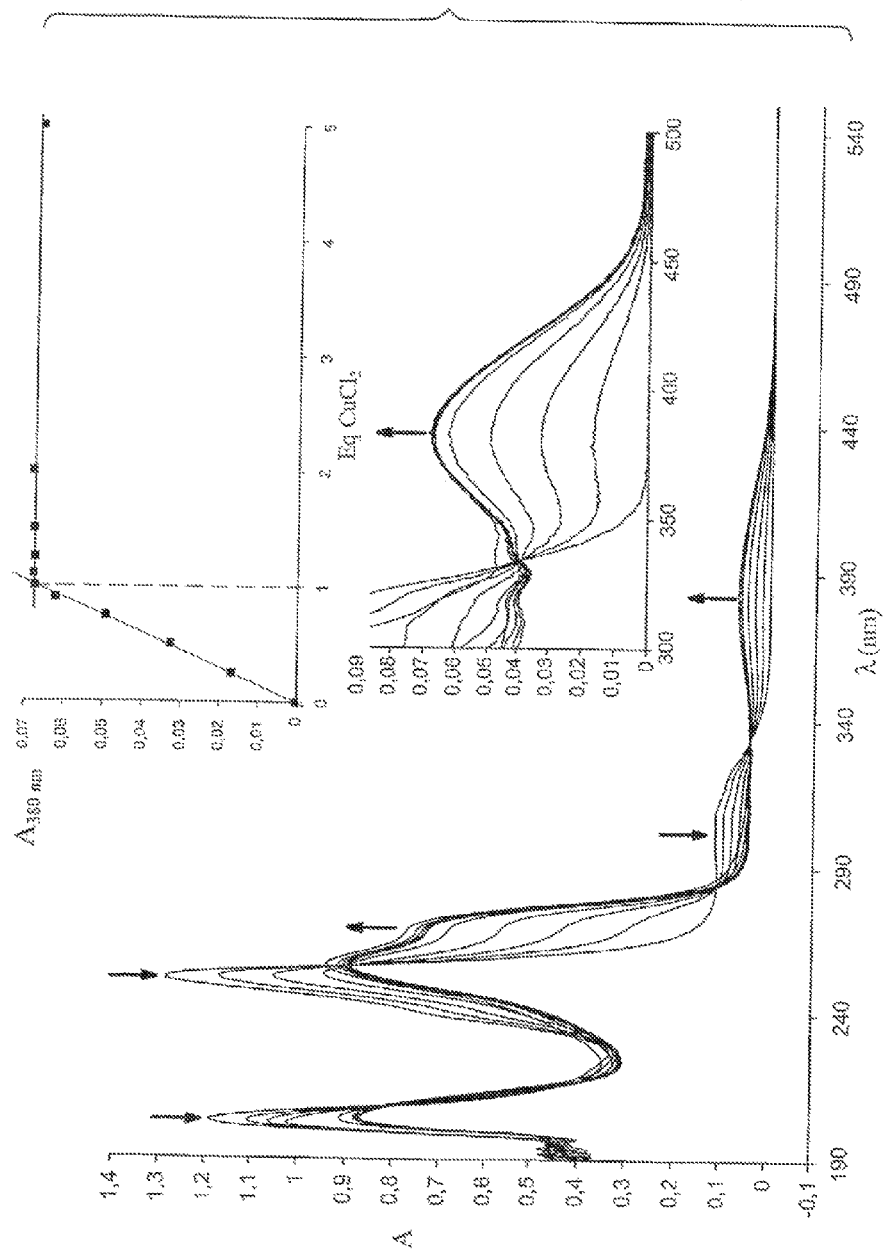

FIG. 6: UV-visible spectra obtained during the Cu(II) titration by the ligand 3. Titration spectra are obtained with 15 μM of ligand (L) in the 20 mM Tris-HCl buffer mixture containing 150 mM NaCl (pH=7.4)/CH$_3$OH (1/1, v/v) and different CuCl$_2$ ratios. The direction of the arrows indicates variations observed on the spectra when the Cu(II)/L ratio increases.

Figure 7:
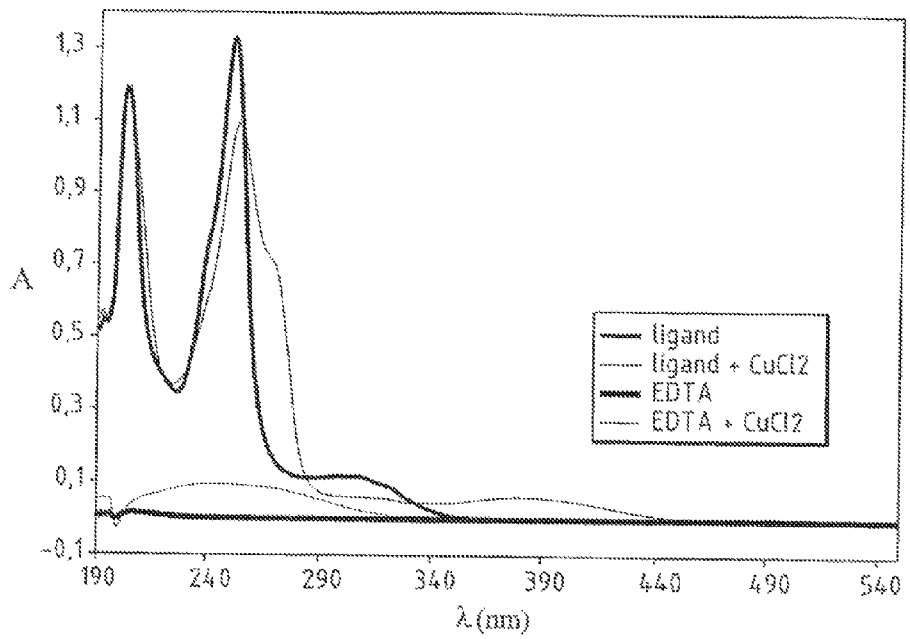

FIG. 7: UV-visible spectra of 3; Cu(II)-3; EDTA and (EDTA)Cu(II) in the 20 mM Tris-HCl buffer mixture containing 150 mM NaCl (pH=7.4)/CH$_3$OH (1/1, v/v). The concentration of the ligands and metal complexes is 15 μM. Note that an absorbency at λ=379 nm is only observed for the Cu(II)-3 complex.

Figure 8:
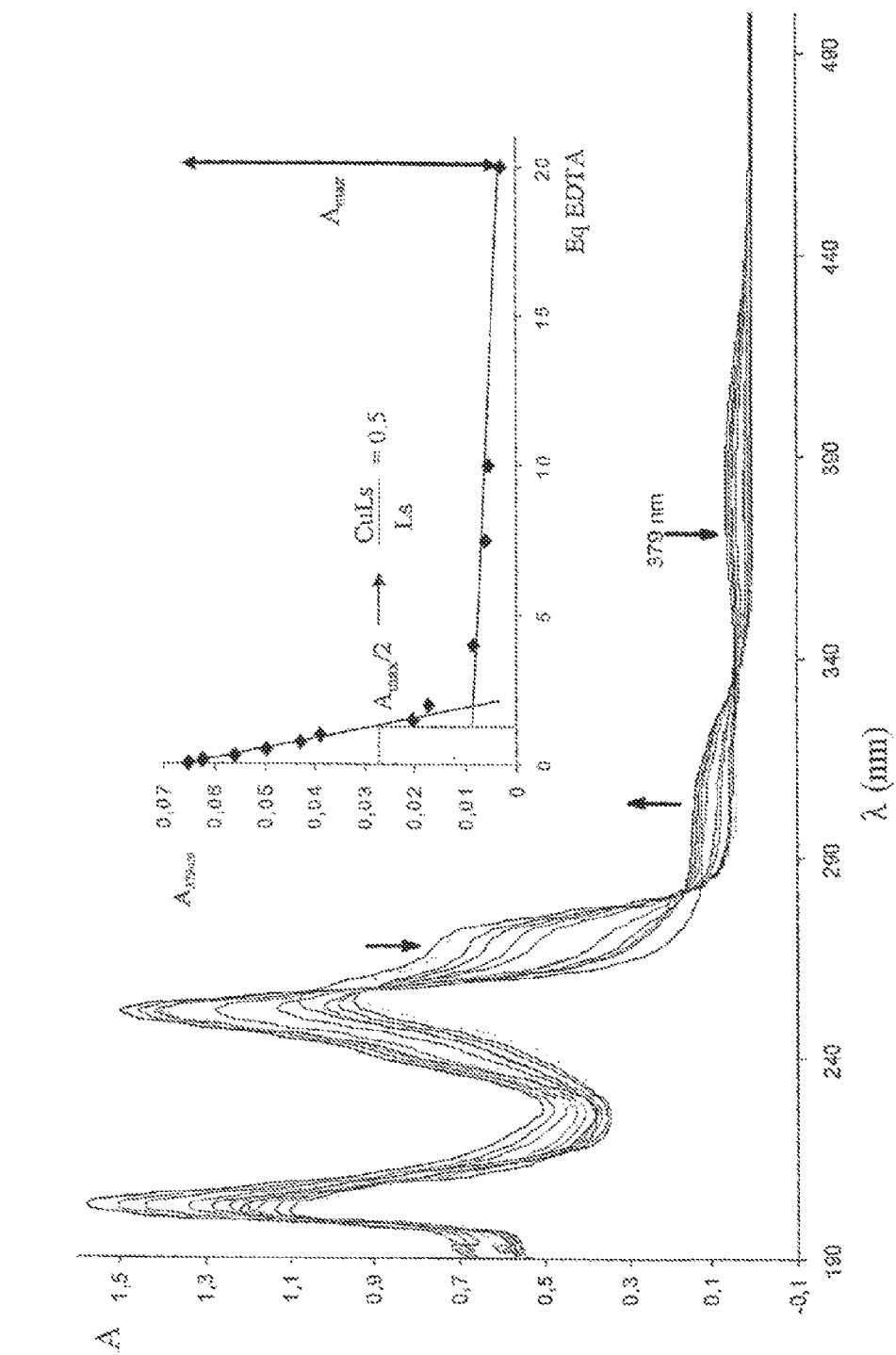

FIG. 8: Competition reaction for complexing CuCl$_2$ by the ligand 3(L$_s$) and EDTA (L$_c$).

The spectra are obtained having 15 μM of 3 and CuCl$_2$ and different EDTA ratios in the 20 mM Tris-HCl buffer mixture containing 150 mM NaCl (pH=7.4)/CH$_3$OH (1/1, v/v). The direction of the arrows indicates absorbency variations observed when the L$_c$/L$_s$ ratio increases.

Figure 9:
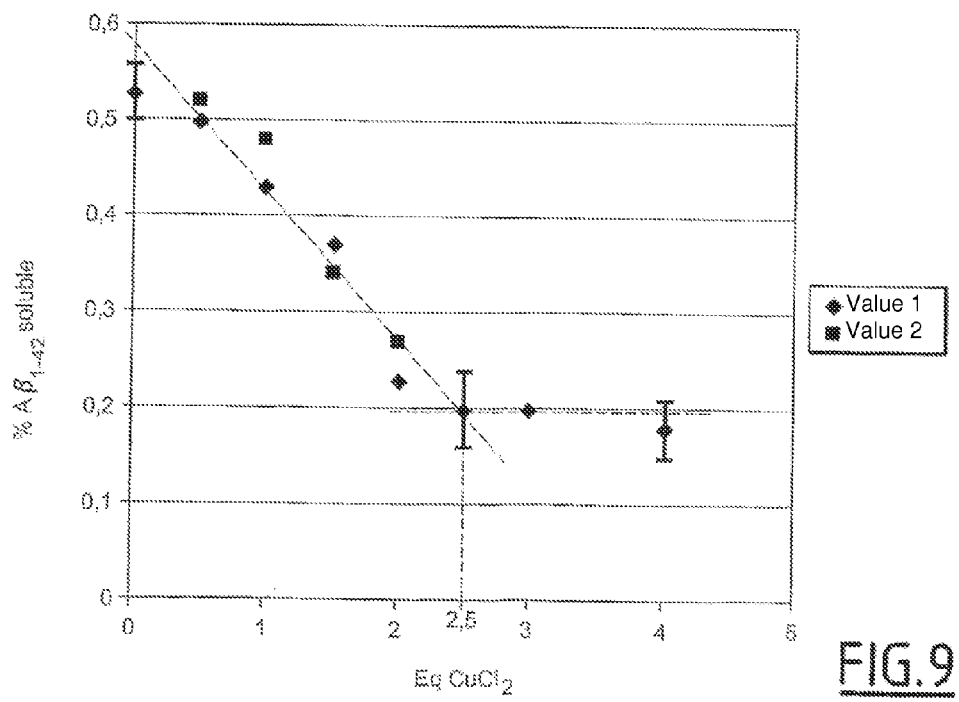

FIG. 9: Variation of the percentage of soluble Aβ$_{1-42}$ peptide as a function of the Aβ/Cu(II) stoichiometry. The Aβ$_{1-42}$ (5 μM) peptide is incubated for two hours at 37° C. in a 20 mM Tris-HCl (pH=7.4) buffer mixture containing 150 mM NaCl in the presence of different Cu(II) stoichiometries, then the reaction mixture is centrifuged. The percentage of peptide in the (soluble Aβ$_{1-42}$) supernatant and in the (aggregated Aβ$_{1-42}$) precipitate are thus quantified by means of a Micro BCA Protein Assays kit. Value 1 and Value 2 are from two independent experiments, when the number of measures is 3, the mean and standard deviation values obtained are presented.

FIG. 10: Percentage variation of soluble Aβ$_{1-42}$ peptide in the presence of various CuCl$_2$ and ligand stoichiometries. Aβ$_{1-42}$ (5 μM) peptide is incubated for one hour at 37° C. in a 20 mM Tris-HCl (pH=7.4) buffer mixture containing 150 mM NaCl in the presence of 12.5 or 20 μM CuCl$_2$, then the [12.5 μM (except for the quinoline monomers such as 8-hydroxyquinoline, Clioquinol, 8-hydroxyquinaldine and 8-aminoquinoline where this value is 25 μM) or 200 μM] ligand is added. After a further hour of incubation, the reaction mixture is centrifuged. The percentage of peptide in the (soluble Aβ$_{1-42}$) supernatant and in the (aggregated Aβ$_{1-42}$) precipitate are thus quantified by means of a Micro BCA Protein Assays kit. For each compound, the values on the left (in dark grey) and the values on the right (in light grey) represent the results obtained for the 200 μM ligand/20 μM CuCl$_2$ and 12.5 μM (in the case of quinoline dimers or 25 μM in the case of monomers) ligand/12.5 μM CuCl$_2$ ratios respectively. Percentages of soluble Aβ$_{1-42}$ peptide in the presence of different concentrations of CuCl$_2$ in the absence of a ligand are also indicated.

Figure 11:
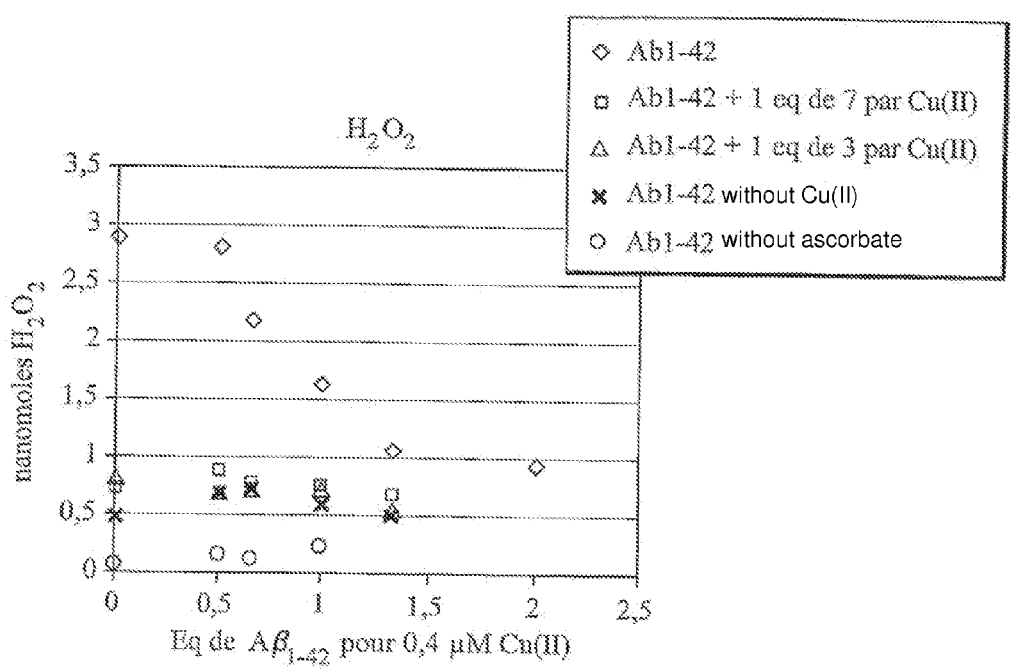

FIG. 11: Variation in H$_2$O$_2$ production by copper complexes of Aβ$_{1-42}$ peptide as a function of the Cu(II)/Aβ stoichiometry. Experiments are carried out for 5 minutes in a sodium phosphate buffer (pH=7.4) in the presence 0.4 µM CuCl$_2$, 10 µM ascorbate and air with or without 0.4 µM of 3 or 7. The H$_2$O$_2$ released is quantified by means of an Amplex-Red H$_2$O$_2$/HRP Assay kit.

The following examples illustrate the invention, without limiting it. The initial products used are products known or prepared according to known procedures.

The following abbreviations have been used hereinbefore or hereinafter:

Aβ: β-amyloid peptide; BSA: Bovine Serum Albumin; biPy: 2,2'-bipyridine; BnCl: benzyl chloride; BOP: (benzotriazole-1-yloxy)tris(dimethylamino)phosphonium hexafluorophosphate; CTDA: trans-1,2-diaminocyclohexane-N,N,N', N'-tetraacetic acid; d: doublet; rd: resolved doublet; CID: chemical ionisation detection; Dien: diethylenetriamine; DMF: dimethylformamide; DMSO: dimethylsulfoxide; DTPA: diethylene-triaminepentaacetic acid; EDA: ethylenediamine; EDDA: ethylenediamine-N,N'-diacetic acid; EDTA: ethylenediaminetetraacetic acid; EGTA: ethylenebis(oxyethylenenitrilo)-tetraacetic acid; eq: equivalent; Eq.: equation; HOBT: 1-hydroxybenzotriazole monohydrate; HRP: Horse Radish Peroxidase; HIDA: N-(2-hydroethyl)iminodiacetic acid; LDA: lithium diisopropylamine; m: mass; mCPBA: m-chloroperbenzoic acid; NBS: N-bromosuccinimide; NTA: nitrilotriacetic acid; Pd$_2$(dba)$_2$: tris(dibenzylidene-acetone)-dipalladium(0); MW: molecular weight rac-BINAP: rac-2,2'-bis(diphenylphosphino)-1,1',binaphthyl; s: singlet MS: mass spectrometry; t: triplet; Tetren: tetraethylenepentamine; THF: tetrahydrofuran; Trien: triethylenetetramine; rpm: revolutions per minute.

EXAMPLES

Description of the Examples

Synthesis:
General Remarks Concerning Organic Synthesis:

8-methyloxyquinaldine was synthesised by a method described in the literature. (C. Kitamura et al., *J. Chem. Soc., Perkin Trans.* 1 2000, 781-785). N-butyl-2,2'-imino-bis(8-nitroquinoline) was synthesised according to the references: H. Jiang et al. *Tetrahedron* 2003, 59, 8365-8374; G. Xue et al., *Tetrahedron* 2001, 57, 7623-7628 and P. Belser et al. *Tetrahedron* 1996, 52, 2937-2944. 7-bromo-8-hydroxyquinoline (prepared according to the method of Pearson: D. E. Pearson et al. *J. Org. Chem.* 1967, 32, 2358-2360; G. E. Collis et al. *Acta Cryst.* 2003, C59, o443-o444). 1,1-dimethyl(2-formyl-8-quinolinyl)carbamate was synthesised according to G. Xue et al., *Tetrahedron* 2001, 57, 7623-7628. 2-Chloro-8-nitroquinoline was synthesised according to M. C. Kimber et al., *Aust. J. Chem.* 2003, 56, 39-44.

Acetonitrile was dried over a 4 Å molecular sieve. Tetrahydrofuran (THF) was distilled over benzophenone in the presence of sodium. Dry CuCl$_2$ was obtained by heating under a vacuum at 50° C. Dichloromethane was dried over basic alumina. Other reagents and solvents used were provided by standard suppliers of chemical products and were used without subsequent purification.

NMR spectra were recorded on Bruker machines (200, 250 or 500 MHz). The electrospray ionisation mass spectrometer (ESI-MS/MS) was a Perkin-Elmer SCIEX API 365, the samples being fed into the electrospray source using a Harvard Apparatus syringe pump. UV-visible spectra were recorded on a Hewlett Packard 8452A diode spectrophotometer or a Perkin-Elmer Lamda 35 spectrophotometer.

Thin-layer chromatography is carried out on silica plates.

Dimethyl-bis[8-(acetyloxy)-2-quinolinyl]propanedioate (Compound 1")

The protocol was optimised using works by: Y. Yamamoto et al., *Bull. Chem. Soc. Jpn.* 1978, 51, 3489-3495. A suspension of 8-hydroxyquinoline-N-oxide (4.47) g; 27.7 mmol) and dimethylmalonate 3.35 ml; 29.1 mmol) in acetic anhydride (11.2 ml) is stirred for 27 days at ambient temperature with protection from moisture (by means of a tube of CaCl$_2$) and light. The orange suspension obtained is cooled at 0° C. and methanol (6.7 ml) is added. After 2 hours of stirring at ambient temperature, water (30 ml) is added in two phases and the mixture is stirred for a further 2 hours. A precipitate is then collected and washed with an acetic acid/water mixture (1/1, v/v, 30 ml) then water, before it is dried for 15 hours at 110° C. It is then dissolved hot in chloroform (15 ml) and precipitated by adding methanol (45 ml) to yield dimethyl-bis[8-(acetyloxy)-2-quinolinyl]propanedioate in the form of a white powder (4.58 g; 9.12 mmol, yield=66%). NMR-$^1$H (250 MHz, CDCl$_3$) δ, ppm: 8.06 (d, $^3$J (H, H)=9.0 Hz, 2H); 7.87 (d, $^3$J (H, H)=9.0 Hz, 2H); 7.64 (dd, $^3$J (H, H)=8.0 Hz, $^4$J (H, H)=1.5 Hz, 2H); 7.49 (m, 2H); 7.41 (dd, $^3$J (H, H)=7.5 Hz, $^4$J (H, H)=1.5 Hz, 2H); 3.94 (s, 6H); 2.53 (s, 6H). MS (CID, NH$_3$) m/z=503 (MH$^+$). Analysis (%) for C$_{27}$H$_{22}$N$_2$O$_8$.0.5H$_2$O: calculated C, 63.40; H, 4.53; N, 5.48. found C, 63.46; H, 4.10; N, 5.56.

2,2'-methanediyl-bis(8-hydroxy-2-quinolinium) dichloride dihydrate (Compound 1')

The protocol was optimised using works by: Y. Yamamoto et al., *Bull. Chem. Soc. Jpn.* 1978, 51, 3489-3495. A suspension of dimethyl-bis[8-(acetyloxy)-2-quinolinyl]propanedioate (4.00 g; 7.97 mmol) in aqueous HCl at 20% (295 ml) is heated with reflux for 5 hours 30 min then stirred for 4 hours at ambient temperature to yield a yellow precipitate which is recovered and dried under vacuum. The product is then dissolved hot in methanol (6.1 ml) which contains concentrated hydrochloric acid (610 µl) then crystallised by adding concentrated hydrochloric acid (6.1 ml) to yield 2,2'-methanediyl-bis(8-hydroxy-2-quinolinium)dichloride dihydrate in the form of yellow crystals (3.27 g; 7.96 mmol, quantitative yield). NMR-$^1$H (250 MHz, DMSO-d$_6$) δ, ppm: 8.72 (d, $^3$J (H, H)=9.0 Hz, 2H); 7.89 (d, $^3$J (H, H)=9.0 Hz, 2H); 7.58 (m, 4H); 7.39 (dd, $^3$J (H, H)=7.5 Hz, $^4$J (H, H)=2.0 Hz, 2H); 5.14 (s, 2H). NMR-$^{13}$C (100 MHz, DMSO-d$_6$) δ, ppm: 156.5 (Cq); 151.3 (Cq); 142.7 (CH); 134.0 (Cq); 129.7 (CH); 129.0 (Cq); 124.3 (CH); 118.9 (CH); 115.1 (CH); 42.2 (CH$_2$). MS (CID, NH$_3$) m/z: 302 (MH$^+$). Analysis (%) for C$_{19}$H$_{12}$N$_2$O$_2$.2HCl.2H$_2$O: calculated C, 55.49; H, 4.90; N, 6.81. found C, 55.95; H, 4.79; N 6.66.

2,2'-methanediyl-bis(8-hydroxyquinoline) (Compound 1)

2,2'-methanediyl-bis(8-hydroxy-2-quinolinium)dichloride dihydrate (150 mg; 0.36 mmol), suspended in 20 ml of CH$_2$Cl$_2$, is washed three times with a sodium acetate buffer (0.1 M; pH=7.0) then water. The solvent from the organic phase is evaporated to yield, after drying under vacuum, 1 in the form of an orange solid (110 mg, 0.36 mmol, quantitative yield). NMR-$^1$H (250 MHz, CDCl$_3$) δ, ppm: 8.20 (s large, 2H); 8.08 (d, $^3$J (H, H)=8.5 Hz, 2H); 7.43 (d, $^3$J (H, H)=8.5 Hz, 2H); 7.42 (m, 2H); 7.30 (dd, $^3$J (H, H)=8.0 Hz, $^4$J (H, H)=1.0 Hz, 2H); 7.16 (dd, $^3$J (H, H)=7.5 Hz, $^4$J (H, H)=1.0 Hz, 2H); 4.69 (s, 2H). UV/vis [DMSO/20 mM Tris.HCl pH=7.4; 150 mM NaCl (8/2, v/v)]: λ nm (ε M$^{-1}$ cm$^{-1}$)=256 (50,800), 312 (8,700), 454 (2,200), 480 (3,500), 512 (2,700).

2,2'-methanediyl-bis(5-chloro-8-hydroxyquinoline) (Compound 2)

The protocol was established using works by: H. Gershon, M. W. Mc Neil, *J. Heterocycl. Chem.* 1972, 9, 659-666. N-chlorosuccinimide (324 mg; 2.43 mmol) is added batchwise to a suspension of 2,2'-methanediyl-bis(8-hydroxy-2-quinolinium) dichloride dihydrate (500 mg; 1.22 mmol) in H$_2$SO$_4$ at 97% (12 ml), cooled over an ice bath. The mixture is then stirred for 15 minutes at 0° C. then for 4 hours at ambient temperature. It is subsequently poured over ice to yield a pink suspension which is neutralised with an aqueous sodium hydroxide solution. The mixture is then centrifuged. After removing the supernatant, the precipitate is suspended in water and extracted with dichloromethane. The organic phase is washed in water and the solvent subsequently evaporated under vacuum to yield, after drying under vacuum, 2 in the form of a pale orange powder (440 mg; 1.19 mmol; yield=98%). NMR-$^1$H (250 MHz, CDCl$_3$) δ, ppm: 8.45 (d, $^3$J (H, H)=8.5 Hz, 2H); 8.12 (s large, 2H); 7.56 (d, $^3$J (H, H)=8.5 Hz, 2H); 7.48 (d, $^3$J (H, H)=8.0 Hz, 2H); 7.10 (d, $^3$J (H, H)=8.0 Hz, 2H); 4.74 (s, 2H). NMR-$^{13}$C (63 MHz, CDCl$_3$) δ, ppm: 157.4 (Cq); 151.0 (Cq); 138.1 (Cq); 134.2 (CH); 127.2 (CH); 125.0 (Cq); 123.3 (CH); 120.4 (Cq); 110.3 (CH); 47.5 (CH$_2$). MS (CID, NH$_3$) m/z: 371 (MH$^+$). Analysis (%) for C$_{19}$H$_{12}$O$_2$N$_2$O$_2$.0.1Na$_2$SO$_4$: calculated C, 59.21; H, 3.14; N, 7.27. found C 59.27; H 2.58; N 7.05. UV/vis [dioxane/20 mM Tris-HCl pH=7.4 containing 150 mM NaCl (1/1, v/v)]: λ nm (ε M$^{-1}$ cm$^{-1}$)=258 (59,900), 320 (7,000), 460 (2,000), 489 (2,900), 518 (2,100).

[2,2'-(2,2-propanediyl)-bis[8-quinolinolato]nickel(II)

The synthesis was carried out according to the reference protocol: Y. Yamamoto et al., *Bull. Chem. Soc. Jpn.* 1978, 51, 3489-3495. NMR data which are more specific than those previously published are added hereinafter. NMR-$^1$H (250 MHz, CDCl$_3$) δ, ppm: 8.15 (d, $^3$J (H, H)=9.0 Hz, 2H); 7.45 (d large, $^3$J (H, H)=9.0 Hz, 2H); 7.33 (m, 2H); 6.91 (d large, $^3$J (H, H)=7.5 Hz, 2H); 6.81 (d large $^3$J (H, H)=6.5 Hz, 2H); 1.93 (s, 6H). NMR-$^{13}$C (63 MHz, CDCl$_3$) δ, ppm: 166.4 (Cq); 159.1 (Cq); 144.3 (Cq); 138.7 (CH); 130.7 (CH); 127.7 (Cq); 119.3 (CH); 113.6 (Cq); 110.4 (CH); 50.7 (CH$_3$). MS (CID, NH$_3$): m/z=387 (MH$^+$), 404 (MNH$_4^+$). The molecule structure was confirmed by X-ray diffraction analysis of monocrystals obtained by crystallisation of the product in methanol. The structure of the complex is presented in FIG. 3. The parameters for crystal analysis are as follows: triclinic crystal system, P-1; a=12.456(4) Å, b=12.650(4) Å, c=13.983(5) Å, α=112.260(5)°, β=105.956(5)°, γ=90.115(6)°.

2,2'-(2,2-propanediyl)-bis(8-hydroxyquinoline) (Compound 3)

The protocol was optimised using works by: Y. Yamamoto et al., *Bull. Chem. Soc. Jpn.* 1978, 51, 3489-3495. Red crystals of [2,2'-(2,2-propanediyl)-bis[8-quinolinolato]nickel(II) (3.32 g; 8.60 mmol) are suspended in 80 ml of ethanol then 16 ml of concentrated hydrochloric acid is added to yield a green solution to which 320 ml of boiling water are added batchwise to form yellow crystals. After cooling, the crystals are collected and washed with a 1M aqueous HCl solution then dried in the air at ambient temperature for 15 hours prior to being dissolved hot again in 32 ml of ethanol. A boiling 18.4 mM aqueous solution of sodium acetate is then added batchwise. After cooling, a precipitate is recovered by centrifugation then washed in water and extracted with dichloromethane to yield, after evaporation of the solvent and drying under vacuum, 3 in the form of a white solid (1.81 g). The precipitation supernatant from the previous stage, which contains a residual amount of the nickel complex, is neutralised with a 6 M aqueous sodium hydroxide solution then 1 l of dichloromethane is added; the product is stripped using an aqueous solution of ethylenediaminetetraacetic acid (2×10 g in 500 ml) and stirred for 1 hour. The organic phase is recovered, washed in water, then concentrated under vacuum. The mixture is then purified by chromatography over silica gel using a gradient of 0 to 1% of CH$_3$OH in CH$_2$Cl$_2$ (v/v) to yield a further 0.83 g of 3 in the form of a white solid (total mass=2.64 g; 8.00 mmol, yield=93%). NMR-$^1$H (250 MHz, CDCl$_3$) δ, ppm: 8.30 (s large, 2H); 8.02 (d, $^3$J (H, H)=9.0 Hz, 2H); 7.45 (m, 2H); 7.30 (dd, $^3$J (H, H)=7.5 Hz, $^4$J (H, H)=1.0 Hz, 2H); 7.22 (d, $^3$J (H, H)=9.0 Hz 2H); 7.21 (dd, $^3$J (H, H)=7.5 Hz, $^4$J (H, H)=1.0 Hz, 2H); 2.0 (s, 6H). NMR-$^{13}$C (63 MHz, CDCl$_3$) δ, ppm: 164.7 (Cq); 152.1 (Cq); 136.8 (Cq); 136.5 (CH); 127.5 (CH); 126.8 (Cq); 121.2 (CH); 117.5 (Cq); 110.3 (CH); 49.3 (Cq); 28.0 (CH$_3$). MS (CID, NH$_3$) m/z: 331 (MH$^+$). Analysis (%) for C$_{21}$H$_{18}$N$_2$O$_2$: calculated C, 76.34; H, 5.49; N, 8.48. found C, 75.80; H, 5.30; N, 8.38. UV/vis [CH$_3$OH/20 mM Tris-HCl pH=7.4 containing 150 mM NaCl (1/1, v/v)]: λ nm (ε M$^{-1}$ cm$^{-1}$)=203 (77,700), 251 (84,600), 308 (6,900).

2,2'-(2,2-Propanediyl)-bis(5-chloro-8-hydroxyquinoline) (Compound 4)

The protocol was established using works by: H. Gershon et al., *J. Heterocycl. Chem.* 1972, 9, 659-666. N-chlorosuccinimide (40 mg; 0.30 mmol) is added batchwise to a solution of 3 (50 mg; 0.15 mmol) in H$_2$SO$_4$ at 97% (1.5 ml) and cooled over an ice bath. The mixture is then stirred for 15 minutes at 0° C. then for 3 hours at ambient temperature. It is subsequently poured over ice to yield a yellow suspension which is neutralised with a 3 M aqueous solution of sodium hydroxide. The mixture is centrifuged, the supernatant is removed then the precipitate is suspended in water and extracted with dichloromethane. The organic phase is washed in water and the solvent subsequently evaporated to yield 4 in the form of a white powder (55 mg; 0.14 mmol; yield=93%). NMR-$^1$H (250 MHz, CDCl$_3$) δ, ppm: 8.37 (d, $^3$J (H, H)=9.0 Hz, 2H); 8.19 (s large, 2H); 7.50 (d, $^3$J (H, H)=8.0 Hz, 2H); 7.32 (d, $^3$J (H, H)=9.0 Hz, 2H); 7.13 (d, $^3$J (H, H)=8.2 Hz, 2H); 2.00 (s, 6H). NMR-$^{13}$C (63 MHz, CDCl$_3$) δ, ppm: 165.2 (Cq); 151.1 (Cq); 137.3 (Cq); 134.0 (CH); 127.2 (CH); 124.7 (Cq); 121.9 (CH); 120.5 (CH); 110.2 (CH); 49.4 (Cq); 27.9 (CH$_3$). MS (CID, NH$_3$) m/z: 399 (MH$^+$). Analysis (%) for C$_{21}$H$_{16}$Cl$_2$N$_2$O$_2$: calculated C, 63.17; H, 4.04; N, 7.02. found C, 63.02; H, 3.76; N, 6.87. UV/vis [dioxane/20 mM Tris-HCl pH=7.4 containing 150 mM NaCl (1/1, v/v)]: λ nm (ε M$^{-1}$ cm$^{-1}$)=258 (72,500), 315 (8,300).

2,2'-(Difluoromethanediyl)-bis(8-hydroxyquinoline) (Compound 5)

1-chloromethyl-4-fluoro-1,4-diazoniabicyclo(2,2,2)octane bis(tetrafluoroborate) (F-TEDA-BF$_4$, Selectfluor™, 258 mg; 0.73 mmol) is added batchwise under nitrogen to an orange suspension of 2,2'-methanediyl-bis(8-hydroxy-2-quinoline) (compound 1110 mg; 0.36 mmol) in 30 ml dry d' acetonitrile, which leads to solubilisation of the products in the form of a yellow solution. The mixture is stirred for 90 minutes at ambient temperature. After evaporation of the solvent, the product is solubilised in dichloromethane and washed twice in water. The organic phase is concentrated and dried under vacuum to yield 5 in the form of a yellow powder (123 mg; 0.36 mmol, quantitative yield). NMR-$^1$H (250 MHz, CDCl$_3$) δ, ppm: 8.34 (d, $^3$J (H, H)=8.5 Hz, 2H); 8.00 (d, $^3$J (H, H)=8.5 Hz, 2H); 7.78 (s, 2H); =7.52 (m, 2H); 7.39 (dd, $^3$J (H, H)=8.0 Hz, $^4$J (H, H)=1.0 Hz, 2H); 7.19 (dd, $^3$J (H, H)=7.5 Hz, $^4$J (H, H)=1.0 Hz, 2H). NMR-$^{13}$C (126 MHz, CDCl$_3$) δ, ppm: 152.3 (t, $^2$J (C, F)=30.0 Hz, Cq); 152.3 (Cq); 137.6 (CH); 137.2 (Cq); 129.3 (CH); 128.5 (Cq); 118.7 (t, $^3$J(C, F)=3.5 Hz, CH); 117.9 (CH); 117.0 (t, $^1$J (C, F)=245.6 Hz, Cq); 111.0 (CH). NMR-$^{19}$F (188 MHz, CDCl$_3$, reference: CF$_3$CO$_2$H) δ, ppm: −22.2. MS (CID, NH$_3$) m/z: 339 (MH$^+$, 356 (MNH$_4^+$). Analysis (%) for C$_{19}$H$_{12}$F$_2$N$_2$O$_2$.0.3H$_2$O: calculated C, 66.39; N, 3.69; N, 8.15. found C, 66.25; H, 3.62; N, 8.27. Uv/vis [CH$_3$OH/20 mM Tris-HCl pH=7.4 containing 150 mM NaCl (1/1, v/v)]: λ nm (ε M$^{-1}$ cm$^{-1}$)=241 (50,000), 251 (55,600), 314 (4,700).

Bis(8-hydroxy-2-quinoline)methanone
(Compound 6)

2,2'-methanediyl-bis(8-hydroxy-2-quinolinium)dichloride dehydrate (60 mg; 0.16 mmol) is stirred into 8 ml of a THF/saturated aqueous solution of NaHCO$_3$ (1/1, v/v) mixture for 48 hours. 10 ml of CH$_2$Cl$_2$ and 10 ml of water are then added and the reaction mixture is transferred to a separating funnel. The organic phase is recovered and the aqueous phase is subsequently extracted with CH$_2$Cl$_2$ (2×10 ml). The organic phases are combined and washed in water (1×10 ml), then the solvent is evaporated under vacuum. The product is then purified by filtration over silica gel with a CH$_2$Cl$_2$/CH$_3$OH (97/3, v/v) mixture as solvent. Evaporation of the solvent from the filtrate yields 6 in the form of a red powder (42 mg; 0.13 mmol, yield=81%). NMR-$^1$H (250 MHz, CDCl$_3$) δ, ppm: 8.36 (d, $^3$J (H, H)=8.5 Hz, 2H); 8.19 (d, $^3$J (H, H)=8.5 Hz, 2H); 8.04 (s large, 2H); 7.59 (m, 2H); 7.43 (dd, $^3$J (H, H)=8.5 Hz, $^4$J (H, H)=1.0 Hz, 2H); 7.22 (dd, $^3$J (H, H)=7.5 Hz, $^4$ (H, H)=1.0 Hz, 2H). NMR-$^{13}$C (126 MHz, CDCl$_3$) δ, ppm: 192.2 (Cq); 153.1 (Cq); 151.4 (Cq); 137.1 (Cq); 137.0 (CH); 130.4 (CH); 129.5 (Cq); 121.8 (CH); 117.9 (CH); 111.2 (CH). MS (CID, NH$_3$) m/z: 317 (MH$^+$). Analysis (%) for C$_{19}$H$_{12}$N$_2$O$_3$.0.5H$_2$O: calculated C, 70.15; H, 4.03; N, 8.61. found C, 70.11; H, 3.83; N, 8.94. UV/vis [CH$_3$OH/20 mM Tris-HCl pH=7.4 containing 150 mM NaCl (1/1, v/v)]: λ nm (ε M$^{-1}$ cm$^{-1}$)=254 (43,300), 273 (26,100), 310 (9,600 shoulder), 375 (2,300).

2,2'-(1,2-Ethanediyl)-bis[8-(methyloxy)quinoline]
(Compound 7')

The product has already been described in: C. Kitamura et al., *J. Chem. Soc.*, Perkin Trans. 1 2000, 781-785, but the protocol is different and was established using the synthesis of another product by T. Garber et al., *Inorg. Chem.* 1990, 29, 2863-2868. A solution under argon of 8-methoxyquinaldine (5.32 g; 30.75 mmol) in 47 ml of dry THF is cooled to −95° C. using a methanol/liquid nitrogen mixture. A 1.5 M solution of lithium diisopropylamine THF in cyclohexane (20.5 ml; 30.7 mmol) and dry THF (63 ml) is added over 2 hours. The solution is stirred for a further 2 hours at −95° C., then 1,2-dibromoethane (5.30 ml; 61.5 mmol) is added. The mixture is brought to ambient temperature and stirred for 15 hours. Water (32 ml) is then added, leading to the formation of a white precipitate which is recovered by filtration. The filtrate is concentrated under vacuum and subjected to silica gel column chromatography eluted with a gradient of 0 to 90% of ethyl acetate in CHCl$_3$ (v/v). The product obtained by chromatography and the precipitate are combined and crystallised hot in methanol to yield 2,2'(1,2-ethanediyl)-bis[8-(methyloxy)quinoline] in the form of a white solid (2.04 g; 5.93 mmol, yield=38%). NMR-$^1$H (250 MHz, CDCl$_3$) δ, ppm: 8.04 (d, $^3$J (H, H)=8.5 Hz, 2H); 7.40 (d, $^3$J (H, H)=8.5 Hz, 2H); 7.39 (m, 2H); 7.35 (dd, $^3$J (H, H)=8.0 Hz, $^4$J (H, H)=1.5 Hz, 2H); 7.06 (dd, $^3$J (H, H)=7.5 Hz, $^4$J (H, H)=1.5 Hz, 2H); 4.10 (s, 6H); 3.61 (s, 4H). MS (CDI, NH$_3$): m/z (%)=345 (MH$^+$).

2,2'-(1,4-Butanediyl)-bis[8-(methyloxy)quinoline]
(Compound 10')

It is obtained as the main by-product in the methanol supernatant from crystallisation of 2,2'-(1,2-ethanediyl)-bis[8-(methyloxy)-quinoline]. A second crystallisation in the methanol makes it possible to obtain a pure methanol solution of the desired product. The solvent is then evaporated to yield, after drying under vacuum, 2,2'-(1,4-butanediyl)-bis[8-(methyloxy)-quinoline] in the form of a white powder (0.68 g; 1.84 mmol, yield=6%). NMR-$^1$H (250 MHz, CDCl$_3$) δ, ppm: 8.01 (d, $^3$J (H, H)=8.5 Hz, 2H); 7.40 (d, $^3$J (H, H)=8.5 Hz, 2H); 7.39 (m, 2H); 7.35 (dd, $^3$J (H, H)=8.0 Hz, $^4$J (H, H)=1.5 Hz, 2H); 7.06 (dd, $^3$J (H, H)=7.5 Hz, $^4$J (H, H)=1.5 Hz, 2H); 4.01 (s, 6H); 3.10 (m, 4H); 1.95 (m, 4H). MS (CDI, NH$_3$): m/z=373 (MH$^+$).

2,2'-(1,2-Ethanediyl)-bis(8-hydroxyquinoline) (Compound 7)

The product has already been described in: C. Kitamura et al., *J. Chem. Soc., Perkin Trans.* 1 2000, 781-785, from which this stage of synthesis was very slightly altered. It has also been described but obtained by another method of synthesis in: M. Albrecht et al., *Synthesis* 1999, 10, 1819-1829. A solution of 2,2'-(1,2-ethanediyl)-bis[8-(methyloxy)quinoline] (2.83 g; 8.23 mmol) in 48% hydrobromic acid (150 ml) is heated under reflux for 24 hours. After cooling to ambient temperature, the mixture is neutralised with a 3M aqueous solution of sodium hydroxide, leading to the formation of a green precipitate. The product is extracted with dichloromethane then washed in water and brine. The organic phase is dried over Na$_2$SO$_4$ and the solvent is evaporated under vacuum to yield 7 in the form of a pale green powder (2.53 g; 8.00 mmol, yield=97%). NMR-$^1$H (250 MHz, CDCl$_3$) δ, ppm: 9.35 (s large, 2H); 8.20 (d, $^3$J (H, H)=8.5 Hz, 2H); 7.53 (d, $^3$J (H, H)=8.5 Hz, 2H); 7.37 (m, 2H); 7.32 (dd, $^3$J (H, H)=6.5 Hz, $^4$J (H, H)=2.0 Hz, 2H); 7.05 (dd, $^3$J (H, H)=6.5 Hz, $^4$J (H, H)=2.0 Hz, 2H); 3.57 (s, 4H). MS (CID, NH$_3$) m/z: 317 (MH$^+$). Analysis (%) for C$_{20}$H$_{16}$N$_2$O$_2$.0.1NaBr: calculated C, 73.53; H, 4.93; N, 8.58. found C, 73.81; H, 4.73; N, 8.50. UV/vis [CH$_3$OH/20 mM Tris-HCl pH=7.4 containing 150 mM NaCl (1/1, v/v)]: λ nm (ε M$^{-1}$ cm$^{-1}$)=204 (71,800), 248 (74,200), 305 (5,200).

2,2'-(1,4-Butanediyl)-bis(8-hydroxyquinoline)
(Compound 10)

The protocol was established from the works of C. Kitamura et al., *J. Chem. Soc., Perkin Trans* 1 2000, 781-785 on the previous product. 2,2'-(1,4-butanediyl)-bis[8-(methyloxy)quinoline] (50 mg, 0.13 mmol) is heated under reflux in hydrobromic acid at 48% (2.7 ml) for 24 hours. After cooling to 4° C. using an ice bath, the reaction mixture is basified to pH=8 with a 3M aqueous solution of sodium hydroxide (5 ml, 15 mmol) and a saturated aqueous solution of $NaHCO_3$ (2 ml). The volume is made up to 15 ml with water and the aqueous phase is extracted with $CH_2Cl_2$ (3×10 ml). The organic phases are combined, washed in water (10 ml), then the solvent is evaporated under vacuum. The product is then purified using silica gel flash chromatography eluted with a $CH_2Cl_2/CH_3OH/CH_3COOH$ (96/3/1, v/v/v) mixture. The last fractions are combined, the solvent is evaporated and the fractions are dissolved again in a mixture of 10 ml of $CH_2Cl_2$ and sodium acetate buffer (10 ml; 0.1 M, pH=7.0). The organic phase is recovered and after evaporation of the solvent yields 10 in the form of a white powder (34 mg; 0.10 mmol; yield=77%). NMR-$^1$H (250 MHz, $CDCl_3$) δ, ppm: 8.04 (d, $^3$J (H, H)=8.5 Hz, 2H); 7.38 (m, 2H); 7.31-7.25 (m, 4H); 7.15 (dd, $^3$J (H, H)=7.5 Hz, $^4$J (H, H)=1.0 Hz, 2H); 3.02 (m, 4H); 1.93 (m, 4H). MS (CID, $NH_3$) m/z: 345 (MH$^+$). Analysis (%) for $C_{22}H_{20}N_2O_2 \cdot 0.25H_2O$: calculated C, 75.73; H, 5.92; N, 8.35. found C, 75.39; H, 5.69; N, 8.63. UV/vis [$CH_3OH$/20 mM Tris-HCl pH=7.4 containing 150 mM NaCl (1/1, v/v)]: λ nm (ε M$^{-1}$ cm$^{-1}$)=202 (81,300), 244 (90,800), 303 (6,300).

2,2'-(1.2-Ethanediyl)-bis(5-chloro-8-hydroxyquinoline 8) (Compound 8)

The protocol was established from the works of C. Kitamura et al., *J. Heterocycl. Chem.* 1972, 9, 659-666. N-chlorosuccinimide (253 mg; 1.90 mmol) is added batchwise to a solution of 7 (300 mg; 0.95 mmol) in 97% $H_2SO_4$ (9.5 ml) and cooled over an ice bath. The mixture is stirred for 15 minutes at 0° C. then for 3 hours at ambient temperature. It is subsequently poured over ice to yield a yellow suspension which is neutralised with a 3M aqueous solution of sodium hydroxide. A green precipitate is then filtered and dried under vacuum prior to being dissolved in 200 ml of dimethylformamide and precipitated twice at 4° C. with 200 ml of water and filtered to yield after drying 8 in the form of a pale green solid (258 mg; 0.67 mmol, yield=71%). NMR-$^1$H (250 MHz, DMSO-$d_6$) δ, ppm: 9.73 (s large, 2H); 8.37 (d, $^3$J (H, H)=8.5 Hz, 2H); 7.70 (d, $^3$J (H, H)=8.5 Hz, 2H); 7.52 (d, $^3$J (H, H)=8.0 Hz, 2H); 7.06 (d, $^3$J (H, H)=8.0 Hz, 2H); 3.64 (s, 4H). NMR-$^{13}$C (100 MHz, DMSO-$d_6$) δ, ppm: 161.5 (Cq); 153.0 (Cq); 139.2 (CH); 133.5 (Cq); 127.4 (CH); 125.4 (Cq); 124.4 (CH); 119.2 (CH); 112.1 (CH); 37.1 ($CH_2$). NMR observation of the $^1$H/$^{13}$C correlation points between C5 and H4 made it possible to assign the halogen position. MS (CID, $NH_3$) m/z: 385 (MH$^+$). Analysis (%) for $C_{20}H_{14}Cl_2N_2O_2 \cdot 0.1Na_2SO_4$: calculated C, 60.14; H, 3.53; N, 7.01. found C, 59.92; H, 2.58; N, 6.65. UV/vis [dioxane/20 mM Tris-HCl pH=7.4 containing 150 mM NaCl (1/1, v/v)]: λ nm (ε M$^{-1}$ cm$^{-1}$)=254 (75,000), 313 (7,200).

2,2'-(1,2-Ethanediyl)-bis(5-chloro-7-iodo-8-hydroxyquinoline) (Compound 9)

The protocol was established from works by: H. Gershon et al., *J. Heterocycl. Chem.* 1972, 9, 659-666. 250µλ of 97% $H_2SO_4$ is added to a solution of 8 (300 mg; 0.78 mmol) in 12 ml of methanol, under $N_2$, to yield a yellow suspension which is cooled over an ice bath. N-iodosuccinimide (418 mg; 1.86 mmol) is then added slowly and the mixture is stirred for 15 minutes at 0° C. then for 5 days at ambient temperature. It is subsequently poured over ice and decoloured by adding $Na_2S_{25}$ (450 mg). The suspension is neutralised with ammonia and centrifuged. The supernatant is removed, the precipitate is dissolved in dichloromethane and washed with Tris-HCl (0.1 M=7.0) buffer. The solvent from the organic phase is evaporated under vacuum to yield 9 in the form of a yellow powder (350 mg; 0.55 mmol, yield=70%). NMR-$^1$H (250 MHz, DMSO-$d_6$) δ, ppm: 8.36 (d, $^3$J (H, H)=8.5 Hz, 2H); 7.90 (s, 2H); 7.70 (d, $^3$J (H, H)=8.7 Hz, 2H); 3.68 (s, 4H). NMR-$^{13}$C (63 MHz, DMSO-$d_6$) δ, ppm: 162.1 (Cq); 153.1 (Cq); 137.3 (CH); 134.4 (Cq); 133.5 (CH); 124.6 (Cq); 124.5 (CH); 120.2 (CH); 78.4 (CH); 37.1 ($CH_2$). MS (CID, $NH_3$) m/z: 637 (MH$^+$). Analysis (%) for $C_{20}H_{14}Cl_2I_2N_2O_2$: calculated C, 37.71; H, 1.90; N, 4.40. found C, 38.15; H, 2.04; N, 4.15. UV/vis [dioxane/20 mM Tris-HCl pH=7.4 containing 150 mM NaCl (1/1, v/v)]: λ nm (ε M$^{-1}$ cm$^{-1}$)=262 (69,500), 319 (7,900).

2,2',2''-(1,2,3-Propanetriyl)-tris[8-(methyloxy)quinoline] (Compound 11')

A 1.5 M solution of lithium diisopropylamine THF in cyclohexane (20 ml; 30.52 mmol) is added to a solution of 8-methyloxyquinaldine (1.41 g; 8.14 mmol) in dry THF (20 ml), under argon and cooled over an ice bath, for a period of 1 minute. The solution is stirred for 1 hour at 4° C. then dry $CuCl_2$ (1.32 g; 9.81 mmol) is added and the mixture is stirred for 36 hours at ambient temperature under argon. Water (100 ml) is then added and the product is extracted with chloroform, washed with brine and the solvent is evaporated. The product is then subjected to silica gel column chromatography eluted with a gradient of 20 to 100% of ethyl acetate in $CHCl_3$ (v/v). The resulting product is dissolved in dichloromethane and washed with an EDTA aqueous solution to remove any traces of copper ion, then subjected to chromatography again, according to the earlier conditions, to yield 2,2',2''-(1,2,3-propanetriyl)-tris[8-(methyloxy)quinoline] in the form of a white powder (150 mg; 0.29 mmol, yield=11%). NMR-$^1$H (250 MHz, $CDCl_3$) δ, ppm: 7.81 (d, $^3$J (H, H)=8.5 Hz, 1H); 7.75 (d, $^3$J (H, H)=8.5 Hz, 2H); 7.37-7.18 (m, 9 H), 7.00 (dd, $^3$J (H, H)=7.5 Hz, $^4$J (H, H)=1.5 Hz, 1H); 6.95 (dd, $^3$J (H, H)=7.5 Hz, $^4$J (H, H)=1.5 Hz, 1H); 4.49 (ABX system, $^3$J$_{AB}$ (H, H)=8.0 Hz, $^3$J$_{BX}$ (H, H)=7.0 Hz, 1H); 4.05 (s, 3H); 4.01 (s, 6H); 3.78 (ABX system, $^2$J$_{AB}$ (H, H)=14.0 Hz, $^3$J$_{AX}$ (H, H)=8.0 Hz, 2H); 3.62 (ABX system, $^2$J$_{AB}$ (H, H)=14.0 Hz, $^3$J$_{BX}$ (H, H)=7.0 Hz, 2H). MS (CDI, $NH_3$): m/z=516 (MH$^+$).

2,2',2''-(1,2,3-Propanetriyl)-tris(8-hydroxyquinoline) (Compound 11)

2,2',2''-(1,2,3-propanetriyl)-tris[8-(methyloxy)quinoline] (30 mg; 0.058 mmol) is heated under reflux in hydrobromic acid at 48% (1.2 ml) for 36 hours. The acid is evaporated under vacuum and the residue is dissolved in a mixture of 10 ml of $CH_2Cl_2$ and 10 ml of sodium acetate buffer (0.1 M; pH=7.0). The organic phase is collected and the aqueous phase is subsequently extracted with $CH_2Cl_2$ (2×10 ml). The organic phases are combined, washed in water (10 ml), and the solvent subsequently evaporated under vacuum to yield 11 in the form of an orange powder (20 mg; 0.042 mmol; yield=73%). NMR-$^1$H (250 MHz, $CDCl_3$) δ, ppm: 7.94 (d, $^3$J (H, H)=8.0 Hz, 1H); 7.91 (d, $^3$J (H, H)=8.0 Hz, 2H); 7.42-7.10 (m, 12 H); 4.47 (ABX system, $^3$J$_{AX}$(H, H)=8.0 Hz, $^3$J$_{BX}$(H, H)=6.5 Hz, 1H); 3.71 (ABX system, $^2$J$_{AB}$(H, H)=14.5 Hz, $^3$J$_{AX}$(H, H)=8.0 Hz, 2H); 3.57 (ABX system, $^2$J$_{AB\,(H, H)}$=14.5 Hz, $^3$J$_{BX}$ (H, H)=6.5 Hz, 2H). MS (CDI, $NH_3$): m/z=474 (MH$^+$). Analysis (%) for $C_{30}H_{23}N_3O_3 \cdot 0.5H_2O$: calculated C, 74.67; H, 5.01; N, 8.71. found C, 74.54; H, 5.09; N, 9.19.

UV/vis [CH$_3$OH/20 mM tris.HCl pH=7.4 containing 150 mM NaCl (1/1, v/v)]: λ nm (ε M$^{-1}$ cm$^{-1}$)=204 (106,000), 248 (113,000), 302 (9,200).

Bis(8-quinoline)amine (Compound 12)

It was prepared according to J. C. Peters et al., *Inorg. Chem.* 2001, 40, 5083-5091. In summary: a suspension under argon of tris(dibenzylidene-acetone)-dipalladium(0) (4.4 mg, 5 µmol) and rac-2,2'-bis(diphenylphosphino)-1,1',binaphthyl (6.0 mg, 10 µmol) in 750 µl of toluene is stirred for 5 minutes at ambient temperature then 8-bromoquinoline (50 mg, 0.24 mmol), 8-aminoquinoline (35 mg, 0.24 mmol) and 1.75 ml of toluene are added to the suspension. By adding tertio-sodium butanolate (28 mg; 0.29 mmol), a red solution is formed and this is stirred for 3 days at 110° C. After cooling, the solution is filtered over silica and extracted using dichloromethane. The organic phase is concentrated to yield a red solid, which is purified by silica gel chromatography eluted by means of a toluene/ethyl acetate (4/1, v/v) mixture to yield 12 in the form of an orange solid (44.0 mg, 0.16 mmol, yield=67%). NMR-$^1$H (250 MHz, CDCl$_3$) δ, ppm: 10.62 (s large, 1H); 8.96 (dd, $^3$J (H, H)=4.0 Hz, $^4$J (H, H)=1.5 Hz, 2H); 8.16 (dd, $^3$J (H, H)=8.5 Hz, $^4$J (H, H)=1.5 Hz, 2H); 7.90 (dd, $^3$J (H, H)=7.5 Hz, $^4$J (H, H)=1.0 Hz, 2H); 7.53 (m, 2H); 7.46 (m, 2H); 7.34 (dd, $^3$J (H, H)=6.5 Hz, $^4$J (H, H)=1.0 Hz, 2H). MS (CDI, NH$_3$): m/z=272 (MH$^+$). UV/vis [DMSO/20 mM Tris-HC pH=7.4 containing 150 mM NaCl (1/1, v/v)]: λ nm (ε M$^{-1}$ cm$^1$)=268 (43,700), 341 (5,100), 399 (16,900).

N,N'-di-8-quinolinyl-1,3-propanediamine (Compound 13)

A suspension under argon of tris(dibenzylideneacetone)dipalladium(0) (55 mg, 0.06 mmol) and rac-2,2'-bis(diphenylphosphino)-1,1',binaphthyl (75 mg, 0.12 mmol) in 6 ml of toluene is stirred for 5 minutes at ambient temperature then 8-bromoquinoline (500 mg, 314 µl, 2.40 mmol), 1,3-diaminopropane (89 mg, 100 µl, 1.20 mmol) and 6 ml of toluene are added to the suspension. By adding tertio-sodium butanolate (323 mg; 3.36 mmol), a red solution is formed and this is stirred for 3 days at 100° C. After cooling, the solution is filtered over silica and extracted using dichloromethane. The organic phase is concentrated to yield a violet solid which is purified by silica gel chromatography eluted with a gradient of 0 to 5% of CH$_3$OH in CH$_2$Cl$_2$ (v/v). After the solvent has evaporated, the product is taken up in dichloromethane and precipitated at 4° C. by adding 4 equivalents of HCl (in the form of a 1 M solution in diethyl ether). The precipitate is recovered and dissolved again in water, the solution is alkalinised using ammonia until the pH=10, and the product is extracted with dichloromethane to yield, after evaporation of the solvent and drying under vacuum, 13 in the form of a brown powder (355 mg, 1.08 mmol, yield=90%). NMR-$^1$H (250 MHz, CDCl$_3$) δ, ppm: 8.70 (dd, $^3$J (H, H)=4.0 Hz, $^4$J (H, H)=1.5 Hz, 2H); 8.06 (dd, $^3$J (H, H)=8.0 Hz, $^4$J (H, H)=1.5 Hz, 2H); 7.37 (m, 4H); 7.05 (dd, $^3$J (H, H)=8.0 Hz, $^4$J (H, H)=0.5 Hz, 2H); 6.71 (dd, $^3$J (H, H)=8.0 Hz, $^4$J (H, H)=0.5 Hz, 2H); 6.24 (t large, $^3$J (H, H)=5.0 Hz, 2H); 3. 55 (m, 4H); 2.27 (quintuplet, $^3$J (H, H)=7.0 Hz, 2H). NMR-$^{13}$C (126 MHz, CDCl$_3$) δ, ppm: 146.8 (CH); 144.8 (Cq); 138.3 (Cq); 136.0 (CH); 128.7 (Cq); 127.8 (CH); 121.4 (CH); 113.8 (CH); 104.7 (CH); 41.3 (CH$_2$); 29.0 (CH$_2$). MS (CDI, NH$_3$): m/z=329 (MH$^+$).

N,N'-bis(2-methyl-8-quinolinyl)-1,2-ethanediamine (Compound 14)

A solution under argon of 8-aminoquinaldine (0.50 g; 3.16 mmol) in 5 ml of dry THF is cooled to −90° C. by means of a methanol/liquid nitrogen mixture. A 1.5 M solution of lithium diisopropylamine THF in cyclohexane (4.2 ml; 6.33 mmol) in 7.5 ml of THF is added over 30 minutes. The solution is stirred for a further 90 minutes at −95° C., then 1,2-dibromoethane (0.55 ml; 6.33 mmol) is added dropwise. The mixture is brought to ambient temperature and stirred for 15 hours. Water (6 ml) is then added and the mixture is stirred for 90 minutes at ambient temperature. The THF is evaporated under reduced pressure and the aqueous phase is extracted with CH$_2$Cl$_2$ (2×75 ml). The organic phase is washed with 75 ml of a saturated aqueous solution of NaHCO$_3$ then with 75 ml of H$_2$O and the solvent is evaporated under reduced pressure. The crude product of the reaction is then subjected to silica gel column chromatography, eluted with a gradient of 0 to 100% of ethyl acetate in CH$_2$Cl$_2$ (v/v). Fractions containing the product are combined and the solvent is evaporated. The product is dissolved again in 1 ml of CH$_2$Cl$_2$ and precipitated by adding 6 ml of hexane. It is subsequently filtered then rinsed in hexane to yield, after drying under vacuum, 14 in the form of a white powder (34 mg; 0.10 mmol; yield=6%). NMR-$^1$H (250 MHz, CDCl$_3$) δ, ppm: 7.95 (d, $^3$J (H, H)=8.5 Hz, 2H); 7.33 (m. 2H); 7.24 (d, $^3$J (H, H)=8.5 Hz, 2H); 7.03 (d, $^3$J (H, H)=8.0 Hz, 2H); 6.78 (d, $^3$J (H, H)=7.5 Hz, 2H); 6.45 (s large, 2H); 3.75 (m, 4H), 2.68 (s, 6H). NMR-$^{13}$C 126 MHz: CDCl$_3$) δ, ppm: 155.7; 144.1; 137.5; 136.2; 126.8; 126.7; 122.2; 114.0; 105.0; 42.8; 25.0. MS (CID, NH$_3$): m/z=343 (MH$^+$). Analysis (%) for C$_{22}$H$_{22}$N$_4$.0.3CH$_2$Cl$_2$: calculated C, 72.80; H, 6.19; N, 15.23. found C, 72.41; H, 6.02; N, 14.87. UV/vis [CH$_3$OH/20 mM Tris-HCl pH=7.4 containing 150 mM NaCl (1/1, v/v)]: λ nm (ε M$^{-1}$ cm$^{-1}$)=254 (44, 200), 341 (6,000).

8,8'-Oxydiquinoline (Compound 15)

The product has already been described in: V. M. Dziomko et al., *Yakugaku Zasshi* 1951, 71, 452-455; but using a different method of synthesis. Caesium carbonate (156 mg; 0.48 mmol), 8-bromoquinoline (32 µl; 50 mg; 0.24 mmol) and CuCl$_2$.2H$_2$O (4.1 mg; 0.024 mmol) are added to a solution under argon of 8-hydroxyquinoline (71 mg; 0.49 mmol) in 2.0 ml of dry DMF. The mixture is heated under reflux for 72 hours. After cooling, 5 ml of CH$_2$Cl$_2$ and 5 ml of a 0.12 M aqueous solution of EDTA disodium salt are added. The organic phase is recovered and the aqueous phase is subsequently extracted with CH$_2$Cl$_2$ (2×5 ml). The organic phases are combined and washed once with 5 ml of 0.12 M EDTA in H$_2$O then in water. The volume is reduced under reduced pressure then the reaction crude product is purified by silica gel chromatography, eluted with a gradient of 50 to 100% of ethyl acetate in toluene (v/v) then with 100% of CH$_3$OH and the solvent is evaporated to recover 15, from the methanol phase, in the form of a white powder (13 mg; 0.046 mmol, yield=19%). NMR-$^1$H (250 MHz, CDCl$_3$) δ, ppm: 8.95 (dd, $^3$J (H, H)=4.0 Hz, $^4$J (H, H)=1.5 Hz, 2H); 8.21 (dd, $^3$J (H, H)=8.5 Hz, $^4$J (H, H)=1.5 Hz, 2H); 7.61 (dd, $^3$J (H, H)=8.0 Hz, $^4$J (H, H)=1.0 Hz, 2H); 7.46 (dd, $^3$J (H, H)=4.0 Hz and 8.5 Hz, 2H); 7.42 (dd, $^3$J (H, H)=7.5 Hz and 8.0 Hz, 2H); 7.14 (dd, $^3$J (H, H)=7.5 Hz, $^4$J (H, H)=1.0 Hz, 2H). MS (CID, NH$_3$): m/z=273 (MH$^+$). UV/vis [CH$_3$OH/20 mM Tris-HCl pH=7.4 containing 150 mM NaCl (1/1, v/v)]: λ nm (ε M$^{-1}$ cm$^{-1}$)=232 (53,300), 240 (42,900), 2994 (9,400), 327 (5,800, shoulder).

7-Methyloxy-8-hydroxyquinoline

It was prepared using protocols by D. Planchenault et al. *Tetrahedron* 1995, 51, 5823-5830; D. Nobel, *J. Chem. Soc., Chem. Commun.* 1993, 419-420 and M. Numazawa et al. *J.*

Chem. Soc., Chem. Commun. 1983, 533-534. A solution of $CH_3ONa$ (30% by weight) in $CH_3OH$ (17 ml, 89.30 mmol) is added to a solution of 7-bromo-8-hydroxyquinoline (2.00 g; 8.93 mmol), in 125 ml of DMF. The mixture is stirred for 10 minutes under argon. $CuCl_2.2H_2O$ (0.46 g; 2.68 mmol) is added and the reaction mixture is heated under reflux for 20 hours. After cooling to ambient temperature, water (100 ml) and disodium EDTA dihydrate (7.83 g; 26.80 mmol) are added and the mixture is stirred for 1 hour. The solution is acidified to pH=4-5 with $CH_3COOH$ (3 ml) and it is subsequently basified gently with a saturated aqueous solution of $NaHCO_3$. The aqueous phase is extracted with $CH_2Cl_2$ (3×100 ml). The combined organic phases are dried over anhydrous $Na_2SO_4$ and concentrated under reduced pressure. The solid obtained is purified by silica gel chromatography, eluted using a gradient of $CH_2Cl_2/CH_3OH/CH_3COOH$ (94/4/2, v/v) to $CH_2Cl_2/CH_3OH$ (90/10, v/v). The fractions containing the product are combined and washed with a saturated aqueous solution of $NaHCO_3$ (3×100 ml). The organic phase is dried over anhydrous $Na_2SO_4$ and concentrated under reduced pressure to yield 7-methyloxy-8-hydroxyquinoline in the form of a white powder (0.65 g; 3.68 mmol, yield=40%). NMR-$^1H$ (250 MHz, $CDCl_3$) δ, ppm: 8.77 (dd, $^3J$ (H, H)=4.0 Hz, $^4J$ (H, H)=1.5 Hz, 1H); 8.11 (dd, $^3J$ (H, H)=8.5 Hz, $^4J$ (H, H)=1.5 Hz, 1H); 7.36 (m, 2H), 7.31 (dd, $^3J$ (H, H)=8.5 Hz, $^3J$ (H, H)=4.0 Hz, 1H), 4.06 (s, 3H). NMR-$^{13}C$ (63 MHz, $CDCl_3$) δ, ppm: 148.6 (CH); 144.0 (Cq); 139.7 (Cq); 138.6 (CH); 136.0 (Cq); 123.5 (CH); 119.7 (CH); 117.7 (CH); 116.4 (CH); 57.3 ($CH_3$). MS (CID, $NH_3$): m/z=176 ($MH^+$). Analysis (%) for $C_{10}H_9NO_2.0.1H_2O$: calculated C, 67.86; H, 5.24; N, 7.91. found C, 67.82; H, 5.11; N, 7.95.

7-(Methyloxy)-8-[(phenylmethyl)oxy]quinoline

7-Methyloxy-8-hydroxyquinoline (1.10 g; 6.29 mmol) and $K_2CO_3$ (1.30 g; 9.43 mmol) in 30 ml of dry acetonitrile are stirred for 10 minutes under argon. Benzyl chloride (0.87 ml, 7.54 mmol) is then added and the reaction medium is heated under reflux overnight. After returning to ambient temperature, the precipitate is filtered, washed with $CH_2Cl_2$ and the filtrate is concentrated under reduced pressure. The oil obtained is dissolved again in $CH_2Cl_2$ (50 ml) and washed in succession with an aqueous solution of NaOH 2 N (4×50 ml) and water (1×50 ml). The organic phase is dried over anhydrous $Na_2SO_4$ and the solvent is evaporated under reduced pressure to yield 7-methyloxy-8-[(phenylmethyl)oxy]quinoline in the form of a brown oil (1.28 g; 4.84 mmol, yield=77%). NMR-$^1H$ (250 MHz, $CDCl_3$) δ, ppm: 8.94 (dd, $^3J$ (H, H)=4.0 Hz, $^4J$ (H, H)=1.5 Hz, 1H); 8.06 (dd, $^3J$ (H, H)=8.5 Hz, $^4J$ (H, H)=1.5 Hz, 1H); 7.59-7.51 (m, 3H); 7.36-7.24 (m, 5H); 5.40 (s, 2H); 3.92 (s, 3H). NMR-$^{13}C$ (63 MHz, $CDCl_3$) δ, ppm: 151.3 (CH); 149.5 (Cq); 142.9 (Cq); 141.2 (Cq); 137.4 (Cq); 135.3 (CH); 127.9 (CH); 127.4 (CH); 127.1 (CH); 123.6 (Cq); 122.9 (CH); 118.5 (CH) 114.8 (CH); 75.2 ($CH_2$); 56.1 ($CH_3$). MS (CID, $NH_3$): m/z=266 ($MH^+$). Analysis (%) for $C_{17}H_{15}NO_2.0.05 CHCl_3$: calculated C, 75.49; H, 5.59; N, 5.16. found C, 75.74; H, 5.40; N, 5.33.

7-(Methyloxy)-8-[(phenylmethyl)oxy]quinoline-N-oxide 7-(methyloxy)-8-[(phenylmethyl)oxy]quinoline (0.30 g; 1.13 mmol) and 77% by weight m-chloroperbenzoic acid (0.38 g; 1.69 mmol) are added in succession to dry $CH_2Cl_2$ (11 ml) at 4° C. under argon. The mixture is stirred for 48 hours at ambient temperature, then $CH_2Cl_2$ (40 ml) is added. The reaction medium is washed with a saturated aqueous solution of $NaHCO_3$ (2×50 ml) and the solvent is evaporated under reduced pressure. The resulting oil is purified by silica gel chromatography, eluted with a $CH_2Cl_2/CH_3OH$ (95/5, v/v) mixture to yield 7-(methyloxy)-8-[(phenylmethyl)oxy]quinoline-N-oxide in the form of a yellow oil (0.18 g; 0.64 mmol, yield=58%). NMR-$^1H$ (250 MHz, $CDCl_3$) δ, ppm: 8.43 (dd, $^3J$ (H, H)=6.0 Hz, $^4J$ ((H, H)=1.0 Hz, 1H); 7.68-7.58 (m, 4H); 7.41-7.30 (m, 4H); 7.10 (dd, $^3J$ (H, H)=8.5 Hz, $^3J$ (H, H)=6.0 Hz, 1H); 5.23 (s, 2H); 3.96 (s, 3H). NMR-$^{13}C$ (63 MHz, $CDCl_3$) δ, ppm: 138.4; 128.9; 128.7; 128.2; 127.8; 127.6; 125.7; 124.9; 123.4; 119.5; 118.8; 116.8; 107.7; 75.2; 57.1. MS (CID, $NH_3$): m/z=282 ($MH^+$). Analysis (%) for $C_{17}H_{15}NO_3$: calculated C, 72.58; H, 5.37; N, 4.98. found C, 72.74; H, 4.91; N, 4.87.

Dimethyl bis{7-(methyloxy)-8-[phenylmethyl)oxy]-2-quinolinyl}propanedioate (Compound 16')

The protocol was established from synthesis of 1". 7-(methyloxy)-8-[(phenylmethyl)oxy]quinoline-N-oxide (0.72 g; 2.56 mmol) is dissolved in dry $CH_2Cl_2$ (7 ml). Dimethylmalonate (0.307 ml, 2.69 mmol) and acetic anhydride (1.18 ml) are then added to said solution and the mixture is stirred for 24 days at ambient temperature, away from light and protected from humidity (by means of a $CaCl_2$ tube). $CH_3OH$ (20 ml) is added and, after 15 hours at −20° C., a precipitate is removed by centrifugation. The solvent from the supernatant is evaporated and the crude reaction product is dissolved again in $CH_3OH$ (0.5 ml) and precipitated by adding water (3 ml). The supernatant is removed and the precipitate is taken up in 40 ml of $CH_2Cl_2$ and washed in water (2×20 ml). After the solvent has evaporated, the product is purified by means of preparative thin-layer chromatography, eluted with a $CH_2Cl_2/CH_3OH$ (99/1, v/v) mixture. Residual impurities are removed by crystallisation in $CH_3OH$ to yield dimethyl bis{7-(methyloxy)8-[phenylmethyl)oxy]-2-quinolinyl}propanedioate in the form of white crystals (12 mg; 0.02 mmol, yield=1.5%). NMR-$^1H$ (250 MHz, $CDCl_3$) δ, ppm: 7.93 (d, $^3J$ (H, H)=8.5 Hz, 2H); 7.63 (d, $^3J$ (H, H)=8.5 Hz, 2H); 7.59 (m, 4H); 7.47 (d, $^3J$ (H, H)=9.0 Hz, 2H); 7.40-7.28 (m, 8H); 5.41 (s, 4H); 3.95 (s, 6H); 3.84 (s, 6H). NMR-$^{13}C$ (63 MHz, $CDCl_3$) δ, ppm: 169.3 (CH); 157.5 (Cq); 152.2 (Cq); 142.1 (Cq); 142.1 (Cq); 138.2 (Cq); 135.9 (CH); 128.4 (CH); 128.2 (CH); 127.7 (Cq); 123.2 (CH); 123.0 (CH) 121.1 (CH); 115.9 (CH); 75.8 ($CH_2$); 75.2 (Cq); 57.1 ($CH_3$); 53.0 ($CH_3$). MS (CID, $NH_3$): m/z=659 ($MH^+$). The molecule structure was confirmed by X-ray diffraction analysis of monocrystals obtained by crystallisation of the product in methanol. The structure of the complex is presented in FIG. 4. The parameters of the crystal analysis are as follows: monoclinic crystal system; P 1 21 1; a=10.2593 (9) Å, b=10.8311 (10) Å, c=15.2192(14) Å, α=90°, β=97.622(5)°, γ=90°.

2,2'-(methanediyl)-bis(7-methyloxy-8-hydroxy-2-quinolinium)dichloride (Compound 16)

The protocol was established from synthesis of 1'. Dimethyl bis{7-(methyloxy)8-[phenylmethyl)oxy]-2-quinolinyl}propanedioate (40 mg; 0.06 mmol) is heated under reflux in 37% aqueous HCl (3 ml) for 1 hour 30 minutes. After cooling, the solvent is evaporated under reduced pressure. The product obtained is solubilised in $CH_3OH$ and poured over 3 ml of diethyl ether. After centrifugation, the precipitate obtained is washed with 3 ml of diethyl ether then dried under vacuum to yield 16 in the form of a yellow powder (28 mg; 0.06 mmol, yield=98%). NMR-$^1H$ (250 MHz, $CD_3OD$) δ, ppm: 8.97 (d, $^3J$ (H, H)=7.5 Hz, 2H), 7.86 (s, 4H);

7.68 (d, $^3$J (H, H)=8.0 Hz, 2H); 4.16 (s, 6H). MS (DCl, NH$_3$): m/z=363 (MH$^+$). UV/vis [CH$_3$OH/20 mM Tris-HCl pH=7.4 containing 150 mM NaCl (1/1, v/v)]: λ nm (ε M$^{-1}$ cm$^{-1}$)=203 (47,800), 246 (34,100, shoulder), 257 (49,800), 334 (3,500).

7-bromo-2-methyl-8-hydroxyquinoline

The protocol was established from works by: D. E. Pearson et al. *J. Org. Chem.* 1967, 2358-2360. tert-butylamine (3.23 ml, 30.78 mmol) is stirred under argon in 100 ml of toluene for 2 hours at ambient temperature in the presence of an activated 4 Å molecular sieve (10 g). After cooling to −70° C., N-bromosuccinimide (5.48 g; 30.78 mmol) and 2-methyl-8-hydroxyquinoline (5.00 g; 30.78 mmol) are added in succession. The mixture is slowly brought to ambient temperature (approximately 4 hours). The reaction medium is filtered and the molecular sieve is washed with diethyl ether (20 ml). The filtrate is washed in water (3×50 ml), dried over anhydrous Na$_2$SO$_4$ and the organic phase is concentrated to yield a solid which is brought to reflux in 100 ml of hexane for 1 hour. After 24 hours at ambient temperature, the precipitate is filtered and dried under vacuum to yield 7-bromo-2-methyl-8-hydroxyquinoline in the form of a white powder (4.85 g; 20.47 mmol, yield=67%). NMR-$^1$H (250 MHz, CDCl$_3$) δ, ppm: 8.00 (d, $^3$J (H, H)=8.5 Hz, 1H); 7.52 (d, $^3$J (H, H)=9.0 Hz, 1H); 7.31 (d, $^3$J (H, H)=8.5 Hz, 1H); 7.16 (d, $^3$J (H, H)=9.0 Hz, 1H); 2.72 (s, 3H). NMR-$^{13}$C (63 MHz, CDCl$_3$) δ, ppm: 157.9; 149.2; 137.7; 136.2; 130.1; 125.4; 122.9; 118.2; 103.9; 24.8. MS (CID, NH$_3$): m/z=238 (MH$^+$). Analysis (%) for C$_{10}$H$_8$BrNO: calculated C, 50.45; H, 3.39; N, 5.88. found C, 50.02; H, 3.37; N, 6.12.

2-methyl-7-(methyloxy)-8-quinolinol

The protocol was established using works by: D. Planchenault et al. *Tetrahedron* 1995, 51, 5823-5830. A solution of CH$_3$ONa (30% by weight) in CH$_3$OH (8.04 ml; 42.2 mmol) is added to a solution of 7-bromo-2-methyl-8-hydroxyquinoline (1.00 g; 4.22 mmol) in DMF (60 ml). The mixture is stirred for 10 minutes under argon. CuCl$_2$.2H$_2$O (0.22 g; 1.27 mmol) is added and the reaction mixture is heated under reflux for 30 hours. After cooling, water (50 ml) and disodium EDTA dihydrate (10 g; 27 mmol) are added and the medium is stirred for 1 hour. The solution is lightly acidified with acetic acid (3 ml, pH=4-5) and subsequently rebasified gently with a saturated aqueous solution of NaHCO$_3$ (3 ml). The aqueous phase is extracted with CH$_2$Cl$_2$ (3×100 ml). The combined organic phases are dried over anhydrous Na$_2$SO$_4$ and concentrated under reduced pressure. The solid obtained is purified by silica gel chromatography, eluted using a gradient of CH$_2$Cl$_2$/CH$_3$OH/CH$_3$COOH (94/4/2, v/v) to CH$_2$Cl$_2$/CH$_3$OH/CH$_3$COOH (94/5/1, v/v) then to CH$_2$Cl$_2$/CH$_3$OH (94/6, v/v). Fractions containing the product are combined and washed with a saturated aqueous solution of NaHCO$_3$ (3×100 ml). The organic phase is dried over anhydrous Na$_2$SO$_4$ and concentrated under reduced pressure to yield 2-methyl-7-(methyloxy)-8-quinolinol in the form of a white powder (480 mg; 2.54 mmol, yield=60%). NMR-$^1$H (250 MHz, CDCl$_3$) δ, ppm: 7.95 (d, $^3$J (H, H)=8.5 Hz, 1H); 7.26 (s, 2H); 7.15 (d, $^3$J (H, H)=8.5 Hz, 1H); 4.03 (s, 3H); 2.69 (s, 3H). NMR-$^{13}$C (63 MHz, CDCl$_3$) δ, ppm: 157.6 (Cq); 143.9 (Cq); 139.3 (Cq); 138.0 (Cq); 136.0 (CH); 121.7 (Cq); 120.6 (CH); 117.3 (CH); 115.2 (CH); 57.2 (CH$_3$); 25.1 (CH$_3$). MS (CID, NH$_3$): m/z=190 (MH$^+$). Analysis (%) for C$_{11}$H$_{11}$NO$_2$: calculated C, 69.83; H, 5.86; N, 7.40. found C, 69.40; H, 5.85; N, 7.47.

2,2'-(1,2-ethanediyl)-bis[7-(methyloxy)-8-quinolinol] (Compound 17)

The protocol was established from synthesis of 7'. 2-methyl-7-(methyloxy)-8-quinolinol (0.50 g, 2.64 mmol) is stirred under argon in 10 ml of distilled THF for 30 minutes at ambient temperature in the presence of an activated 4 Å molecular sieve (2.0 g). After cooling to −90° C., a 1.5 M solution of LDA-THF in cyclohexane (3.70 ml, 5.56 mmol) is added dropwise over a 10-minute period. The mixture is subsequently slowly brought to −50° C., then cooled again to −90° C. 1,2-dibromoethane (0.50 ml; 5.82 mmol) is added and the mixture is brought to ambient temperature in the presence of the cold bath (4 hours). Water (5 ml) and CH$_3$COOH (0.50 ml, pH=4-5) are added and the medium is stirred for 1 hour. The molecular sieve is removed by filtration and is washed in succession with a saturated aqueous solution of NaHCO$_3$ (10 ml), water (10 ml) and diethyl ether (40 ml). The biphasic filtrate is transferred to a separating funnel and the organic phase collected. The aqueous phase is extracted with diethyl ether (3×50 ml) and the combined organic phases are dried over anhydrous Na$_2$SO$_4$ and concentrated under reduced pressure. The resulting solid is dissolved hot in CH$_3$OH (10 ml) and the white precipitate formed is collected after 3 days, yielding pure 17 after drying under vacuum (306 mg; 0.81 mmol, yield=62%). NMR-$^1$H (250 MHz, CDCl$_3$) δ, ppm: 8.00 (d, $^3$J (H, H)=8.5 Hz, 2H); 7.28 (s, 4H); 7.24 (d, $^3$J (H, H)=8.5 Hz, 2H); 4.04 (s, 6H); 3.57 (s, 4H). NMR-$^{13}$C (63 MHz, CDCl$_3$) δ, ppm: 160.1 (Cq); 144.0 (Cq); 139.3 (Cq); 137.9 (Cq); 136.3 (CH); 121.9 (Cq); 120.4 (CH); 117.5 (CH); 115.5 (CH); 57.2 (CH$_3$); 37.1 (CH$_2$). MS (CID, NH$_3$): m/z=377 (MH$^+$). Analysis (%) for C$_{22}$H$_{20}$N$_2$O$_4$.0.2H$_2$O: calculated C, 69.53; H, 5.41; N, 7.37. found C, 69.40; H, 5.30; N, 7.47. UV/vis [CH$_3$OH/20 mM Tris-HCl pH=7.4 containing 150 mM NaCl (1/1, v/v)]: λ nm (ε M$^{-1}$ cm$^{-1}$)=204 (83,000), 208 (53,200, shoulder), 252 (97,200), 338 (6,600).

8-hydroxy-N-(8-hydroxy-2-quinolinyl)-2-quinolinecarboxamide (Compound 18)

1-hydroxybenzotriazole monohydrate (71 mg; 0.53 mmol), (benzotriazol-1-yloxy)tris(dimethylamino)phosphonium hexafluorophosphate (177 mg; 0.40 mmol) and triethylamine (0.037 ml; 0.26 mmol) are added to a suspension of 8-hydroxyquinoline-2-carboxylic acid (50 mg; 0, 26 mmol) in 5 ml of CH$_2$Cl$_2$. The mixture is stirred for 30 minutes at ambient temperature, then 2-amine-8-hydroxyquinoline (85 mg; 0.53 mmol) and triethylamine (0.037 ml; 0.26 mmol then, after stirring for 5 minutes, 0.117 ml; 0.794 mmol) are added. The mixture is stirred for 18 hours at ambient temperature, then 10 ml of H$_2$O and 5 ml of CH$_2$Cl$_2$ are added and the organic phase is recovered by decantation. The volume is reduced by evaporation under reduced pressure then the product is purified by silica gel chromatography, eluted with a CH$_2$Cl$_2$/CH$_3$OH (995/0.5, v/v) mixture and the solvent is evaporated under reduced pressure. The product is dissolved in 30 ml of CH$_2$Cl$_2$ and 30 ml of a saturated aqueous solution of NaHCO$_3$ are added. The product is extracted 3 times with CH$_2$Cl$_2$ then the organic phases are combined and the solvent is evaporated under reduced pressure to yield 18 in the form of a white powder (28 mg; 0.085 mmol, yield=32%). NMR-$^1$H (250 MHz, DMSO-d$_6$) δ, ppm: 11.89 (s, 1H); 10.89 (s, 1H); 9.55 (s, 1H); 8.60 (d, $^3$J (H, H)=8.5 Hz, 1H); 8.41 (s, 2H); 8.32 (d, $^3$J (H, H)=8.5 Hz, 1H); 7.63 (dd, $^3$J (H, H)=7.0 and 8.0 Hz, 1H); 7.53 (dd, $^3$J (H, H)=8.0 Hz, $^4$J (H, H)=1.0 Hz, 1H); 7.42 (dd, $^3$J (H, H)=8.0 Hz, $^4$J (H, H)=2.0 Hz, 1H); 7.37 (dd, $^3$J (H, H)=7.0 and 8.0 Hz, 1H); 7.23 (dd, $^3$J (H, H)=7.0 Hz, $^4$J (H, H)=1.0 Hz, 1H); 7.13 (dd, $^3$J (H, H)=7.0 Hz, $^4$J (H, H)=2.0 Hz, 1H). MS (CID, NH$_3$): m/z=332 (MH$^+$). UV/vis [DMSO/20 mM Tris-HCl pH=7.4 containing 150 mM NaCl (1/1, v/v)]: λ nm (ε M$^{-1}$cm$^{-1}$=259 (49,100), 332 (11,200, shoulder).

2-{[8-hydroxy-2-quinolinyl)amino]methyl}-8-quinolinol (Compound 19)

A solution of 2-amino-8-hydroxyquinoline (100 mg; 0.62 mmol) and 8-hydroxyquinoline-2-carboxaldehyde (130 mg; 0.75 mmol) in 8 ml of 1,2-dichloroethane is stirred for 1 hour at ambient temperature then (CH$_3$COO)$_3$BHNa (291 mg; 1.29 mmol) is added and stirring is continued for 90 minutes at ambient temperature. 50 ml of CH$_2$Cl$_2$ and 50 ml of a saturated aqueous solution of NaHCO$_3$ are then added. The organic phase is recovered then the aqueous phase is extracted with CH$_2$Cl$_2$ (2×120 ml). The organic phases are combined and dried over anhydrous Na$_2$SO$_4$, then the solvent is evaporated. The product is dissolved in 75 ml of CH$_2$Cl$_2$ and precipitated by adding a volume (75 ml) of hexane. The supernatant is recovered by filtration and the solvent is evaporated. The evaporation residue is purified by silica gel chromatography, eluted using a CH$_2$Cl$_2$/CH$_3$OH mixture (0.5 to 1% of CH$_3$OH; v/v) to yield after evaporation of the solvent 19 in the form of a beige powder (32 mg; 0.10 mmol; yield=16%). NMR-$^1$H (200 MHz, DMSO-d$_6$) δ, ppm: 9.79 (s, 1H); 8.55 (s, 1H); 8.29 (d, $^3$J (H, H)=8.5 Hz, 1H); 8.01 (t, $^3$J (H, H)=4.5 Hz, 1H); 7.93 (d, $^3$J (H, H)=9.0 Hz, 1H); 7.57 (d, $^3$J (H, H)=8.5 Hz, 1H); 7.39 (m, 2H); 7.08 (m, 4H); 6.91 (dd, $^3$J (H, H)=8.0 Hz, $^4$J (H, H)=1.5 Hz, 1H); 5.08 (d, $^3$J (H, H)=4.5 Hz, 2H). MS (FAB, MBA): m/z=318 (MH$^+$).

2,2'-(iminodimethanediyl)di(N-boc-8-quinolinyl amine) (Compound 20')

0.25 ml of a 7 M solution of NH$_3$ (1.75 mmol) in CH$_3$OH is added to a solution of 1,1-dimethyl(2-formyl-8-quinolinyl) carbamate (300 mg; 1.10 mmol) in 15 ml of 1,2-dichloroethane, and the mixture is stirred for 30 minutes at ambient temperature. (CH$_3$COO)$_3$BHNa (432 mg; 2.04 mmol) is added and stirring is continued for 15 hours at ambient temperature, then the solvent is evaporated under reduced pressure. The product is purified by silica gel chromatography, eluted with ethyl acetate to yield after evaporation of the solvent 2,2'-(iminodimethanediyl)di(N-boc-8-quinolinyl amine) in the form of a pale yellow powder (150 mg; 0.28 mmol, yield=52%). NMR-$^1$H (200 MHz, CDCl$_3$) δ, ppm: 8.98 (s large, 2H); 8.41 (d large, $^3$J (H, H)=7.0 Hz, 2H); 8.10 (d, $^3$J (H, H)=8.5 Hz, 2H); 7.53 (d, $^3$J (H, H)=8.5 Hz, 2H); 7.48 (dd, $^3$J (H, H)=8.0 and 7.5 Hz, 2H); 7.40 (dd, $^3$J (H, H)=8.0 Hz, $^4$J (H, H)=1.5 Hz, 2H); 4.25 (s, 4H); 2.21 (s large, 1H); 1.53 (s, 18H). NMR-$^{13}$C (50 MHz, CDCl$_3$) δ, ppm: 157.7 (Cq); 152.9 (Cq); 137.4 (Cq); 136.8 (CH); 134.8 (Cq); 127.1 (Cq); 126.9 (CH); 120.9 (CH); 120.0 (CH); 114.7 (CH); 80.4 (Cq); 54.9 (CH$_2$); 28.3 (CH$_3$). MS (CID, NH$_3$): m/z=530 (MH$^+$). Analysis (%) for C$_{30}$H$_{35}$N$_5$O$_4$.0.25 C$_4$H$_8$O$_2$: calculated C, 67.16; H, 6.77; N, 12.71. found C, 67.59; H, 7.10; N, 12.23.

2,2'-(iminodimethanediyl)di(8-quinolinyl amine) (Compound 20)

A solution of 2,2'-(iminodimethanediyl)di(N-boc-8-quinolinyl amine) (100 mg; 0.19 mmol) in 2.5 ml of CH$_2$Cl$_2$ and 2.5 ml trifluoroacetic acid is stirred for 45 minutes at ambient temperature then the solvents are evaporated under reduced pressure. Diethyl ether (10 ml) is added and the solvent is again evaporated. The product is taken up in 20 ml of CH$_2$Cl$_2$ and washed with a saturated aqueous solution of NaHCO$_3$ (2×40 ml). The organic phase is dried over anhydrous Na$_2$SO$_4$ then the solvent is evaporated under reduced pressure to yield 20 in the form of a beige powder (62 mg; 0.19 mmol, quantitative yield). NMR-$^1$H (250 MHz, CDCl$_3$) δ, ppm: 8.01 (d, $^3$J(H, H)=8.5 Hz, 2H); 7.40 (d, $^3$JH, H)=8.5 Hz, 2H); 7.29 (dd, $^3$J (H, H)=8.0 and 8.0 Hz, 2H); 7.13 (dd, $^3$J (H, H)=8.0, $^4$J (H, H)=1.0 Hz, 2H); 6.91 (d large, $^3$J (H, H)=8.0 Hz, 2H); 5.01 (s large, 4H); 4.22 (s, 4H); 2.60 (s large, 1H). NMR-$^{13}$C (50 MHz, CDCl$_3$) δ, ppm: 157.0 (Cq); 143.6 (Cq); 137.6 (Cq); 136.4 (CH); 127.7 (Cq); 126.8 (CH); 120.8 (CH); 115.9 (CH); 110.2 (CH); 54.9 (CH$_2$). MS (CID, NH$_3$): m/z=330 (MH$^+$).

2,2',2''-(nitrilotrimethanediyl)tri(N-boc-8-quinoline amine) (Compound 21')

30 µl of a 7 M solution of NH$_3$ (0.21 mmol) in CH$_3$OH is added to a solution of 1,1-dimethyl(2-formyl-8-quinolinyl) carbamate (50 mg; 0.18 mmol) in 2.5 ml of 1,2-dichloroethane, and the mixture is stirred for 5 minutes at ambient temperature. (CH$_3$COO)$_3$BHNa (72 mg; 0.34 mmol) is added and stirring is continued for 15 hours at ambient temperature. 10 ml of CH$_2$Cl$_2$ and 10 ml of a saturated aqueous solution of NaHCO$_3$ are then added, the organic phase is recovered then the aqueous phase is extracted with CH$_2$Cl$_2$ (2×10 ml). The organic phases are combined and dried over anhydrous Na$_2$SO$_4$, then the solvent is evaporated under reduced pressure. The product is purified by silica gel chromatography, eluted with CH$_2$Cl$_2$ to yield after evaporation of the solvent 2,2',2''-(nitrilotrimethanediyl)tri(N-boc-8-quinoline amine) in the form of a pale yellow powder (25 mg; 0.032 mmol, yield=52%). NMR-$^1$H (250 MHz, CDCl$_3$) δ, ppm: 9.03 (s, 3H); 8.39 (d large, $^3$J (H, H)=7.5 Hz, 3H); 8.11 (d, $^3$J (H, H)=8.5 Hz, 3H); 7.75 (d, $^3$J (H, H)=8.5 Hz, 3H); 7.47 (dd, $^3$J (H, H)=8.0 and 7.5 Hz, 3H); 7.38 (dd, $^3$J (H, H)=8.0 Hz, $^4$J (H, H)=1.5 Hz, 3H); 4.10 (s, 6H); 1.59 (s, 27 H). NMR-$^{13}$C (63 MHz, CDCl$_3$) δ, ppm: 157.8 (Cq); 152.9 (Cq); 137.3 (Cq); 136.7 (CH); 134.9 (Cq); 127.1 (Cq); 127.0 (CH); 121.4 (CH); 119.9 (CH); 114.6 (CH); 80.5 (Cq); 61.0 (CH$_2$); 28.4 (CH$_3$). MS (CID, NH$_3$): m/z=786 (MH$^+$).

2,2',2''-(nitrilotrimethanediyl)tri(8-quinoline amine) (Compound 21)

A solution of 2,2',2''-(nitrilotrimethanediyl)tri(N-boc-8-quinoline amine) (10 mg; 0.013 mmol) in 0.5 ml of CH$_2$Cl$_2$ and 0.5 ml of trifluoroacetic acid is stirred for 45 minutes at ambient temperature then the solvents are evaporated under reduced pressure. Diethyl ether (5 ml) is added and the solvent is again evaporated under reduced pressure. The product is taken up in 15 ml of CH$_2$Cl$_2$ and washed with a saturated aqueous solution of NaHCO$_3$ (2×10 ml). The organic phase is dried over anhydrous Na$_2$SO$_4$ then solvent is evaporated under reduced pressure to yield 21 in the form of a beige powder (6 mg; 0.013 mmol, quantitative yield). NMR-$^1$H (250 MHz, CDCl$_3$) δ, ppm: 8.05 (d, $^3$J(H, H)=8.5 Hz, 3H); 7.67 (d, large, $^3$J (H, H)=8.5 Hz, 3H); 7.29 (dd, $^3$J (H, H)=8.0 and 7.0 Hz, 3H); 7.12 (dd, $^3$J (H, H)=8.5 Hz, $^4$J (H, H)=1.0 Hz, 3H); 6.90 (d large, $^3$J (H, H)=7.0 Hz, 3H); 4.99 (s large, 6H); 4.08 (s large, 6H). MS (CID, NH$_3$): m/z=486 (MH$^+$).

[2-(butylamino)methyl]-N-boc-8-quinoline amine

The protocol was inspired by the works of G. Xue et al., *Tetrahedron* 2001, 57, 7623-7628, on other products. 1-butylamine (40 μl; 0.40 mmol) is added to a solution under argon of 1,1-dimethyl(2-formyl-8-quinolinyl)carbamate (50 mg; 0.18 mmol) in 2.5 ml of 1,2-dichloroethane and the mixture is stirred for 30 minutes at ambient temperature then $(CH_3COO)_3BHNa$ (72 mg; 0.34 mmol) is added and stirring is continued for 15 hours at ambient temperature. 10 ml of $CH_2Cl_2$ and 10 ml of a saturated aqueous solution of $NaHCO_3$ are then added, the organic phase is recovered then the aqueous phase is extracted with $CH_2Cl_2$ (2×10 ml). The organic phases are combined and dried over anhydrous $Na_2SO_4$, then the solvent is evaporated under reduced pressure to yield [2-(butylamino)methyl]-N-boc-8-quinoline amine in the form of an orange oil (39 mg; 0.12 mmol, yield=65%). NMR-$^1$H (250 MHz, $CDCl_3$) δ, ppm: 9.00 (s large, 1H); 8.39 (d large, $^3$J (H, H)=7.0 Hz, 1H); 8.08 (d, $^3$J (H, H)=8.5 Hz, 1H); 7.46 (dd, $^3$J (H, H)=8.5 and 7.0 Hz, 1H); 7.41 (dd, $^3$J (H, H)=8.5 Hz, $^4$J (H, H)=2.0 Hz, 1H); 7.39 (dd, $^3$J (H, H)=8.5 Hz, $^4$J (H, H)=1.5 Hz, 1H); 4.10 (s, 1H); 2.73 (t, $^3$J (H, H)=7.5 Hz, 2H); 2.13 (s large, 1H); 1.59 (s, 9H); 1.56 (m, 2H); 1.40 (m, 2H); 0.94 (t, $^3$J (H, H)=7.0 Hz, 3H).

2,2'-[(butylimino)dimethanediyl]di(N-boc-8-quinoline amine) (Compound 22')

A solution of [2-(butylamino)methyl]-N-boc-8-quinoline amine (39 mg; 0.12 mmol) and 1,1-dimethyl(2-formyl-8-quinolinyl)carbamate (36 mg; 0.13 mmol) in 2.5 ml of 1,2-dichloroethane is stirred for 30 minutes at ambient temperature then $(CH_3COO)_3BHNa$ (35 mg; 0.16 mmol) is added and stirring is continued for 20 hours at ambient temperature. 10 ml of $CH_2Cl_2$ and 10 ml of a saturated aqueous solution of $NaHCO_3$ are then added, the organic phase is recovered then the aqueous phase is extracted with $CH_2Cl_2$ (2×10 ml). The organic phases are combined and dried over anhydrous $Na_2SO_4$, then the solvent is evaporated under reduced pressure to yield 2,2'-[(butylimino)dimethanediyl]di(N-boc-8-quinoline amine) in the form of a pale yellow powder which is characterised by NMR-$^1$H then introduced into the subsequent reaction without additional purification. NMR-$^1$H (250 MHz, $CDCl_3$) δ, ppm: 9.02 (s large, 2H); 8.38 (d large, $^3$J (H, H)=7.5 Hz, 2H); 8.09 (d, $^3$J (H, H)=8.5 Hz, 2H); 7.72 (d, $^3$J (H, H)=8.5 Hz, 2H); 7.46 (dd, $^3$J (H, H)=8.0 and 7.5 Hz, 2H); 7.38 (dd, $^3$J (H, H)=8.0 Hz, $^4$J (H, H)=1.5 Hz, 2H); 3.99 (s, 4H); 2.62 (t, $^3$J (H, H)=7.0 Hz, 2H); 1.62 (m, 2H); 1.59 (s, 18H); 1.34 (m, 2H); 0.87 (t, $^3$J (H, H)=7.5 Hz, 3H).

2,2'-[(butylimino)dimethanediyl]di(8-quinoline amine) (Compound 22)

2,2'-[(butylimino)dimethanediyl]di(N-boc-8-quinoline amine) obtained in the previous stage is dissolved in 0.5 ml of $CH_2Cl_2$ and 0.5 ml of trifluoroacetic acid and stirred for 45 minutes at ambient temperature, then the solvents are evaporated under reduced pressure. The residue is dissolved in 5 ml of $CH_2Cl_2$ and washed with a saturated aqueous solution of $NaHCO_3$ (2×5 ml) before being dried over anhydrous $Na_2SO_4$, then the solvent is evaporated under reduced pressure. The product is purified by silica gel chromatography, eluted with a hexane/ethyl acetate mixture (8/2 to 1/1; v/v) to yield after evaporation of the solvent 22 in the form of an orange oil (20 mg; 0.05 mmol, yield=42% over 2 stages). NMR-$^1$H (250 MHz, $CDCl_3$) δ, ppm: 8.02 (d, $^3$J (H, H)=8.5 Hz, 2H); 7.65 (d, $^3$J (H, H)=8.5 Hz, 2H); 7.28 (dd, $^3$J (H, H)=8.5 and 7.5 Hz, 2H); 7.12 (dd, $^3$J (H, H)=8.5 Hz, $^4$J (H, H)=1.0 Hz, 2H); 6.90 (dd, $^3$J (H, H)=7.5 Hz, $^4$J (H, H)=1.0 Hz, 2H); 4.98 (s large, 4H); 3.97 (s, 4H); 2.60 (t, $^3$J (H, H)=7.0 Hz, 2H); 1.60 (tt, $^3$J (H, H)=7.5 and 7.0 Hz, 2H); 1.32 (qt, $^3$J (H, H)=8.0 and 7.5 Hz, 2H); 0.85 (t, $^3$J (H, H)=8.0 Hz, 3H). NMR-$^{13}$C (63 MHz, $CDCl_3$) δ, ppm: 143.7 (Cq); 137.4 (Cq); 136.2 (CH); 127.7 (Cq); 126.8 (CH); 126.7 (Cq); 121.3 (CH); 115.8 (CH); 110.0 (CH); 60.9 ($CH_2$); 54.3 ($CH_2$); 29.4 ($CH_2$); 20.5 ($CH_2$); 13.9 ($CH_3$). MS (CID, $NH_3$): m/z=386 ($MH^+$).

2-Chloro-8-nitroquinoline

Synthesis was carried out according to the protocol of: M. C. Kimber et al., Aust. J. Chem 2003, 56, 39-44. NMR data which are more specific than those previously published are added hereinafter. NMR $^1$H (250 MHz, $CDCl_3$) d, ppm: 8.21 (d, $^3$J (H, H)=8.5 Hz, 1H); 8.10 (dd, $^3$J (H, H)=7.5 Hz, $^4$J (H, H)=1.5 Hz, 1H); 8.05 (dd, $^3$J (H, H)=8.0 Hz, $^4$J (H, H)=1.5 Hz, 1H); 7.65 (m, 1H); 7.55 (d, $^3$J (H, H)=8.5 Hz, 1H). NMR-$^{13}$C (63 MHz, $CDCl_3$) δ, ppm: 153.5 (Cq); 147.1 (Cq); 138.9 (Cq); 138.8 (CH); 131.9 (CH); 127.6 (Cq); 125.8 (CH); 125.0 (CH); 124.5 (CH). MS (CID, $NH_3$): m/z=209 ($MH^+$), 226 ($MNH_4^+$), 243 ($MN_2H_7^+$). Analysis (%) for $C_9H_5N_2O_2Cl$: calculated C, 51.82; H, 2.42; N, 13.43. found C, 51.76; H, 2.37; N, 13.24. The molecule structure was confirmed by X-ray diffraction analysis on monocrystals obtained by crystallisation of the product in deuterated chloroform. The structure is presented in FIG. 5. The parameters for crystal analysis are as follows: orthorhombic crystal system; P c a 21; a=18.090 (4) Å, b=3.7781 (7) Å, c=12.581 (2) Å, α=90°, β=90°, γ=90°.

N-butyl-8-nitro-2-quinoline amine 2-chloro-8-nitroquinoline (0.20 g; 0.96 mmol) is suspended in 9.5 ml of 1-butylamine and the medium is heated under reflux (78° C.) for 15 hours. The yellow solution obtained is subsequently concentrated under vacuum. The crude reaction product is taken up in a minimum volume of $CH_3OH$ and poured over 3 ml of diethyl ether. After centrifugation, butyl ammonium chloride crystals are removed and the supernatant is concentrated under reduced pressure to yield N-butyl-8-nitro-2-quinoline amine in the form of a yellow oil (0.21 g; 0.86 mmol, yield=90%). NMR-$^1$H (250 MHz, $CDCl_3$) δ, ppm: 7.83 (dd, $^3$J (H, H)=7.5 Hz, $^4$J (H, H)=1.5 Hz, 1H); 7.77 (d, $^3$J (H, H)=9.0 Hz, 1H); 7.69 (dd, $^3$J (H, H)=8.0 Hz, $^4$J (H, H)=1.5 Hz, 1H); 7.14 (m, 1H); 6.67 (d, $^3$J (H, H)=9.0 Hz, 1H); 5.07 (s large, 1H); 3.47 (m, 2H); 1.60 (m, 2H); 1.39 (m, 2H); 0.93 (t, $^3$J (H, H)=7.5 Hz, 3H). NMR-$^{13}$C (63 MHz, $CDCl_3$) δ, ppm: 157.8 (Cq); 145.6 (Cq); 140.2 (Cq); 136.7 (CH); 131.5 (CH); 124.7 (CH); 124.1 (CH); 119.7 (CH); 113.3 (Cq); 41.3 ($CH_2$); 31.5 ($CH_2$); 20.2 ($CH_2$); 13.8 ($CH_3$). MS (CID, $NH_3$): m/z=246 ($MH^+$). Analysis (%) for $C_{13}H_{15}N_3O_2$: calculated C, 63.66; H, 6.16; N, 17.13. found C, 63.33; H, 6.21; N, 16.64.

N-butyl-2,2'-imino-bis(8-nitroquinoline) (Compound 23')

2-chloro-8-nitroquinoline (122 mg; 0.59 mmol) and NaOtBu (77.5 mg; 0.81 mmol) are added to a violet suspension of N-butyl-8-nitro-2-quinoline amine (0.17 g; 0.69 mmol), tris(dibenzylidene-acetone)-dipalladium(0) (13 mg; 0.014 mmol) and rac-2,2'-bis(diphenylphosphino)-1,1'-binaphthyl (17 mg; 0.027 mmol) in 5 ml of toluene under argon. The medium is heated under reflux for 3 hours, then 2-chloro-8-nitroquinoline (22 mg; 0.11 mmol) is again added. Heating is continued for 2 hours 30 minutes then 10 ml of a saturated ammonium chloride solution are added. The product is extracted with 3×30 ml of $CH_2Cl_2$ and the solvent is evaporated under reduced pressure. The product is purified by silica gel chromatography, eluted with $CH_2Cl_2$/hexane (80/20, v/v) to yield N-butyl-2,2'-imino-bis(8-nitroquinoline) in the form of a yellow powder (0.11 g; 0.26 mmol, yield=38%). NMR-$^1$H (250 MHz, CDCl$_3$) δ, ppm: 8.14 (d, $^3$J (H, H)=9.0 Hz, 2H); 7.99 (dd, $^3$J (H, H)=7.5 Hz, $^4$J (H, H)=1.5 Hz, 2H); 7.93 (dd, $^3$J (H, H)=8.0 Hz, $^4$J (H, H)=1.5 Hz, 2H); 7.73 (d, $^3$J (H, H)=9.0 Hz, 2H); 7.43 (m, 2H); 4.45 (t, $^3$J (H, H)=7.5 Hz, 2H); 1.83 (m, 2H); 1.47 (m, 2H); 0.98 (t, $^3$J (H, H)=7.5 Hz, 3H). NMR-$^{13}$C (63 MHz, CDCl$_3$) δ, ppm: 156.2 (Cq); 146.4 (Cq); 138.7 (Cq); 137.0 (CH); 131.5 (CH); 126.2 (Cq); 124.2 (CH); 122.8 (CH); 117.3 (CH); 48.9 (CH$_2$); 30.4 (CH$_2$); 20.3 (CH$_2$); 13.9 (CH$_3$). MS (CID, NH$_3$): m/z=418 (MH$^+$). Analysis (%) for $C_{22}H_{19}N_5O_4$: calculated C, 63.30; H, 4.59; N, 16.78. found C, 63.18; H, 4.49; N, 16.39. UV/vis [CH$_3$OH/20 mM Tris-HCl pH=7.4 containing 150 mM NaCl (1/1, v/v)]: λ nm (ε M$^{-1}$ cm$^{-1}$)=210 (91,400), 226 (53,500, shoulder), 270 (42, 100), 294 (26,700, shoulder), 383 (28,400).

N-butyl-2,2'-imino-bis(8-quinoline amine) (Compound 23)

10% by weight palladium on carbon (50 mg) is added to a solution of N-butyl-2,2'-imino-bis(8-nitroquinoline) (230 mg; 0.55 mmol) in 35 ml of ethyl acetate. The mixture is placed under a dihydrogen atmosphere (1 bar) and stirred for 4 hours at ambient temperature. After the palladium has been removed by filtration over cellite, the organic phase is concentrated under reduced pressure. The crude reaction product is taken up in the minimum amount of $CH_2Cl_2$ and precipitated with four volumes of hexane. After filtration, the supernatant is concentrated under reduced pressure and the product is dried under vacuum to yield 23 in the form of a brown powder (197 mg; 0.55 mmol, quantitative yield). NMR-$^1$H (250 MHz, CDCl$_3$) δ, ppm: 7.90 (d, $^3$J (H, H)=9.0 Hz, 2H); 7.32 (d, $^3$J (H, H)=9.0 Hz, 2H); 7.20 (m, 2H); 7.10 (dd, $^3$J (H, H)=8.0 Hz, $^4$J (H, H)=1.0 Hz, 2H); 6.93 (dd, $^3$J (H, H)=7.5 Hz, $^4$J (H, H)=1.0 Hz, 2H); 4.60 (s, 4H); 4.48 (t, $^3$J (H, H)=7.5 Hz, 2H); 1.88 (m, 2H); 1.47 (m, 2H); 0.97 (t, $^3$J (H, H)=7.5 Hz, 3H). NMR-$^{13}$C (63 MHz, CDCl$_3$) δ, ppm: 154.1 (Cq); 142.1 (Cq); 137.2 (CH); 137.0 (Cq); 125.3 (Cq); 125.0 (CH); 116.3 (CH); 116.1 (CH); 111.3 (CH); 48.9 (CH$_2$); 30.6 (CH$_2$); 20.7 (CH$_2$); 14.1 (CH$_3$). MS (CID, NH$_3$): m/z=358 (MH$^+$). UV/vis [CH$_3$OH/20 mM Tris-HCl pH=7.4 containing 150 mM NaCl (1/1, v/v)]: λ nm (ε M$^{-1}$ cm$^{-1}$)=211 (53,400, shoulder), 302 (40,300), 367 (20,000), 382 (14,600, shoulder).

N-8-quinolinyl-8-quinoline carboxamide (Compound 24)

(Benzotriazol-1-yloxy)tris(dimethylamino)phosphonium hexafluorophosphate (192 mg; 0.43 mmol), 1-hydroxybenzotriazole monohydrate (79 mg; 0.59 mmol) and triethylamine (0.200 ml; 1.44 mmol) are added to a solution of quinoline-8-carboxylic acid (50 mg; 0.29 mmol) dissolved in 5 ml of dry $CH_2Cl_2$. After stirring for 30 minutes at ambient temperature, 8-aminoquinoline (84 mg; 0.58 mmol) is added and the mixture is stirred for 4 hours 30 minutes at ambient temperature. Water (10 ml) is added and the product is extracted with $CH_2Cl_2$ (3×10 ml). The volume is reduced and the product is purified by silica gel chromatography, eluted with $CH_2Cl_2$/CH$_3$OH (0 to 2%, v/v) then the solvent is evaporated under reduced pressure and the fractions containing a high proportion of products are repurified by silica gel chromatography, eluted with $CH_2Cl_2$/CH$_3$OH (99.5/0.5; v/v). 24 is obtained after evaporation of the solvent in the form of a white powder (83 mg; 0.28 mmol, yield=96%). NMR-$^1$H (250 MHz, CDCl$_3$) δ, ppm: 15.13 (s, 1H); 9.25 (dd, $^3$J (H, H)=4.0 Hz, $^4$J (H, H)=2.0 Hz, 1H); 9.19 (dd, $^3$J (H, H)=7.5 Hz, $^4$J (H, H)=1.5 Hz, 1H); 9.00 (m, 2H); 8.32 (dd, $^3$J (H, H)=8.0 Hz, $^4$J (H, H)=2.0 Hz, 1H); 8.19 (dd, $^3$J (H, H)=8.0 Hz, $^4$J (H, H)=1.5 Hz, 1H); 8.01 (dd, $^3$J (H, H)=8.0 Hz, $^4$J (H, H)=1.5 Hz, 1H); 7.74 (dd, $^3$J (H, H)=7.5 and 8.0 Hz, 1H); 7.60 (m, 3H); 7.48 (dd, $^3$J (H, H)=4.5 and 8.0 Hz, 1H). NMR-$^{13}$C (63 MHz, CDCl$_3$) δ, ppm: 164.28; 149.48; 148.57; 145.60; 140.12; 137.59; 136.65; 136.18; 134.02; 132.10; 129.85; 128.41; 128.28; 127.50; 126.63; 121.75; 121.34; 121.12; 118.18. MS (CID, NH$_3$): m/z=300 (MH$^+$). UV/vis [DMSO/20 mM Tris-HCl pH=7.4 containing 150 mM NaCl (8/2, v/v)]: λ nm (ε M$^{-1}$ cm$^{-1}$)=261 (13,300, shoulder), 274 (14,800), 294 (12,200).

N-8-quinolinyl-8-quinolinesulfonamide (Compound 25)

The product has already been described in: V. M. Dziomko et al., *Azotsoderzhashchie Geterotsikly* 1967, 281-284; but by a different method of synthesis. Several grains of activated 4 Å molecular sieve are added to a solution under argon of 8-aminoquinoline (200 mg; 1.39 mmol) and triethylamine (0.30 ml; 2.15 mmol) in 10 ml of CHCl$_3$ and the mixture is stirred slowly for 1 hour. 8-quinolinesulfonyl chloride (350 mg; 1.54 mmol) is added and the mixture is heated to 65° C. for 15 hours. After cooling, 50 ml of CHCl$_3$ are added and the mixture is washed in water (2×50 ml) then dried over anhydrous Na$_2$SO$_4$ and the solvent is evaporated under reduced pressure. The solid is washed with 5 ml of $CH_2Cl_2$ to yield after drying 25 in the form of a beige powder (108 mg; 0.32 mmol, yield=23%). NMR-$^1$H (250 MHz, DMSO-d$_6$) δ, ppm: 10.44 (s, 1H); 9.11 (dd, $^3$J (H, H)=4.5 Hz, $^4$J (H, H)=1.5 Hz, 1H); 8.83 (dd, $^3$J (H, H)=4.0 Hz, $^4$J (H, H)=1.5 Hz, 1H); 8.47 (dd, $^3$J (H, H)=7.5 Hz, $^4$J (H, H)=1.5 Hz, 1H); 8.40 (dd, $^3$J (H, H)=8.5 Hz, $^4$J (H, H)=1.5 Hz, 1H); 8.22 (dd, $^3$J (H, H)=8.0 Hz, $^4$J (H, H)=1.5 Hz, 1H); 8.20 (dd, $^3$J (H, H)=8.0 Hz, $^4$J (H, H)=1.5 Hz, 1H); 7.80 (dd, $^3$J (H, H)=7.5 Hz, $^4$J (H, H)=1.5 Hz, 1H); 7.70 (dd, $^3$J (H, H)=8.0 and 7.5 Hz, 1H); 7.62 (dd, $^3$J (H, H)=8.5 and 4.5 Hz, 1H); 7.51 ((dd, $^3$J (H, H)=8.5 and 4.0 Hz, 1H); 7.50 (dd, $^3$J (H, H)=8.5 Hz, $^4$J (H, H)=1.0 Hz, 1H); 7.42 (dd, $^3$J (H, H)=8.0 and 7.5 Hz, 1H). NMR-$^{13}$C (63 MHz, DMSO-d$_6$) δ, ppm: 151.5 (CH); 148.9 (CH); 142.1 (Cq); 137.6 (Cq); 136.9 (CH); 136.3 (CH); 134.4 (CH); 134.2 (Cq); 133.7 (Cq); 131.7 (CH); 128.2 (Cq); 127.8 (Cq); 126.6 (CH); 125.5 (CH); 122.6 (CH); 122.3 (CH); 122.1 (CH); 113.8 (CH). MS (CID, NH$_3$): m/z=336 (MH$^+$). Analysis (%) for $C_{18}H_{13}N_3O_2S \cdot 0.2H_2O$: calculated C, 63.78; H, 3.98; N, 12.40. found C, 63.53; H, 3.70; N, 12.23.

Results:
Capacity of Compounds to Chelate Metals:
Determination of the Metal/Ligand Stoichiometry:

UV-visible absorption spectra and UV-visible spectrophotometric titrations were carried out in the presence of a 20 mM Tris-HCl buffer pH=7.4 containing 150 mM NaCl since this is the solvent used for the Aβ$_{1-42}$ resolubilisation experiments. An organic solvent (CH$_3$OH, dioxane or DMSO) was added in order to achieve good solubility of the ligands and metal complexes in the concentrations used in these experiments. Exact proportions of the organic solvent/buffer mixture are specified for each UV-visible characterisation of the different ligands or metal complexes.

Aliquot portions of concentrated CuCl$_2$ or ZnCl$_2$ solutions (M) are added to a 15 μM ligand solution so as to induce only negligible variations in volume. After each addition, changes in absorption spectra are observed immediately and are consistent between two additions, which corresponds to a rapid complexing process. The exact absorption values relating to each ligand and the copper(II) or zinc(II) complexes thereof are detailed hereinafter in the Experimental part (in the Synthesis part for ligands and hereinafter for the metal complexes).

The stoichiometry of the different ligands (L) for Cu(II) or ZN(II) have therefore been determined spectrophotometrically by metal ion titration. A typical example, obtained in the case of $CuCl_2$ titration by ligand 3 is presented in FIG. 6. In this example, for an M/L ratio increasing from 0 to 1, $\pi \rightarrow \pi^*$ transition, centred at 251 nm for the free ligand, is shifted to a lower energy with a concomitant appearance of an absorption band in the visible region of the spectrum ($\lambda_{max}$ to 383 nm), which is probably the result of an MLCT transition. For greater M/L ratios, no additional change in the UV-visible absorption spectra is observed. These results correspond to a capacity of the ligand 3 to form one type of Cu(II) complex with an M/L (1/1) stoichiometry.

Similar results were obtained with other ligands in the presence of Cu(II) or Zn(II) and are shown in Table 3.

Preparation of Metal Complexes for Mass Spectrometry Characterisation:

The ligands, dissolved in methanol or dioxane, were metallised in the presence of one metal ion equivalent for 1 hour at ambient temperature then the solvent was evaporated. $Cu(AcO)_2$ or $Zn(AcO)_2$ were used for the ligands 1 to 11 and $CuCl_2$ or $ZnCl_2$ for the other ligands. Control analyses, carried out after redissolution of the complexes in the appropriate buffer/organic solvent mixture, showed that UV-visible spectra of the different complexes thus obtained are the same as those obtained in the titration experiments for an identical ligand and metal ion stoichiometry.

Cu(II)-1: MS (CID, $NH_3$) m/z: 364 (LCu(II)—1H), 381 (LCu(II)$NH_4$—2H). UV/vis [dioxane/20 mM Tris-HCl pH=7.4 containing 150 mM NaCl (1/1, v/v)]: λ nm ($\epsilon$ $M^{-1}$ $cm^{-1}$)=256 (41,900), 272 (32,200, shoulder), 304 (8,800), 338 (5,100), 376 (3,100).

Cu(II)-2: MS (CID, $NH_3$) m/z: 434 (LCu(II)—1H), 451 (LCu(II)$NH_4$—2H). Analysis (%) for $C_{19}H_{10}N_2O_2Cl_2Cu$: calculated C, 52.73; H, 2.33; N, 6.47. found C, 52.52; H, 1.64; N, 6.48. UV/vis [dioxane/20 mM Tris-HCl pH=7.4 containing 150 mM NaCl (1/1, v/v)]: λ nm ($\epsilon$ $M^{-1}$ $cm^{-1}$)=256 (38, 300), 278 (35,900), 310 (10,300), 342 (7,300), 398 (4,000).

Cu(II)-3: MS (CID, $NH_3$) m/z: 3924Cu(II)—1H), 409 (LCu(II)$NH_4$—2H). Analysis (%) for $C_{21}H_{16}N_2O_2Cu.0.3 C_2H_4O_2$: calculated C, 63.33; H, 4.16; N, 6.84. found C, 63.30; H, 3.50; N, 6.82. UV/vis [$CH_3OH$/20 mM Tris-HCl pH=7.4 containing 150 mM NaCl (1/1, v/v)]: λ nm ($\epsilon$ $M^{-1}$ $cm^{-1}$)=202 (70,800), 254 (58,900), 268 (42,400, shoulder), 383 (4,300).

Cu(II)-4: MS (CID, $NH_3$) m/z: 462 (LCu(II)—1H), 479 (LCu(II)$NH_4$—2H). Analysis (%) for $C_{21}H_{14}N_2O_2Cl_2Cu$: calculated C, 54.74; H, 3.06; N, 6.08. found C, 54.50; H, 2.84; N, 5.92. UV/vis [dioxane/20 mM Tris-HCl pH=7.4 containing 150 mM NaCl (1/1, v/v)]: λ nm ($\epsilon$ $M^{-1}$ $cm^{-1}$)=261 (59, 500), 274 (46,900, shoulder), 347 (4,700), 409 (5,800).

Cu(II)-5: MS (CID, $NH_3$) m/z: 400 (CID, $NH_3$) m/z: UV/vis [$CH_3OH$/20 mM Tris-HCl pH=7.4 containing 150 mM NaCl (1/1, v/v)]: λ nm ($\epsilon$ $M^{-1}$ $cm^{-1}$)=205 (64,000), 255 (47,600), 276 (34,400), 415 (2,900).

Cu(II)-6: MS (CID, $NH_3$) m/z: 378 (LCu(II)—1H), 395 (LCu(II)$NH_4$—2H). UV/vis [$CH_3OH$/20 mM Tris-HCl pH=7.4 containing 150 mM NaCl (1/1, v/v)]: λ nm ($\epsilon$ $M^{-1}$ $cm^{-1}$)=245 (41,100), 306 (27,900), 348 (12,100, shoulder), 485 (2,500).

Cu(II)-7: MS (CID, $NH_3$) m/z: 378 (LCu(II)—1H)395 (LCu(II)$NH_4$—2H). Analysis (%) for $C_{20}H_{14}N_2O_2Cu.0.3H_2O$: calculated C, 62.67; H, 3.84; N, 7.31. found C, 62.68; H, 2.91; N, 7.21. UV/vis [$CH_3OH$/20 mM Tris-HCl pH=7.4 containing 150 mM NaCl (1/1, v/v)]: λ nm ($\epsilon$ $M^{-1}$ $cm^{-1}$)=202 (57,700), 259 (68,000), 268 (46,200, shoulder), 392 (4,900).

Cu(II)-8: MS (CID, $NH_3$) m/z: 448 (LCu(II)—1H), 465 (LCu(II)$NH_4$—2H). Analysis (%) for $C_{20}H_{12}N_2O_2Cl_2Cu.0.3H_2O$: calculated C, 53.12; H, 2.81; N, 6.20. found C, 53.09; H, 2.37; N, 6.08. UV/vis [dioxane/20 mM Tris-HCl pH=7.4 containing 150 mM NaCl (1/1, v/v)]: λ nm ($\epsilon$ $M^{-1}$ $cm^{-1}$)=264 (64,700), 276 (46,700), 413 (5,300).

Cu(II)-9: MS (CID, $NH_3$) m/z: 700 (LCu(II)—1H), 717 (LCu(II)$NH_4$—2H). Anal. for $C_{20}H_{10}N_2O_2Cl_2I_2Cu.2_2H_4O_2$): calculated C, 35.30; H, 1.97; N, 3.43. found C, 35.46; H, 1.20; N, 3.83. UV/vis [DMSO/20 mM Tris-HCl pH=7.4 containing 150 mM NaCl (8/2, v/v)]: λ nm ($\epsilon$ $M^{-1}$ $cm^{-1}$)=(56,000), 340 (55,000), 392 (6,200), 420 (5,000).

Cu(II)-10: MS (CID, $NH_3$) m/z: 406 (LCu(II)—1H), 423 (LCu(II)$NH_4$—2H). UV/vis [$CH_3OH$/20 mM Tris-HCl pH=7.4 containing 150 mM NaCl (1/1, v/v)]: λ nm ($\epsilon$ $M^{-1}$ $cm^{-1}$)=204 (56,000), 260 (71,800), 374 (4,800).

Cu(II)-12-Cl: MS (CID, $NH_3$) m/z: 369 (LCu(II)Cl). UV/vis [DMSO/20 mM Tris-HCl pH=7.4 containing 150 mM NaCl (8/2, v/v)]: λ nm ($\epsilon$ $M^{-1}$ $cm^{-1}$)=287 (40,700), 368 (3,300), 486 (14,100).

Cu(II)-13: MS (electrospray, >0) m/z: 390 (LCu(II)—1H). UV/vis [$CH_3OH$/20 mM Tris-HCl pH=7.4 containing 150 mM NaCl (1/1, v/v)]: λ nm ($\epsilon$ $M^{-1}$ $cm^{-1}$)=230 (55,700); 303 (11,800), 315 (10,400), 360 (1,100, shoulder).

Cu(II)-14: MS (electrospray, >0) m/z: 405 [LCu(II)].

Cu(II)-16: MS (electrospray, >0) m/z: 423 (LCu(II)—2H). UV/vis [$CH_3OH$/20 mM Tris-HCl pH=7.4 containing 150 mM NaCl (1/1, v/v)]: λ nm ($\epsilon$ $M^{-1}$ $cm^{-1}$)=254 (34,400), 278 (35,900), 316 (9,700, shoulder), 380 (3,100).

Cu(II)-17: MS (electrospray, >0) m/z: 438 (LCu(II)—1H). UV/vis [$CH_3OH$/20 mM Tris-HCl pH=7.4 containing 150 mM NaCl (1/1, v/v)]: λ nm ($\epsilon$ $M^{-1}$ $cm^{-1}$)=212 (50,300), 263 (65,300), 275 (47,300, shoulder), 319 (4,500), 421 (5,900)

Cu(II)-23: MS (electrospray, >0) m/z: 419 (LCu(II)—1H). UV/vis [$CH_3OH$/20 mM Tris-HCl pH=7.4 containing 150 mM NaCl (1/1, v/v)]: λ nm ($\epsilon$ $M^{-1}$ $cm^{-1}$)=211 (65,400); 235 (33,800, shoulder), 275 (37,000), 302 (5,900, shoulder), 329 (17,900), 352 (19,000), 366 (20,900).

Cu(II)-24: MS (electrospray, >0) m/z: 361 (LCu(II)—1H).

Zn(II)-1: MS (CID, $NH_3$) m/z: 365 (LZn(II)—1H), 382 (LZn(II)$NH_4$—2H).

Zn(II)-2: MS (CID, $NH_3$) m/z: 433 (LZn(II)—1H(II) 454 (LZn (II)$NH_4$—2H).

Zn(II)-3: MS (CID, $NH_3$) m/z: 393 (LZn(II)—1H), 410 (LZn(II)$NH_4$—2H).
UV/vis [$CH_3OH$/20 mM Tris-HCl pH=7.4 containing 150 mM NaCl (1/1, v/v)]: λ nm ($\epsilon$ $M^{-1}$ $cm^{-1}$)=202 (78,700), 258 (74,100), 268 (46,700), 378 (4,600).

Zn(II)-4: MS (CID, $NH_3$) m/z: 463 (LZn(II)—1H), 482 (LZn(II)$NH_4$—2H). UV/vis [dioxane/20 mM Tris-HCl pH=7.4 containing 150 mM NaCl (1/1, v/v)]: λ nm ($\epsilon$ $M^{-1}$ $cm^{-1}$)=265 (69,200), 275 (45,700), 346 (5,800), 405 (6,100).

Zn(II)-5: MS (CID, $NH_3$) m/z: 401 (LZn(II)—1H). UV/vis [$CH_3OH$/20 mM Tris-HCl pH=7.4 containing 150 mM NaCl (1/1, v/v)]: λ nm ($\epsilon$ $M^{-1}$ $cm^{-1}$)=205 (43,300), 258 (50,500), 274 (30,900), 404 (3,000).

Zn(II)-6: MS (CID, $NH_3$) m/z: 379 (LZn(II)—1H), 396 (LZn(II)$NH_4$—2H). UV/vis [$CH_3OH$/20 mM Tris-HCl pH=7.4 containing 150 mM NaCl (1/1, v/v)]: λ nm ($\epsilon$ $M^{-1}$ $cm^{-1}$)=238 (31,100), 298 (26,200), 346 (10,500, shoulder), 473 (3,000).

Zn(II)-7: MS (CID, NH$_3$) m/z: 379 (LZn(II)—1H), 396 (LZn(II)NH$_4$—2H). UV/vis [CH$_3$OH/20 mM Tris-HCl pH=7.4 containing 150 mM NaCl (1/1, v/v)]: λ nm (ε M$^{-1}$ cm$^{-1}$)=202 (55,500), 258 (63,600), 268 (43,400, shoulder), 374 (4,000).

Zn(II)-8: MS (CID, NH$_3$) m/z: 449 (LZn(II)—1H), 466 (LZn(II)NH$_4$—2H). UV/vis [dioxane/20 mM Tris-HCl pH=7.4 containing 150 mM NaCl (1/1, v/v)]: λ nm (ε M$^{-1}$ cm$^{-1}$)=264 (57,800), 272 (43,600, shoulder), 390 (5,400).

Zn(II)-9: MS (ES-MS, <0) m/z: 735 (LZn(II)HCl). UV/vis [DMSO/20 mM Tris-HCl pH=7.4 by silica containing 150 mM NaCl (8/2, v/v)]: λ nm (ε M$^{-1}$ cm$^{-1}$)=276 (54,200), 340 (5,800), 352 (7,700), 397 (5,100).

Zn(II)-10: (CID, NH$_3$) m/z: 407 (LZn(II)—1H), 424 (LZn(II)NH$_4$—2H). UV/vis [CH$_3$OH/20 mM Tris-HCl pH=7.4; by silica containing 150 mM NaCl (1/1, v/v)]: λ nm (ε M$^{-1}$ cm$^{-1}$)=202 (63,600), 260 (65,600), 368 (4,400).

Zn(II)-12-Cl: MS (CID, NH$_3$) m/z: 370 (LZn(II)Cl). UV/vis (CH$_3$OH): λ nm (ε M$^{-1}$ cm$^{-1}$)=288 (31,800), 299 (27,900), 369 (3,400), 490 (13,200).

Zn(II)-13: UV/vis [CH$_3$OH/20 mM Tris-HCl pH=7.4 by silica containing 150 mM NaCl (1/1, v/v)]: λ nm (ε M$^{-1}$ cm$^{-1}$)=232 (55,400); 300 (9,600), 314 (9,200), 364 (700, shoulder).

Zn(II)-14: UV/vis [CH$_3$OH/20 mM Tris-HCl pH=7.4 containing 150 mM NaCl (1/1, v/v)]: λ nm (ε M$^{-1}$ cm$^{-1}$)=236 (43,900), 304 (8,700), 316 (8,000).

Zn(II)-16: MS (electrospray, >0) m/z: 425 (LZn(II)—1H). UV/vis [CH$_3$OH/20 mM Tris-HCl pH=7.4 containing 150 mM NaCl (1/1, v/v)]: λ nm (ε M$^{-1}$ cm$^{-1}$)=262 (44,700), 276 (22,300, shoulder), 308 (5,900), 390 (2,000).

Zn(II)-17: MS (electrospray, >0) m/z: 439 (LZn(II)—1H). UV/vis [CH$_3$OH/20 mM Tris-HCl pH=7.4 containing 150 mM NaCl (1/1, v/v)]: λ nm (ε M$^{-1}$ cm$^{-1}$)=202 (66,900); 264 (92,500), 276 (47,100, shoulder), 318 (5,500), 398 (6,700).

Zn(II)-18: MS (electrospray, >0) m/z: 394 (LZn(II)—1H). UV/vis [DMSO/20 mM Tris-HCl pH=7.4 containing 150 mM NaCl (8/2, v/v)]: λ nm (ε M$^{-1}$ cm$^{-1}$)=273 (27,400); 309 (23,800), 332 (22,000); 4307 (3,800).

Zn(II)-23: UV/vis [CH$_3$OH/20 mM Tris-HCl pH=7.4 containing 150 mM NaCl (1/1, v/v)]: λ nm (ε M$^{-1}$ cm$^{-1}$)=213 (47,000); 234 (24,800), 274 (25,600), 303 (10,900, shoulder), 330 (11,600), 348 (12,300), 363 (13,100).

Estimate of Affinity Constants of Ligands for Metal Ions:

Solutions of ligands to be investigated $L_s$, of competing chelator $L_c$ and of metal ion M in the ratio 1/1/1 are analysed by UV-visible spectrophotometry at 20° C. The concentration of each component is 15 µM. UV-visible absorption spectra of $L_s$, $ML_s$, $L_c$ or $ML_c$ species and spectrophotometric analyses of competitors are carried out in the presence of a 20 mM Tris-HC buffer containing 150 mM NaCl (pH=7.4) since it is the solvent used in the Aβ$_{1-42}$ resolubilisation experiments described hereinafter. An organic solvent (CH$_3$OH, dioxane or DMSO) was added in order to achieve good solubility of all the ligands and metal complexes in the concentrations used in these experiments. Monitoring has shown that all the ligands and metal complexes examined yield results corresponding to the Beer-Lambert Law in the experimental conditions used.

The ($L_c$) metal ion chelators used in the competition experiments were selected from "The National Institute of Standards and Technology Standard Reference Data base 46" NIST (Critically Selected Stability Constants of Metal Complexes Database, version 4.0, U.S. Department of Commerce) and L. G. Sillen, A. E. Martell *Stability Constants of Metal-Ion complexes*, The Chemical Society London Publication, 1971.

$L_c$ competing chelators were selected to provide a range of stability constants for the metal ion M presenting intervals of approximately one or two log units, as well as to make it possible for each competition experiment to quantify one of the $L_s$, $ML_s$, $L_c$ or $ML_c$ species with a UV-vis spectrum wavelength without contaminating the three other species (FIG. 7). The stability constants K=[ML]/([M][L]) selected for the competing chelators are given for 25° C., an ionic strength of 0.1-0.2v and a metal ion to chelator molar ratio of 1/1 in Tables 1 and 2. If more than one metal complex can be formed between the metal ion and the chelator, the competing chelator was only selected if log K of the metal complex thereof having a metal ion to chelator ratio of 1/1 is greater than those of all the other possible complexes.

Log K of a chelator for a metal ion varies with the pH of the solution as determined by the following equations (C. S. Atwood et al., *J. Neurochem.* 2000, 75, 1219-1233; A. Ringblom, *Complexation in Analytical Chemistry*, 1963, Interscience, New York; G. Schwarznbach et al., *Complexometric Titrations*, 1969, Meuthuen, N.Y.):

$$\log K_{app} = \log K - \log \alpha \quad \text{(Eq. 1)}$$

where:

$$\alpha = [H^+]^n/(K_{a1} \times K_{a2} \times K_{a3} \times \ldots \times K_{an}) + [H^+]^{n-1}/(K_{a1} \times K_{a2} \times K_{a3} \times \ldots \times K_{an-1}) + \ldots + [H^+]/K_{a1} + 1 \quad \text{(Eq. 2)}$$

$K_a = 10^x$, where x=−pK$_a$ of the chelator (K$_a$ values are written in decreasing order of the pK$_a$ values), and n=no. of the pK$_a$ value. The log K$_{app}$ for the competing chelators used at pH=7.4 are presented in Tables 1 and 2.

If $L_S$, $L_C$ and M are used in a ratio of 1/1/1, and $L_S$ forms a complex MLs with the metal ion and $L_c$ forms a complex $ML_c$ with the metal ion $$L_s + M \overset{K_s}{\rightleftarrows} ML_s \quad K_s = \frac{[ML_s]}{[L_s][M]} \quad \text{(Eq. 3)}$$

$$L_c + M \overset{K_c}{\rightleftarrows} ML_c \quad K_c = \frac{[ML_c]}{[L_c][M]} \quad \text{(Eq. 4)}$$

$K_c$ is the value of $K_{app}$ for the competing chelator $L_C$, determined with equations 1 and 2.

It can be deduced therefrom that at equilibrium:

$$\frac{K_s}{K_c} = \frac{[ML_s][L_c]}{[ML_c][L_s]} \quad \text{(Eq. 5)}$$

and $$K_s = K_c \frac{[ML_s][L_c]}{[ML_c][L_s]} \quad \text{(Eq. 6)}$$

The initial concentration C is the same for $L_s$, $L_c$ and M. If the complexes $ML_s$ and $ML_c$ are observed at the same time on the UV-vis spectra for log K$_c$>6, all the metal ion can be considered complexed in the forms of $ML_s$ or $ML_c$ and at equilibrium:

$$[ML_s]+[ML_c]=C=[ML_s]+[L_s]=[ML_c]+[L_c]$$

As the concentration [ML$_s$]=x % of C is measured on the UV-visible spectra, the concentrations [L$_s$]=(1−x) % of C, $[ML_c]=(1-x)$ % of C and $[L_c]=x$ % of C can be deduced therefrom and:

$$K_s = K_c \frac{x^2}{(x-1)^2} \quad \text{(Eq. 7)}$$

Some experiments were also carried out, in the same solvents, with $L_s$ and M in a ratio of 1/1 (15 µM of each) but with different $L_C$ stoichiometries. For an initial concentration $C=L_s=M$, the concentration of the competing ligand $[L_C]=y$ % of C which, at equilibrium, makes it possible to obtain the concentration ratio $[ML_s]/[L_s]=1$ and therefore for which the concentrations $[ML_s]=[L_s]=50\%$ of C is deduced from graphs such as those in FIG. 8. In these conditions, $[ML_s]=[ML_c]$; $[ML_c]+[L_c]=Y$, $y \geq 50$ and:

$$K_s = K_c \frac{y-50}{50} \quad \text{(Eq. 8)}$$

When $\log K_s \leq 6$, these equations are not used since the percentages of metal ion which is free in the solution or chelated by the solvent or the buffer are not negligible.

In the solvent being investigated, therefore, in the case of 12 in the presence of Zn(II), only the number of ZnCl$_2$ equivalent has been determined, for 15 µM of ligand to be entirely in the form of Zn(II) complex in the solvent being investigated, the ligand being in competition with the tris buffer and the DMSO for the complexation of the metal ion. By comparison with other chelators in the same conditions: 2,2'-bipyridine ($\log K_{app} \approx 5$; 250 eq ZnCl$_2$)<12 (100 eq ZnCl$_2$)<1,10-phenanthroline ($\log K_{app} = 6.3$; 50 eq ZnCl$_2$). Hence an estimation of $\log K_s \approx 6$.

In the same way, in the buffer Tris/CH$_3$OH (1/1, v/v), the number of Zn(II) equivalent is between 100 and 200 eq for 13, between 500 and 1000 eq for 14, between 7.5 and 10 eq for 18, and between 100 and 200 eq for 23.

Tables 2 and 3 summarise the values observed during competitions and Table 3 gives the values of affinity constants which have been deduced therefrom.

Table 4 shows that there is little change in $\log K_s$ depending on the composition of the different media investigated.

TABLE 2

Competition reaction between the ligands ($L_s$), ZnCl$_2$ (M) and a competing ligand ($L_c$) in a ratio of 1/1/1 at 15 µM. For each ligand $L_s$, the solvents are those described in Table 3. The percentage of ZnL$_s$ species at equilibrium is given. The values in parentheses correspond to the number of $L_c$ equivalents making it possible to form 50% of ZnL$_s$ from a mixture of $L_s$ (15 µM, 1 equivalent) and ZnCl$_2$ (1/1, mol/mol). $K_1$ is the stability constant for the ML$_c$ species. $K_2$ is the stability constant for the M(L$_c$)$_2$ species.

| | Trien | NTA | EGTA | EDTA | DTPA |
|---|---|---|---|---|---|
| log K$_1$ | 11.9 | 10, 5 | 12.6 | 16.5 | 18.2 |
| log K$_1$ app | 7.8 | 8.0 | 9.4 | 13.7 | 13.9 |
| log K$_2$ | | 3.8 | | | |
| 3 | 100 | 100 | 100 | 30 (0.7 eq) | 20 |
| 4 | — | — | — | 20 | — |
| 5 | — | — | — | 55 | — |
| 6 | — | — | — | 75 | — |
| 7 | — | — | — | 55 | — |
| 8 | — | — | — | 30 | — |
| 9 | 100 | 100 | — | 65 | — |
| 10 | — | — | — | 45 | — |
| 17 | — | — | — | 35 | — |

TABLE 3

Species formed during titration reactions with CuCl$_2$ or ZnCl$_2$ and affinity constants of the different ligands for Cu(II) or Zn(II) ions at pH = 7.4.

| Ligand | Complex observed by titration with Cu$^{II}$ (observed L/Cu(II) stoichiometry) | log KCu$^{II}$ | Complex observed by titration with Zn$^{II}$ (observed L/Zn(II) stoichiometry) | Log KZn$^{II}$ | Solvent |
|---|---|---|---|---|---|
| 3 | LCu$^{II}$ (1/1) | 15.9 ± 1$^a$ | LZn$^{II}$ (1/1) | 13.3 ± 1$^a$ | Buffer/CH$_3$OH (1/1) |
| 4 | Cu$^{II}$ (1/1) | 15.4 ± 1$^a$ | LZn$^{II}$ (1/1) | 12.5 ± 1$^b$ | Buffer/dioxane$^c$ |
| 5 | LCu$^{II}$ (1/1) | 15.7 ± 1$^b$ | LZn$^{II}$ (1/1) | 13.9 ± 1$^b$ | Buffer/CH$_3$OH (1/1) |
| 6 | LCu$^{II}$ (1/1) | 16.6 ± 1$^b$ | LZn$^{II}$ (1/1) | 14.4 ± 1$^b$ | Buffer/CH$_3$OH (1/1) |
| 7 | LCu$^{II}$ (1/1) | 16.0 ± 1$^a$ | LZn$^{II}$ (1/1) | 13.9 ± 1$^b$ | Buffer/CH$_3$OH (1/1) |

TABLE 1

Competition reaction between the ligands ($L_s$), CuCl$_2$ (M) and a competing ligand ($L_c$) in a ratio of 1/1/1 at 15 15 µM. For each ligand $L_s$, the solvents used are those described in Table 3. The percentage of the CuL$_s$ species at equilibrium is given. The values in parentheses correspond to the number of $L_c$ equivalents, making it possible to form 50% of CuL$_s$ from a mixture of $L_s$ (15 µM, 1 equivalent) and CuCl$_2$ (1/1, mol/mol). $K_1$ is the stability constant for the ML$_c$ species. $K_2$ is the stability constant for the M(L$_c$)$_2$ species.

| | EDA | biPy | HIDA | Dien | EDDA | EDTA | Trien | CTDA | Tetren |
|---|---|---|---|---|---|---|---|---|---|
| log K$_1$ | 10.5 | 8.1 | 11.8 | 15.9 | 16.2 | 18.8 | 20.1 | 22.0 | 22.8 |
| log K$_1$ app | 7.8 | 8.1 | 10.5 | 11.8 | 13.9 | 15.9 | 16.0 | 17.1 | 17.9 |
| log K$_2$ | 9.1 | 5.5 | 4.0 | 5.0 | | | | | |
| 3 | 100 | 100 | 100 | — | 100 | 50 (1 eq) | 30 | 15 | 0 |
| 4 | — | — | 100 | — | 90 | 40 (0.65 eq) | — | — | — |
| 5 | — | — | — | — | — | 45 | — | — | — |
| 6 | — | — | — | — | — | 75 | — | — | — |
| 7 | — | — | — | — | — | 55 (1.1 eq) | — | — | — |
| 8 | — | — | — | — | — | 40 (0.65 eq) | — | — | — |
| 9 | — | — | — | 100 | — | 60 | 45 (0.75 eq) | — | 0 |
| 10 | — | — | — | — | — | 45 | — | — | — |
| 12 | — | — | — | — | — | 55 | — | — | — |
| 13 | — | — | — | — | 65 | 25 | — | — | — |
| 17 | — | — | — | — | — | 55 | — | — | — |
| 23 | — | — | — | — | — | 30 | — | — | — |

TABLE 3-continued

Species formed during titration reactions with CuCl$_2$ or ZnCl$_2$ and affinity constants of the different ligands for Cu(II) or Zn(II) ions at pH = 7.4.

| Ligand | Complex observed by titration with Cu$^{II}$ (observed L/Cu(II) stoichiometry) | log KCu$^{II}$ | Complex observed by titration with Zn$^{II}$ (observed L/Zn(II) stoichiometry) | Log KZn$^{II}$ | Solvent |
|---|---|---|---|---|---|
| 8 | LCu$^{II}$ (1/1) | 15.4 ± 1[a] | LZn$^{II}$ (1/1) | 13.0 ± 1[b] | Buffer/dioxane[c] |
| 9 | LCu$^{II}$ (1/1) | 15.7 ± 1[a] | LZn$^{II}$ (1/1) | 14.2 ± 1[b] | Buffer/DMSO (2/8) |
| 10 | LCu$^{II}$ (1/1) | 15.7 ± 1[b] | LZn$^{II}$ (1/1) | 13.5 ± 1[b] | Buffer/CH$_3$OH (1/1) |
| 12 | LCu$^{II}$ (1/1) | 16.0 ± 1[b] | LZn$^{II}$ (1/1) | ≈ 6 | Buffer/DMSO (2/8) |
| 13 | LCu$^{II}$ (1/1) | 14.7 ± 1[b] | — | — | Buffer/CH$_3$OH (1/1) |
| 17 | LCu$^{II}$ (1/1) | 16.0 ± 1[b] | LZn$^{II}$ (1/1) | 13.2 ± 1[b] | Buffer/CH$_3$OH (1/1) |
| 23 | LCu$^{II}$ (1/1) | 15.2 ± 1[b] | — | — | Buffer/CH$_3$OH (1/1) |

[a] According to Equation 8.
[b] According to Equation 7.
[c] Dioxane/20 mM Tris-HCl buffer pH = 7.4 containing 150 mM NaCl = 1/1 and 8/2 for the experiments with CuCl$_2$ and ZnCl$_2$, respectively.

TABLE 4

Comparison of competition reactions between the ligand 3 (L$_s$), CuCl$_2$ or ZnCl$_2$ (M) and the competing ligand EDTA (L$_c$) in a ratio of 1/1/1 at 15 μM in the different solvents used to determine apparent affinity constants for (K$_s$) metal ions.

| Metal ion | Solvent | % ML$_s$ | K$_s$[a] |
|---|---|---|---|
| Cu(II) | Buffer/CH$_3$OH (1/1) | 50 | 15.9 |
|  | Buffer/dioxane (1/1) | 45 | 15.7 |
|  | Buffer/DMSO (2/8) | 55 | 16.1 |
| Zn(II) | Buffer/CH$_3$OH (1/1) | 30 | 13.0 |
|  | Buffer/dioxane (2/8) | 33 | 13.1 |
|  | Buffer/DMSO (2/8) | 35 | 13.1 |
|  | CH$_3$OH | 40 | 13.3 |

The percentage of CuL$_s$ species at equilibrium is given.
[a] According to Equation 7.

Capacity of Compounds to Increase the Solubility of Proteins Involved in Neurodegenerative Diseases:

In the brain of people affected by Alzheimer's disease, the amyloid plaques mainly contain an (Aβ) peptide comprising 39-43 amino acids. It is produced by digestion of amyloid precursor protein (APP) by β- and γ-secretases. Aβ$_{1-40}$ and Aβ$_{1-42}$ peptides predominate. Pathogenesis is connected to the accumulation thereof and more particularly to that of Aβ$_{1-42}$, which is the most amyloidogenic and the production of which is amplified by the mutations inducing Alzheimer's' disease or by risk factors of these disease (M. P. Mattson, Nature, 2004, 430, 631-639; M. Citron, Nature Rev. Neurosci. 2004, 5, 677-685).

Reagents for Experiments Carried Out in the Presence of the Aβ$_{1-42}$ Amyloid Peptide:

Before use, the water [of Milli-Q Millipore quality] and all buffer solutions were treated on Chelex-100 resin (Biorad) (5 mg/ml) and filtered through 0.2 μm filters (Whatman) to remove potential traces of metal ions or particles.

CuCl$_2$, ZnCl$_2$ or FeCl$_3$ of puriss p.a. quality are from Fluka.

The β-amyloid peptide Aβ$_{1-42}$ (Aβ$_{1-42}$) was synthesised, purified (to a purity greater than 95%) and characterised by HPLC and MALDI-TOF mass spectrometry analysis. Working solutions of the peptide were prepared by solubilising 1 mg of lyophilised peptide in 500 μl of water and 500 μl of an aqueous NaOH solution pH=12.0, while stirring in a Thermomixer Comfort (Eppendorf). The peptide preparations are subsequently centrifuged for 10 minutes at 9,000 rpm and the supernatant is used as an "Aβ stock" solution. The concentration of peptide in the "Aβ stock" is determined immediately by colorimetric assay using a Micro BCA Protein Assays kit (Pierce) from standard ranges produced using known amounts of bovine serum albumin (BSA) then the Aβ$_{1-42}$ peptide solution is aliquoted and frozen rapidly in liquid nitrogen prior to being stored at −20° C. until being used.

The ligands are used in the form of hydrochlorides except in the case of 1 and 16, which are used in their hydrochloride form obtained during synthesis, 2,2'-methanediyl-bis(8-hydroxy-2-quinolinium)dichloride dihydrate and 2,2'-(methanediyl)-bis(7-methyloxy-8-hydroxy-2-quinolinium)dichloride respectively. Salts are generated by adding one hydrochloric acid equivalent per nitrogen group equivalent of the ligand dissolved in DMSO. After evaporation of the solvent, these salts are dissolved at the desired concentration with DMSO and kept at −20° C. until they are used.

Analysis of Aβ$_{1-42}$ Precipitation as a Function of the Cu(II)/Peptide Ratio:

The protocol was established from works by: C. S. Atwood et al., J. Neurochem. 2000, 75, 1219-1233. The final concentrations are given. Aβ$_{1-42}$ (5 μm, 500 μl) is set to aggregate in 20 mM Tris-HCl buffer containing 150 mM NaCl (pH=7.4) for 2 hours at 37° C. while stirring at 1,400 rpm in the presence of different CuCl$_2$ stoichiometries dissolved in DMSO (50 μl). Samples (final volume=550 μl) are subsequently centrifuged for 20 minutes at 9,000 rpm and 500 μl of supernatant are taken. The tube containing the precipitation pellet thus receives 450 μl of assay buffer/DMSO mixture (91/9, v/v). Then the protein concentration is determined on the supernatant and the pellet by Micro BCA Protein Assays (Pierce): each sample receives a volume of colour reagent and is incubated for 1 hour at 60° C. while stirring at 1,400 rpm then the absorbency at 562 nm is measured. Quantification is carried out on the basis of standard BSA ranges. The amounts of Aβ$_{1-42}$ actually contained in the pellet and the supernatant are obtained after a correction due to the presence of a residual portion of the supernatant (50/550 μl) in the pellet-containing fraction. For all experiments, the result of addition of the percentage of Aβ$_{1-42}$ in the supernatant to the percentage of Aβ$_{1-42}$ in the pellet gives values of approximately 100%.

The Cu(II) ion is known to induce the maximum of insoluble aggregated peptide-Aβ (C. S. Atwood et al., J. Biol. Chem. 1998, 273, 12817-12826). The Cu(II)/peptide ratio inducing the maximum aggregation under the experimental conditions used was first determined. FIG. 9 summarises the results obtained. Without addition of Cu(II), 47% of Aβ$_{1-42}$ is precipitated. Aggregation increases when the Cu(II)/Aβ$_{1-42}$ ratio increases to 2.5 Cu(II) through Aβ$_{1-42}$ then stabilises (82% of aggregated peptide).

Inhibition of the Precipitation of Aβ$_{1-42}$ by the Addition of Ligand:

The protocol was established from works by: C. S. Atwood et al., J. Neurochem. 2000, 75, 1219-1233. The final concentrations are given. 500 μl of Aβ$_{1-42}$ (5 μM is set to aggregate in 20 mM Tris-HCl buffer containing 150 mM NaCl (pH=7.4) for 1 hour at 37° C. while stirring at 1,400 rpm in the absence or presence of metal ions: CuCl$_2$, ZnCl$_2$ or FeCl$_3$ (20 μM). Then 50 μl of ligand to be tested (200 μM) dissolved in DMSO are added and the samples are incubated for 1 further hour at 37° C. while stirring at 1,400 rpm. The samples without ligand also receive 50 µl of DMSO. The samples (final volume=550 µl) are subsequently centrifuged for 20 min at 9,000 rpm, and 500 µl of supernatant are removed. The tube containing the precipitation pellet then receives 450 µl of assay buffer/DMSO mixture (91/9, v/v). Then the protein concentration is determined on the supernatant and the pellet by Micro BCA Protein Assays (Pierce): each sample receives a volume of colour reagent and is incubated for 1 hour at 60° C. while stirring at 1,400 rpm then the absorbency at 562 nm is measured. Quantification is carried out on the basis of standard BSA ranges. The amounts of $A\beta_{1-42}$ actually contained in the pellet and the supernatant are obtained after a correction due to the presence of a residual portion of supernatant in the pellet-containing fraction. In the case of 1, 2, 6, 12, 13, 14, 16, 17, 18, 23, of 8-hydroxyquinaldine and 8-aminoquinoline, which have absorption at 562 nm under the assay conditions, whites are produced in the presence of the tested ligand and of the investigated metal ion. For all experiments, the result of addition of the percentage of $A\beta_{1-42}$ in the supernatant to the percentage of $A\beta_{1-42}$ in the pellet gives values close to 100%.

The results obtained are summarised in Table 5. They demonstrate the capacity of the investigated compounds to increase the solubility of $A\beta_{1-42}$ in the presence of metal ions and even, in particular for 1, 2, 12, 13, 14, 15, 17, 18, 23 and 24, in the absence of these ions.

An additional test (not presented) has demonstrated that, in the presence of $CuCl_2$, the maximum level of peptide precipitation was achieved after 1 hour of incubation. It can therefore be proposed that, at least in the case of peptide aggregation in the presence of $CuCl_2$, the ligands (which are added only after 1 hour of incubation) merely prevent peptide aggregation but can probably act on previously formed aggregates.

TABLE 5

Analysis of solubilisation by the different $A\beta_{1-42}$ ligands aggregated in the absence or presence of metal ions. $A\beta_{1-42}$ (5 µM) is incubated for 1 hour at 37° C. in 20 mM Tris-HCl buffer (pH = 7.4) containing 150 mM NaCl in the presence or absence of 20 µM ($CuCl_2$, $ZnCl_2$ or $FeCl_2$) metal salt then for 1 further hour in the presence of 200 µM ligand, then the reaction mixtures are centrifuged. The amounts of soluble and precipitated $A\beta_{1-42}$ are determined in the supernatant and the precipitate respectively using a Micro BCA Protein Assays kit.

|  | without metal % soluble Aβ | $CuCl_2$ % soluble Aβ | $ZnCl_2$ % soluble Aβ | $FeCl_3$ % soluble Aβ |
| --- | --- | --- | --- | --- |
| uncombined Aβ | 55 ± 4 | 18 ± 2 | 29 ± 3 | 47 |
| 1 | 63 ± 4 | 60 ± 5 | 63 | 61 |
| 2 | 66 | 45 ± 5 | 57 | 58 |
| 3 | 56 | 47 ± 3 | 59 | 60 |
| 4 | 55 | 30 | 49 | 45 |
| 5 | 60 | 51 ± 1 | 50 | 52 |
| 6 | 56 | 58 ± 3 | 54 | 51 |
| 7 | 59 | 35 | 60 | 40 |
| 8 | 59 | 36 | 58 | 41 |
| 9 | 36 | 19 | 47 | 38 |
| 10 | 52 | 42 | 43 | 43 |
| 11 | 48 | 48 | 45 | 43 |
| 12 | 69 | 69 ± 2 | 52 | 59 |
| 13 | 71 ± 2 | 55 ± 3 | 57 | 66 |
| 14 | 79 ± 3 | 45 ± 3 | 57 | 51 |
| 15 | 72 | 35 | 23 | 42 |
| 16 | 53 | 48 ± 3 | 50 | 44 ± 6 |
| 17 | 63 ± 3 | 38 ± 4 | 42 ± 4 | 38 |
| 18 | 66 | 46 ± 3 | 62 ± 5 | 49 |
| 23 | 73 | 60 ± 4 | 58 ± 4 | 62 |
| 24 | 64 | 21 | 21 | 38 |

TABLE 5-continued

Analysis of solubilisation by the different $A\beta_{1-42}$ ligands aggregated in the absence or presence of metal ions. $A\beta_{1-42}$ (5 µM) is incubated for 1 hour at 37° C. in 20 mM Tris-HCl buffer (pH = 7.4) containing 150 mM NaCl in the presence or absence of 20 µM ($CuCl_2$, $ZnCl_2$ or $FeCl_2$) metal salt then for 1 further hour in the presence of 200 µM ligand, then the reaction mixtures are centrifuged. The amounts of soluble and precipitated $A\beta_{1-42}$ are determined in the supernatant and the precipitate respectively using a Micro BCA Protein Assays kit.

|  | without metal % soluble Aβ | $CuCl_2$ % soluble Aβ | $ZnCl_2$ % soluble Aβ | $FeCl_3$ % soluble Aβ |
| --- | --- | --- | --- | --- |
| 8-hydroxy-quinoline | 85 | 70 ± 3 | 88 | 80 |
| 8-hydroxy-quinaldine | 69 | 52 | 62 | 51 |
| Clioquinol | 63 | 55 ± 3 | 37 | 51 |
| 8-amino-quinoline | 66 ± 3 | 40 | 67 | 58 |
| EDTA | 41 | 65 | — | — |

Experiments were also carried out with regard to $A\beta_{1-42}$ (5 µM), $CuCl_2$ (12.5 µM) and the ligand (12.5 µM) in order to analyse the effect, on the aggregation reaction, of minimal stoichiometry (1/1) of ligand relative to the metal ion with a concentration of this ion leading to maximum peptide $A\beta_{1-42}$ precipitation. For all experiments, the result of the addition of the percentage of $A\beta_{1-42}$ in the supernatant to the percentage of $A\beta_{1-42}$ in the pellet gives values of approximately 100%.

The results obtained are summarised in FIG. 10.

A stoichiometry of 2.5 equivalents of Cu (II) per peptide was chosen because it is the minimum value inducing the maximum aggregation under the experimental condition employed (FIG. 9). For the control experiments with derivatives comprising a single quinoline residue, 5 equivalents of ligand were added because complexes of type $L_2Cu$ are conventionally used in these cases.

FIG. 10 summarises the results observed while comparing them with those of the previous experiments. Note that the activity of 1, 3, 5, 6, 11 and 18 is statistically identical, considering the values with a typical deviation ≦5%, whatever the conditions employed, whereas that of their analogues comprising a single quinoline residue (8-hydroxyquinoline, Clioquinol and 8-hydroxyquinaldine) decreases when the excess relative to the peptide or to Cu (II) decreases. For these two experimental conditions, the values are also close for 13 and 14. Under these two experimental conditions, 23 is also more active than its analogue comprising a single quinoline residue (8-aminoquinoline).

Capacity of the Compounds to Reduce the Oxidising Stress:

It has been proposed that the interactions of Aβ with the Fe and Cu ions can contribute to the creation of the lesions observed in brains affected by Alzheimer's disease. The synthetic peptides Aβ have toxicity which correlates with hydrogen peroxide ($H_2O_2$) production from $O_2$ via an oxidation-reduction mechanism on the metal ion (M. P. Mattson, *Nature* 2004, 430, 631-639).

Quantitative Analysis of the Hydrogen Peroxide Produced by $A\beta_{1-42}$ in the Presence of $CuCl_2$, Reducing Agent, Air and Ligand:

The protocol was established from works by: X. Huang et al., *J. Biol. Chem.* 1999, 274, 37111-37116; X. Huang et al., *Biochemistry* 1999, 38, 7609-7616; C. Opazo et al., *J. Biol. Chem.* 2002, 277, 40302-40308; K. J. Barnham et al., *J. Biol. Chem.* 2003, 278, 42959-42965; G. D. Ciccotosto et al., *J. Biol. Chem.* 2004, 279, 42528-42534.

The final concentrations are given. The reactions were carried out in the dark in mM sodium phosphate buffer (pH=7.4). $A\beta_{1-42}$ (0.2 μM) and $CuCl_2$ (0.4 μM) were pre-incubated for 1 hour at 37° C. while stirring at 1,400 rpm in 375 μl of buffer. Then 2 μl of a solution of ligand to be investigated (0.2; 0.4 or 0.8 μM) in DMSO were added. After incubation for a further hour, 2 μl of an aqueous sodium ascorbate solution (10 μM) were added and incubation was continued for 5 min while stirring. The amount of $H_2O_2$ produced is then quantified using an Amplex Red $H_2O_2$/HRP Assay Kit (Molecular Probes) while adding a volume of assay reagent to the samples, then incubating them for 1 hour at 37° C. while stirring at 500 rpm. $H_2O_2$ is then detected by spectrophotometry at 563 nm. Quantification is carried out on the basis of standard curves obtained with known amounts of $H_2O_2$. The results obtained are summarised in Table 6 and FIG. 11.

Experiments were also carried out in the presence of a known amount of $H_2O_2$, added just before or just after the addition of sodium ascorbate, in order to investigate the stability of $H_2O_2$ under the experimental conditions employed. The results obtained are summarised in Table 7.

Other experiments were carried out in the presence of different concentrations of peptide $A\beta_{1-42}$ (0.2 to 0.53 μM) and $CuCl_2$ (0.4 μM), with or without addition of ligand (0.4 μM) and of known amounts of $H_2O_2$, in order to investigate the influence of the stoichiometry $A\beta_{1-42}$/Cu on the production of $H_2O_2$ by the investigated systems. The results obtained are summarised in FIG. 11.

The peptide $A\beta$ can chelate various stoichiometries of Cu(II) and thus form different types of complexes. All these species can have different capacities to produce $H_2O_2$ in the presence of dioxygen and reducing agent. Titration of the amount of $H_2O_2$ produced by 0.4 μM of Cu(II) as a function of the concentration of $A\beta_{1-42}$ causes this phenomenon to appear (FIG. 11). The amount of $H_2O_2$ produced increases when the Cu/$A\beta_{1-42}$ ratio increases. The same experiments were carried out in the presence of 1 equivalent of ligand 3 or 7 (II) per Cu(II). The two compounds virtually inhibit $H_2O_2$ production, whatever the tested Cu/$A\beta_{1-42}$ ratio.

Table 6 shows that the various quinoline derivatives tested inhibit the production of $H_2O_2$, whatever the experimental conditions employed.

TABLE 6

Comparison of inhibition by the various ligands (0.4 μM) of the production of $H_2O_2$ effected by $A\beta_{1-42}$ (0.2 and 0.5 μM) in the presence of $CuCl_2$ 0.4 μM), ascorbate (10 μM) and air.

| Ligand 1 eq/ Cu(II) (when not specified) | without $A\beta_{1-42}$ | 0.2 μM $A\beta_{1-42}$ Cu/$A\beta$ = 2 | 0.5 μM $A\beta_{1-42}$ Cu/$A\beta$ = 0.75 |
|---|---|---|---|
| without ligand | 2.91 ± 0.22 | 2.83 ± 0.19 | 1.08 |
| 1 | 0.54 | 0.75 ± 0.11 | 0.76 |
| 2 | 0.56 | 0.80 ± 0.23 | 0.61 |
| 3 0.5 eq/Cu(II) | 2.12 | 0.94 | — |
| 1 eq/Cu(II) | 0.84 | 0.71 ± 0.02 | 0.55 |
| 1.5 eq/Cu(II) | — | 0.49 | — |
| 4 | 0.12 | 0.37 ± 0.09 | 0.35 |
| 5 | 0.39 | 0.55 ± 0.08 | — |
| 6 | 0.82 | 0.86 ± 0.11 | — |
| 7 | 0.75 | 0.89 ± 0.07 | 0.68 |
| 8 | 0.66 | 0.89 ± 0.09 | 0.64 |
| 9 | 0.66 | 0.82 ± 0.08 | 0.82 |
| 12 | 0.40 | 0.47 ± 0.09 | — |
| 13 | 0.89 | 2.10 | 0.70 |
| 14 | 0.74 | 1.99 | 0.78 |
| 15 | — | 1.02 | — |

TABLE 6-continued

Comparison of inhibition by the various ligands (0.4 μM) of the production of $H_2O_2$ effected by $A\beta_{1-42}$ (0.2 and 0.5 μM) in the presence of $CuCl_2$ 0.4 μM), ascorbate (10 μM) and air.

| Ligand 1 eq/ Cu(II) (when not specified) | without $A\beta_{1-42}$ | 0.2 μM $A\beta_{1-42}$ Cu/$A\beta$ = 2 | 0.5 μM $A\beta_{1-42}$ Cu/$A\beta$ = 0.75 |
|---|---|---|---|
| 16 | — | 0.70 | — |
| 17 | — | 0.69 | — |
| 18 | 0.47 | 0.47 | 0.45 |
| 23 | 0.65 | 0.69 | 0.49 |
| 24 | 0.49 | 0.62 | 0.47 |
| 8-hydroxy-quinoline | | | |
| 1 eq/Cu(II) | 2.02 | 0.69 | 0.75 |
| 2 eq/Cu(II) | 0.62 | 0.71 ± 0.05 | 0.62 |
| Clioquinol | | | |
| 1 eq/Cu(II) | 2.07 | 0.89 ± 0.08 | 0.64 |
| 2 eq/Cu(II) | 0.54 | 0.78 ± 0.06 | 0.57 |
| without ligand and without Cu(II) | 0.49 ± 0.19 | 0.69 | 0.51 |
| without ligand, without ascorbate and without Cu(II) | 0 | 0.06 | — |

The figures in the tables correspond to the amount of $H_2O_2$ (expressed in nanomoles) added using an Amplex Red $H_2O_2$/HRP Assay kit.

In a control experiment carried out with only the ligand without amyloid peptide $\beta_{1-42}$ and without Cu, determination of the production of $H_2O_2$ due to traces of metals present in the investigated medium is always less than 0.49±19 nanomoles of $H_2O_2$.

Table 7 shows that, under the experimental conditions employed, the ligands can be divided into two categories: (i) those which inhibit the production of $H_2O_2$ but do not degrade it (all of the added $H_2O_2$ is found again); (ii) those for which the decrease in $H_2O_2$ is associated with its degradation (as in the case of 12 where none of the added $H_2O_2$ is found again).

TABLE 7

Analysis of the stability of $H_2O_2$ during experiments to inhibit, via the l igands, production of $H_2O_2$ effected by $A\beta_{1-42}$ (0.2 or 0.4 μM) in the presence of $CuCl_2$ (0.4 μM), ascorbate (10 μM) and air. Analysis is achieved by comparing the results obtained with or without addition of a known amount of $H_2O_2$ in the reaction medium just after the addition of ascorbate, if not specified by b). The theoretical value of $H_2O_2$ is given in parentheses if there is no degradation. It corresponds to the addition of the number of nanomoles of $H_2O_2$ added to those produced in a reaction carried out under the same experimental conditions but without addition of $H_2O_2$.

| $A\beta_{1-42}$ 0.2 μM[a] 0.075 nanomole | Cu(II) 0.4 μM 0.15 nanomole | ascorbate 10 μM 3.8 nanomoles | ligand 0.4 μM[a] 0.15 nanomole | $H_2O_2$ added nanomoles | $H_2O_2$ assayed nanomoles |
|---|---|---|---|---|---|
| — | — | + | — | — | 0.49 ± 0.19 |
| — | — | + | — | 3.0 | 3.2 (3.5) |
| — | — | + | + | — | 2.91 ± 0.22 |
| — | + | + | — | 1.5 | 4.0 (4.4) |
| — | + | + | — | 1.5[b] | 3.6 (4.4) |
| + | + | + | — | — | 2.83 ± 0.19 |
| + | + | + | — | 1.5 | 4.2 (4.3) |
| + | + | + | — | 1.5[b] | 4.2 (4.3) |
| 0.4 μM | + | + | — | — | 1.6 |
| 0.4 μM | + | + | — | 1.5 | 3.0 (3.1) |
| 0.4 μM | + | + | — | 1.5[b] | 3.0 (3.1) |

TABLE 7-continued

Analysis of the stability of $H_2O_2$ during experiments to inhibit, via the ligands, production of $H_2O_2$ effected by $A\beta_{1-42}$ (0.2 or 0.4 μM) in the presence of $CuCl_2$ (0.4 μM), ascorbate (10 μM) and air. Analysis is achieved by comparing the results obtained with or without addition of a known amount of $H_2O_2$ in the reaction medium just after the addition of ascorbate, if not specified by b). The theoretical value of $H_2O_2$ is given in parentheses if there is no degradation. It corresponds to the addition of the number of nanomoles of $H_2O_2$ added to those produced in a reaction carried out under the same experimental conditions but without addition of $H_2O_2$.

| $A\beta_{1-42}$ 0.2 μM[a] 0.075 nanomole | Cu(II) 0.4 μM 0.15 nanomole | ascorbate 10 μM 3.8 nanomoles | ligand 0.4 μM[a] 0.15 nanomole | $H_2O_2$ added nanomoles | $H_2O_2$ assayed nanomoles |
|---|---|---|---|---|---|
| — | + | — | 3 | 3.0 | 3.1 |
| — | + | + | 3 | — | 0.84 |
| — | + | + | 3 | 3.0 | 3.8 (3.8) |
| + | + | + | 3 | — | 0.71 ± 0.02 |
| + | + | + | 3 | 3.0 | 3.7 (3.7) |
| + | + | + | 3 | 3.0[b] | 3.8 (3.7) |
| + | + | + | 4 | — | 0.37 ± 0.09 |
| + | + | + | 4 | 3.0 | 3.3 (3.4) |
| + | + | + | 5 | — | 0.55 ± 0.08 |
| + | + | + | 5 | 3.0 | 3.4 (3.5) |
| + | + | + | 6 | — | 0.87 ± 0.11 |
| + | + | + | 6 | 3.0 | 3.6 (3.9) |
| + | + | + | 12 | — | 0.47 ± 0.09 |
| + | + | + | 12 | 3.0 | 1.7 (3.4) |
| + | + | + | 14 | — | 1.99 ± 0.11 |
| + | + | + | 14 | 3.0[b] | 4.9 (5.0) |
| — | + | + | 18 | — | 0.47 |
| — | + | + | 18 | 3.0[b] | 3.5 (3.5) |

$H_2O_2$ is assayed using an Amplex Red $H_2O_2$/HRP Assay kit.
[a] When not specified
[b] $H_2O_2$ added just before the ascorbate.

Modulation of Hydrophobicity:

Determination of log $D_{74}$:

The method is adapted from Z.-P Zhuang et al., *J. Med. Chem.*, 2001, 44, 1905-1914. The ligand (2.0 mg) is dissolved in 2 ml of 1-octanol then 2 ml of 20 mM Tris-HCl buffer, pH=7.4 containing 150 mM NaCl are added. After mixing in a vortex for 3 min at ambient temperature, followed by centrifugation for 5 min at 9,000 rpm, the concentration of the ligand in each phase is determined by UV-visible spectrophotometry. The 1-octanol fractions are thus redivided until reproducible values of coefficient of division of obtained. This coefficient is expressed as the decimal logarithm of [(the concentration of ligand contained in the 1-octanol phase)/(the concentration of ligand contained in the buffered aqueous phase)]=log $D_{7.4}$. Measurements were taken three times.

Table 8 summarises the results obtained.

The value of log $D_{7.4}$ reflects the hydrophobicity and therefore the lipophilicity of the compounds, which is one of the parameters used (with others such as the molecular weight) to estimate the possibilities of biodistribution of the molecules (H. van de Waterbeemd et al., *Nature Rev. Drug Discovery* 2003, 2, 192-204).

For identical substitutions of the aromatic macrocycles, the derivatives comprising a single quinoline residue are more hydrophilic than those comprising a plurality thereof. The hydrophobicity can be modulated by the length of the arm joining the quinoline residues (compare 7 and 10), by the nature of said arm (compare 7 and 18) and by the substitution of the hydrogens of the rings (compare respectively: 1 and 2; 3 and 4; 7, 8, 9 and 17) or joining arms (compare 1, 3, 5 and 6 by different groups.

TABLE 8

Value of the decimal logarithm of the coefficient of division of the ligands between 1-octanol (hydrophobic phase) and 20 mM Tris-HCl buffer containing 150 mM NaCl (pH = 7.4) (hydrophilic phase) (1/1, v/v).

| Ligand | PM | log $D_{7.4}$ |
|---|---|---|
| 1 | 301 | 3.3 ± 0.1 |
| 2 | 370 | 3.5 ± 0.1 |
| 3 | 330 | 4.4 ± 0.1 |
| 4 | 398 | 4.9 ± 0.1 |
| 5 | 338 | 3.8 ± 0.1 |
| 6 | 316 | 3.9 ± 0.1 |
| 7 | 316 | 3.5 ± 0.1 |
| 8 | 384 | 4.2 ± 0.1 |
| 9 | 636 | 5.6 ± 0.5 |
| 10 | 344 | 3.8 ± 0.1 |
| 11 | 474 | 3.7 ± 0.1 |
| 12 | 271 | 3.5 ± 0.1 |
| 13 | 328 | 2.7 ± 0.1 |
| 14 | 342 | 1.8 ± 0.1 |
| 15 | 272 | 2.0 ± 0.1 |
| 17 | 376 | 3.5 ± 0.1 |
| 18 | 331 | 3.0 ± 0.1 |
| 23 | 357 | 2.5 ± 0.1 |
| 24 | 299 | 2.6 ± 0.1 |
| 8-hydroxyquinoline | 145 | 2.1 ± 0.1 |
| 8-hydroxyquinaldine | 159 | 2.4 ± 0.1 |
| Clioquinol | 305 | 3.8 ± 0.1 |
| 8-aminoquinoline | 144 | 1.9 ± 0.1 |

Analysis of Potential Genotoxicity:

AMES Test:

The method is adapted from D. M. Maron and B. N. Ames, *Mutat. Res.* 1983, 113, 173-215; D. E. Levin et al., *Mutat. Res.* 1982, 94, 315-330; D. E. Levin et al. *Proc. Natl. USA* 1982, 79, 7445-7449.

Two test lines (TA98 and TA100) of mutant *Salmonella tiphimurium* (His⁻) were used on account of their inability to synthesise histidine and the confirmation of the characteristics of these lines by genetic label experiments. The test involves evaluating the potential of the tested molecules to induce mutation which is reverse to the histidine locus of these lines. These two lines were provided by Dr. Bruce N. Ames (University of California, Berkeley, USA). They are resistant to Ampicillin and sensitive to Tetracycline. They are not mutant toward rfa, UvγV and UvγA. The line TA98 (his D3052) contains a mutation of reading phase (GC) whereas the line TA100 (his G46) contains a substitution of base pair (GC). The number of spontaneous revertants is 37±6 and 166±15 colonies per plate in the case of TA98 and TA100 respectively.

The compounds to be tested were dissolved in 100% of DMSO (the solvent) and diluted logarithmically (by a factor of 10) so as to obtain 4 test concentrations of 30,000; 3,000; 300 and 30 μg/ml. Each series of 0.1 ml of stock solution to be tested, 0.1 ml of test line and of culture medium with or without 0.5 ml of enzymatic homogenate (S9) of rat liver microsome were mixed with 2 ml of molten agarose (containing 0.5 mM of histidine and 0.5 mM of biotin). This mixture was placed on the surface of a plate of minimal agarose glucose medium (30 ml for each Petri dish) so as to obtain final concentrations of compound to be tested of 3,000; 300; 30 and 3 μγ/plate. The plates were then incubated at 37° C. for 48 hours. The cultures were treated or not treated in the presence of an exogenous metabolic activation by the addition of 0.5 ml of mixture S9 containing 8 mM $MgCl_2$, 33 mM KCl, 4 mM NADP, 5 mM glucose-6-phosphate, 100 mM $NaH_2PO_4$ (pH=7.4) and 4% (v/v) of enzymatic homogenate of rat liver microsome induced by Acrolor 1254 (S9). The revertant colonies of the test lines were counted using a colony counter (Sigma). The results were considered as significant only if the values obtained for the solvent alone and the reference compounds were in a previously established range. A number of colonies ≧3 times the number of colonies observed for the solvent alone is deemed to be significantly mutagenic. A compound inducing a number of colonies <50% of cells obtained for the solvent alone was deemed to be toxic for the bacteria tested. All the experiments were carried out in triplicate.

The obtaining of expected results with these lines for 4-NPC, sodium azide, 2-anthramine and 2-aminofluorene confirmed the high quality of the investigation.

The results obtained are summarised in Table 9.

TABLE 9

Results of the Ames test for mutagenicity of Salmonella on the TA98 and TA100 strains of salmonella in the absence or presence of enzymatic homogenate (S9) of rat liver microsome.

| Compound (value per plate) | Addition of S9 | TA98 Mutagenic effect | TA98 Cytotoxicity | TA100 Mutagenic effect | TA100 Cytotoxicity |
|---|---|---|---|---|---|
| DMSO (solvent) | no | >100 µl | >100 µl | >100 µl | >100 µl |
|  | yes | >100 µl | >100 µl | >100 µl | >100 µl |
| Clioquinol | no | — | 300 µg | — | 30 µg |
|  | yes | — | 300 µg | — | 30 µg |
| 3 | no | >3000 µg | >3000 µg | >3000 µg | >3000 µg |
|  | yes | >3000 µg | >3000 µg | >3000 µg | >3000 µg |
| 5 | no | >3000 µg | >3000 µg | — | 300 µg |
|  | yes | >3000 µg | >3000 µg | >3000 µg | >3000 µg |
| 12 | no | >3000 µg | >3000 µg | >3000 µg | >3000 µg |
|  | yes | >3000 µg | >3000 µg | >3000 µg | >3000 µg |

A bactericidal effect of Clioquinol is observed on the two lines. No mutagenic effect was observed on the polyquinoline compounds tested, even in the case of the strongest doses investigated. No bactericidal effect was observed for these compounds, even in the case of the strongest doses tested, except for compound 5 as from 300 µg/plate, on the TA100 line in the absence of S9.

The invention claimed is:

1. A method for chelating metal ion and/or dissolving amyloid aggregates, comprising contacting metal ions and/or amyloid aggregates with a compound of formula (I):

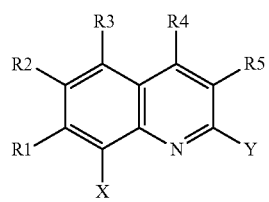

wherein in formula (I):
X represents an —NRR' group and
Y represents a group of formula:

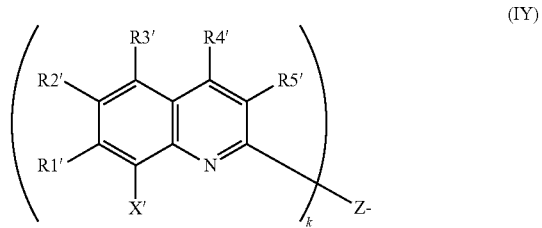

in which X' represents an —NRR' group and
Z represents a group of formula -(Alk)$_n$-(A')-(Alk')$_{n'}$, where:
n, n' are the same or different and independently represent 0 or 1, A' is —NR—,
Alk, Alk' are the same or different and independently represent an -alkyl-group,
R and R' are the same or different and independently represent a hydrogen atom or a cycloalkyl or alkyl group, optionally substituted by one or more groups selected from OR, NRR', Hal, —CN, —CF$_3$, S(O)$_p$R, COOR, OCOOR, CONRR' and NRCOOR', heteroaryl;
R1=R2=R3=R4=R5=R1'=R2'=R3'=R4'=R5'=H, k is 1, p is 0, 1 or 2;
as well as the pharmaceutically acceptable stereoisomers or mixtures, tautomeric forms, hydrates, solvates, salts, free forms and esters thereof.

2. The method according to claim 1, wherein the compounds are selected from the group consisting of:
2,2'-(iminodimethanediyl)di(N-boc-8-quinoline amine),
2,2'-(iminodimethanediyl)di(8-quinoline amine),
2,2'-[(butylimino)dimethanediyl]di(N-boc-8-quinoline amine),
2,2'-[(butylimino)dimethanediyl]di(8-quinoline amine),
N-butyl-2,2'-imino-bis(8-quinoline amine), and
N-butyl-2,2'-imino-bis(8-quinoline amine).

3. The method according to claim 1, wherein in formula (I) X represents NRR' and Y represents a group of formula (IY), in which
X' represents NRR' and Z represents Alk-NR"-Alk, where Alk represents a linear or branched alkyl group optionally substituted by one or more halogen atoms; or
X represents NRR' and Y represents a group of formula (IY), in which X' represents NRR' and Z represents NR";
k=1 and
R1=R2=R3=R4=R5=R1'=R2'=R3'=R4'=R5'=H.

4. The method according to claim 1, wherein said metals are selected from copper.

5. A method for chelating metal ions and/or dissolving amyloid aggregates in a patient having a disease chosen from Alzheimer's disease, Parkinson's disease, Huntington's disease, amyotrophic lateral sclerosis, comprising administering to an effective amount of a compounds of formula (I)

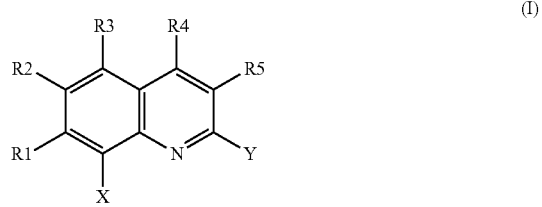

wherein in formula (I):
X represents an —NRR' group and
Y represents a group of formula:

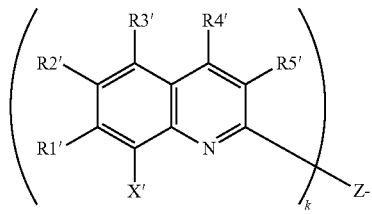

(IY)

in which X' represents an —NRR' group and
Z represents a group of formula -(Alk)$_n$-(A')-(Alk')$_{n'}$, where
n, n' are the same or different and independently represent 0 or 1, A' is —NR—,
Alk, Alk' are the same or different and independently represent an -alkyl-group,
R and R' are the same or different and independently represent a hydrogen atom or a cycloalkyl or alkyl group, optionally substituted by one or more groups selected from OR, NRR', Hal, —CN, —CF$_3$, S(O)$_p$R, COOR, OCOOR, CONRR' and NRCOOR'; heteroaryl;
R1=R2=R3=R4=R5=R1'=R2'=R3'=R4'=R5'=H, k is 1, p is 0, 1 or 2;
as well as the pharmaceutically acceptable stereoisomers or mixtures, tautomeric forms, hydrates, solvates, salts, free forms and esters thereof.

6. The method according to claim 5, wherein in formula (I) X represents NRR' and Y represents a group of formula (IY), in which
X' represents NRR' and Z represents Alk-NR"-Alk, where Alk represents a linear or branched alkyl group optionally substituted by one or more halogen atoms; or
X represents NRR' and Y represents a group of formula (IY), in which X' represents NRR' and Z represents NR";
k=1 and
R1=R2=R3=R4=R5=R1'=R2'=R3'=R4'=R5'=H.

7. The method according to claim 5, wherein the compounds are selected from the group consisting of:
2,2'-(iminodimethanediyl)di(N-boc-8-quinoline amine),
2,2'-(iminodimethanediyl)di(8-quinoline amine),
2,2'-[(butylimino)dimethanediyl]di(N-boc-8-quinoline amine),
2,2'-[(butylimino)dimethanediyl]di(8-quinoline amine),
N-butyl-2,2'-imino-bis(8-quinoline amine), and
N-butyl-2,2'-imino-bis(8-quinoline amine).

* * * * *